(12) United States Patent
Sakai et al.

(10) Patent No.: US 6,277,616 B1
(45) Date of Patent: Aug. 21, 2001

(54) ENDO-FUCOIDAN-LYASE

(75) Inventors: Takeshi Sakai; Hitomi Kimura; Kaoru Kojima, all of Hirosaki; Katsushige Ikai; Sumiko Akiyoshi, both of Otsu; Yoshikuni Nakanishi; Ikunoshin Kato, both of Hirosaki, all of (JP)

(73) Assignees: Takara Shuzo Co. Ltd., Kyoto; Research Institute for Glycotechnology, Aomori, both of (JP)

( * ) Notice: Subject to any disclaimer, the term of this patent is extended or adjusted under 35 U.S.C. 154(b) by 0 days.

(21) Appl. No.: 09/517,633

(22) Filed: Mar. 3, 2000

Related U.S. Application Data

(62) Division of application No. 08/930,002, filed as application No. PCT/JP96/01080 on Apr. 22, 1996, now Pat. No. 6,054,577.

(30) Foreign Application Priority Data

Apr. 28, 1995 (JP) .................................................. 7-127453

(51) Int. Cl.⁷ .............................. C12N 9/24; C12N 1/12; C12N 9/88
(52) U.S. Cl. ........................ 435/200; 435/252.1; 435/232
(58) Field of Search ..................................... 435/232, 200, 435/252.1

(56) References Cited

U.S. PATENT DOCUMENTS 5,588,254 * 12/1996 Adachi et al. ....................... 47/57.6

FOREIGN PATENT DOCUMENTS

| 03 224 484 | * 10/1991 | (JP) . |
|---|---|---|
| 404 169 189 | * 6/1992 | (JP) . |
| 7-59563 | 3/1995 | (JP) . |
| 7-215990 | 8/1995 | (JP) . |
| 8-266 | 1/1996 | (JP) . |

OTHER PUBLICATIONS

Quatrano et al., J. Cell Sci. Suppl., 2, 129–141, 1985.*
Vilter, Planta Medica (Journal of Medicinal Plant Research), No. 5, 417, 1986.*

* cited by examiner

*Primary Examiner*—David M. Naff
*Assistant Examiner*—Mike Meller
(74) *Attorney, Agent, or Firm*—Wenderoth, Lind & Ponack, L.L.P.

(57) ABSTRACT

An isolated endo-fucoidan-lyase is described. The enzyme acts on fucoidan, has a pH optimum from 6 to 10, and has an optimum pH from 30 to 40° C. The enzyme can be isolated from Flavobacterium sp. FERM BP-5402. The enzyme is used to obtain sugar compounds which are useful in the study on carbohydrates.

3 Claims, 41 Drawing Sheets

ENDO-FUCOIDAN-LYASE

This application is a divisional application of now allowed Ser. No. 08/930,002 filed Sep. 26, 1997 now U.S. Pat. No. 6,054,577, which is a 371 of PCT/JP96/01080 filed Apr. 22, 1996.

TECHNICAL FIELD

This invention relates to sugar compounds useful in the field of studies on carbohydrates, a polysaccharide lyase useful in the production of these sugar compounds and a microorganism belonging to the genus Fucoidanobacter useful in the production of the sugar compounds.

BACKGROUND ART

There has been reported that fucoidan, which is a sulfated polysaccharide contained in brown algae (Phaeophyta), has various biological activities including anticoagulant, lipemia-clearing, antitumor, cancerous metastasis-inhibitory and anti-AIDS virus infection effects. Thus fucoidan is highly useful as a medicine.

When it is intended to use fucoidan as such as a medicine, however, there arise problems in antigenicity, uniformity, anticoagulant activity, etc., since fucoidan is a sulfated polysaccharide having an extremely large molecular weight. Accordingly, it is often needed to degrade fucoidan to a certain extent.

It has been therefore desired to clarify the structure of fucoidan and reveal the relation thereof with its biological activities. However, fucoidan is a high-molecular compound carrying many branched chains and various constituting sugars. Moreover, its sulfate groups are bonded to various positions. These characteristics make it highly difficult to analyze the structure of fucoidan. To analyze the structure of a polysaccharide, there is known a method comprising treating the polysaccharide with an enzyme capable of degrading the same and analyzing the structures of the oligosaccharides thus formed. However there has been commercially available neither any fucoidan degrading enzyme giving products with known sugar chain structure nor one serving as the standard of a fucoidan oligosaccharide from among those reported hitherto.

For these reasons, there have been required sugar compounds with identified structures, a polysaccharide degrading enzyme useful in the production of these sugar compounds and a microorganism useful in the production of the sugar compounds.

The present invention aims at providing sugar compounds usable in analyzing the structure of fucoidan, identifying enzymatically degraded products of fucoidan and detecting the biological activities thereof, a novel endo-fucoidan-lyase useful in studies on fucoidan such as the production of fucoidan oligosaccharides and a novel microorganism useful for producing the sugar compounds.

In short, the first invention of the present invention relates to sugar compounds represented by the following general formula (1) or (2), wherein at least one alcoholic hydroxyl group has been sulfated, or salts thereof:

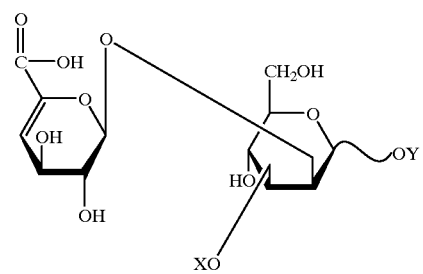

(1)

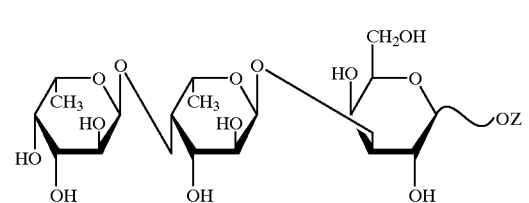

(2)

wherein X represents hydrogen or a group represented by the following formula (3):

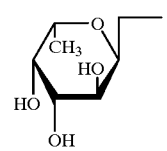

(3)

Y represents hydrogen or a group represented by the following formula (4) or (5):

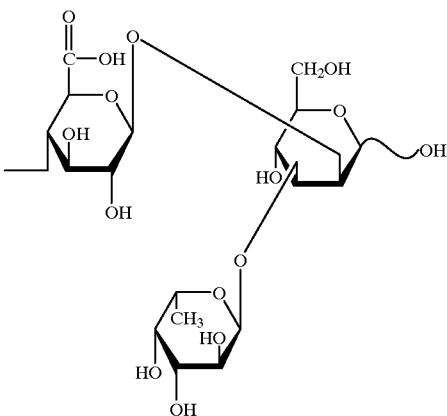

(4)

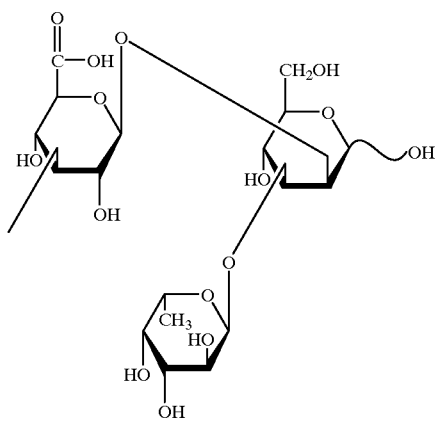
(5)
provided that X and Y are not hydrogen at the same time; and
Z represents hydrogen or a group represented by the following formula (6):
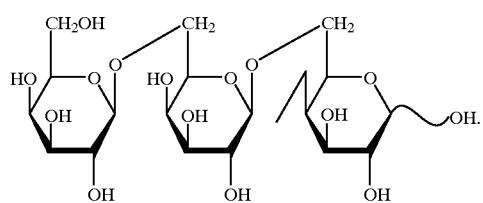
(6)
Examples of the compounds represented by the above general formula (1) or (2) are those represented by the following general formulae (7) to (15):
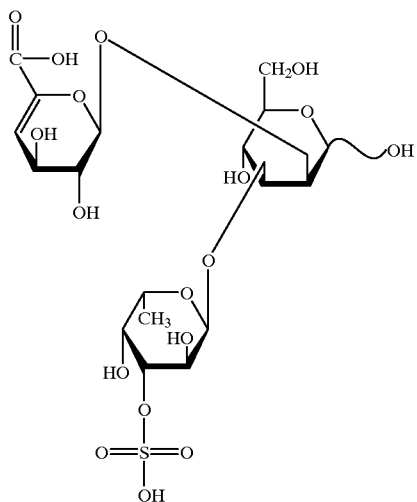
(7)
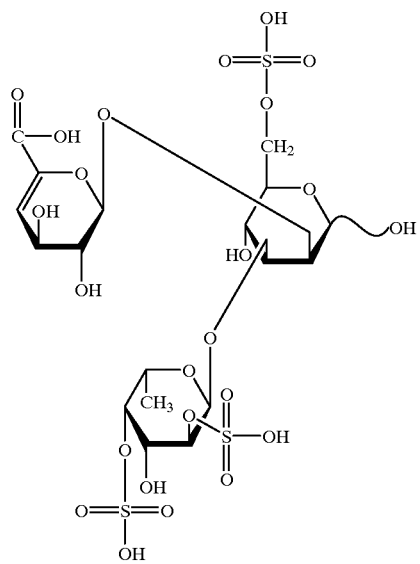
(8)
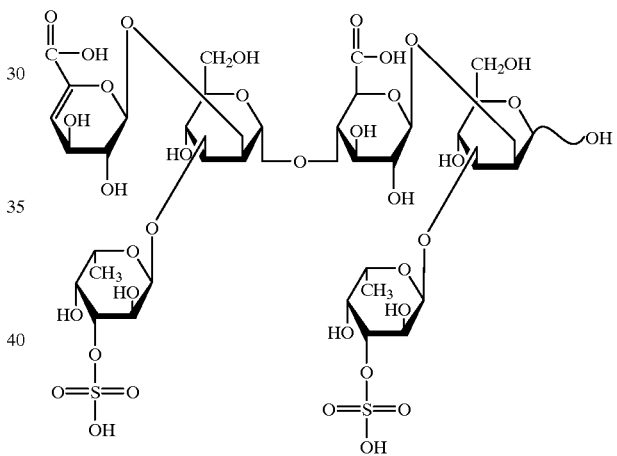
(9)
(10)

(11)

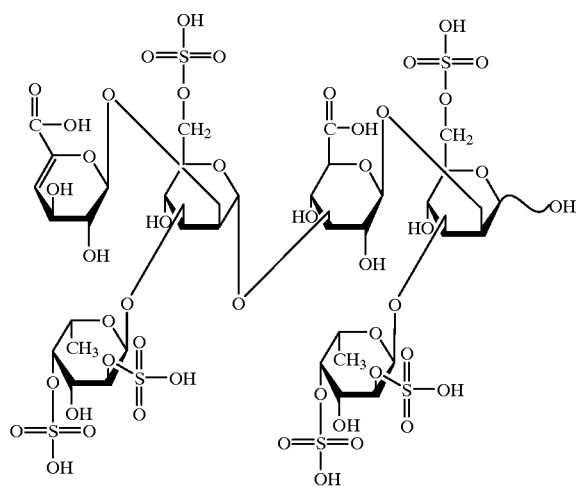

(14)

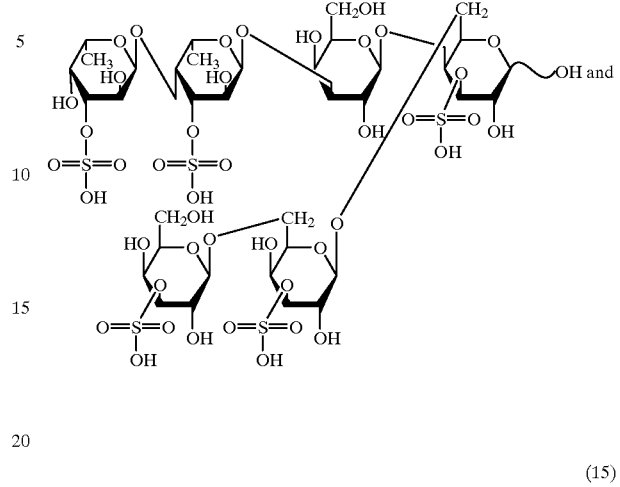

(12)

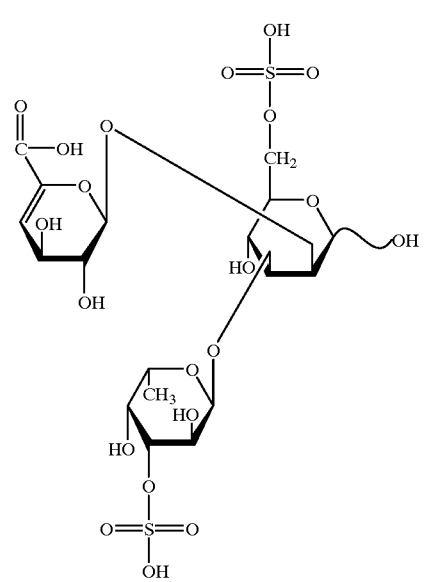

(15)

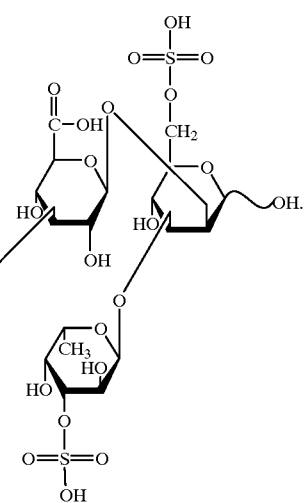

The second invention of the present invention relates to an endo-fucoidan-lyase characterized by having the following physicochemical properties.

(I) Function: acting on fucoidan and thus liberating at least the compounds represented by the above formulae (7) and (8).

(II) Optimum pH value: ranging from pH 6 to 10.

(III) Optimum temperature: ranging from 30 to 40° C.

The third invention of the present invention relates to a bacterium belonging to the genus Fucoidanobacter which is a novel microorganism useful in the production of the sugar compounds of the first invention of the present invention, having menaquinone in the electron transport chain and containing 60% of GC mole percent guanine plus cytosine content (mol % G+C).

In the formulae (1), (2), (4) to (15) and (17) to (25) given herein, "~" means that mannose or galactose occurs as both of α- and β-anomers.

The present inventors have found out that the sugar compounds of the present invention can be obtained by (13)

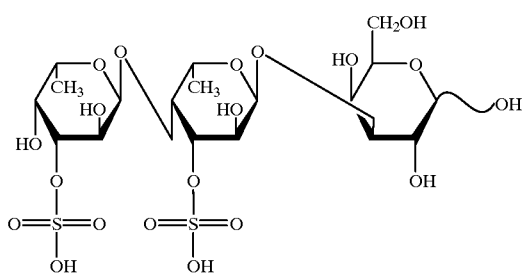

treating fucoidan with the enzyme of the second invention of the present invention or the cell extract or culture supernatant of the bacterium of the third invention of the present invention, thus completing the present invention.

Figure 1:
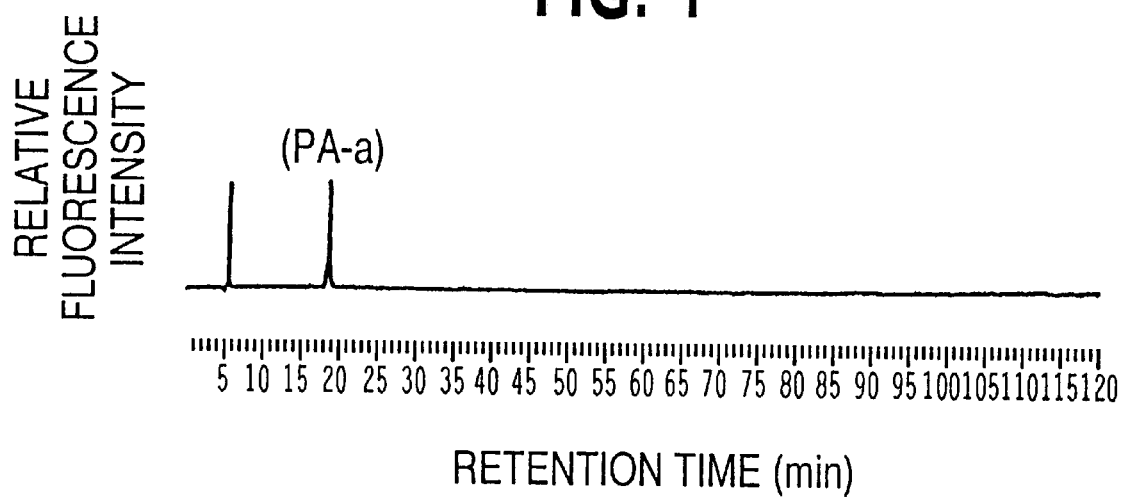
FIG. 1 shows the elution pattern of the sugar compound (a) having been pyridyl-(2)-aminated (PA-a) which is eluted from an L-column.
Figure 2:
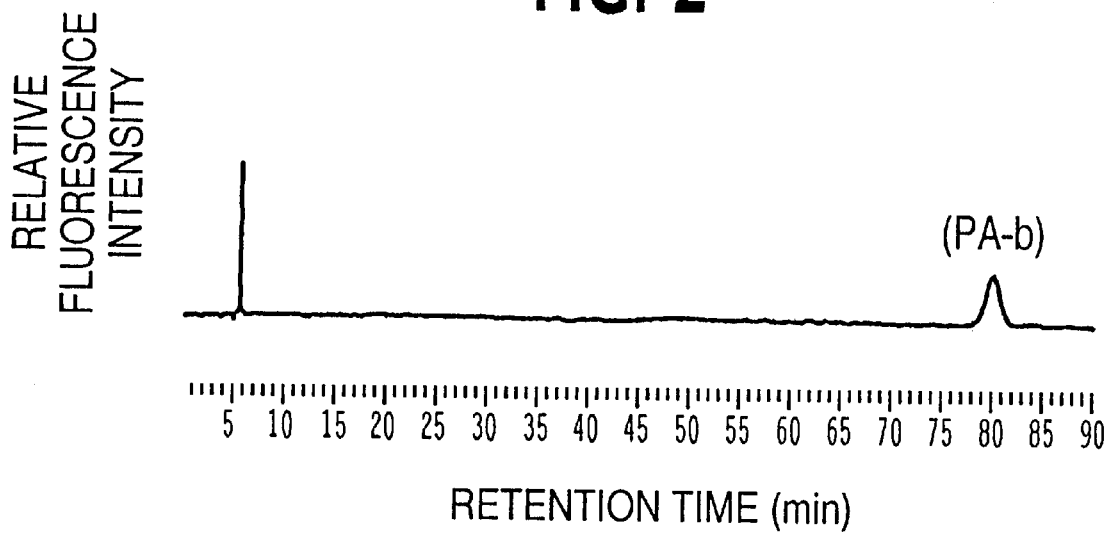
FIG. 2 shows the elution pattern of the sugar compound (b) having been pyridyl-(2)-aminated (PA-b) which is eluted from an L-column.
Figure 3:
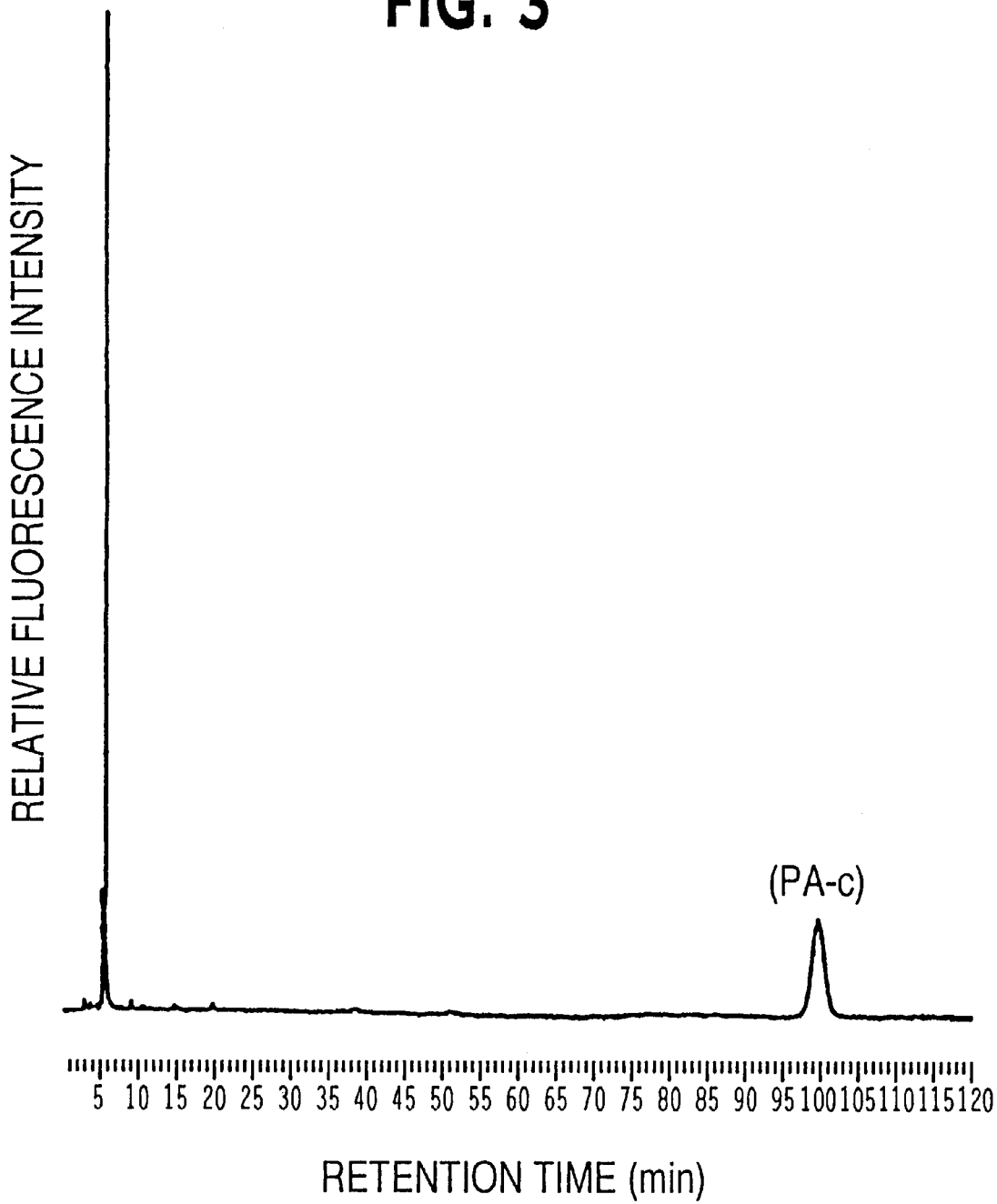
FIG. 3 shows the elution pattern of the sugar compound (c) having been pyridyl-(2)-aminated (PA-c) which is eluted from an L-column.
Figure 4:
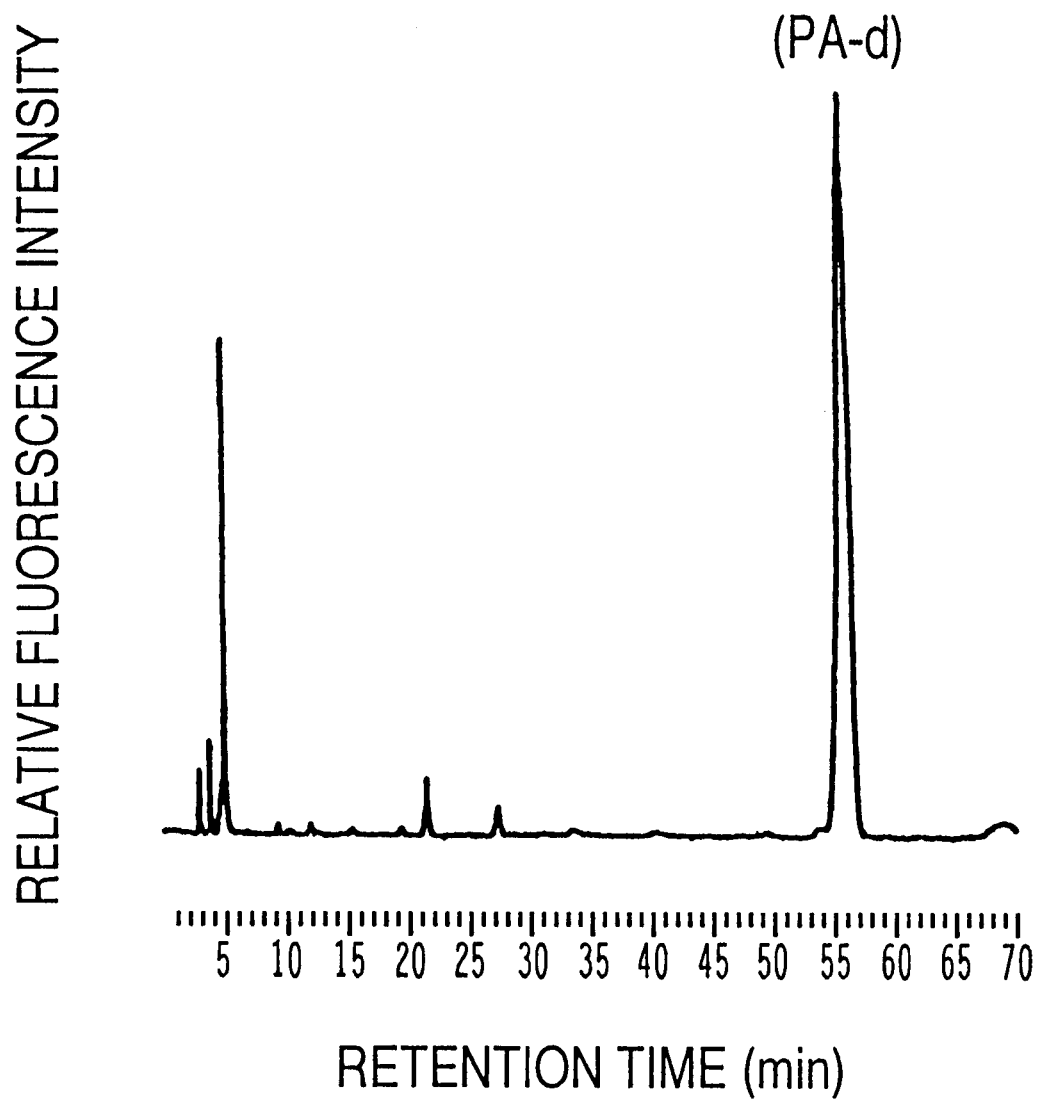
FIG. 4 shows the elution pattern of the sugar compound (d) having been pyridyl-(2)-aminated (PA-d) which is eluted from an L-column.
Figure 5:
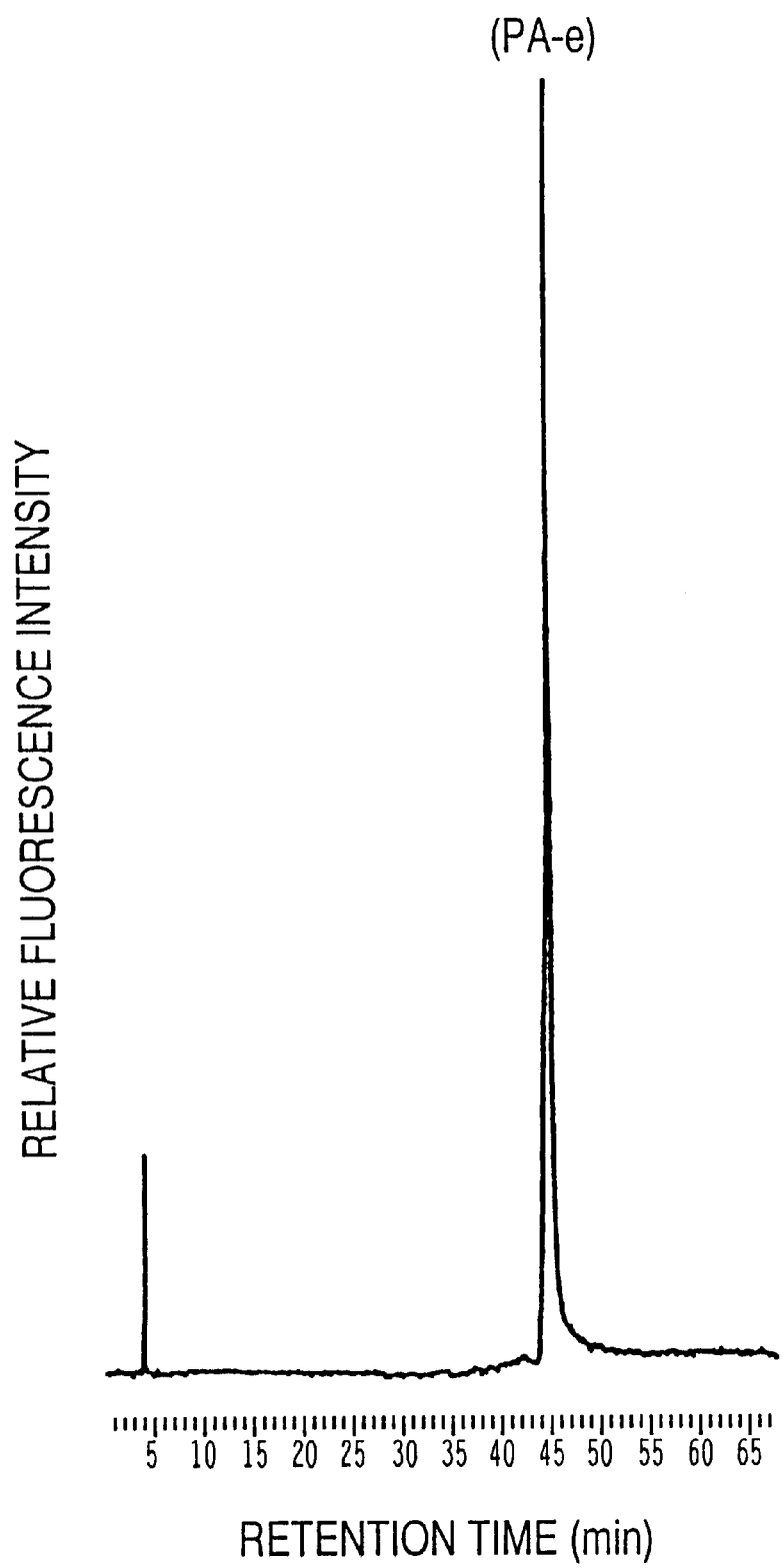
FIG. 5 shows the elution pattern of the sugar compound (e) having been pyridyl-(2)-aminated (PA-e) which is eluted from an L-column.
Figure 6:
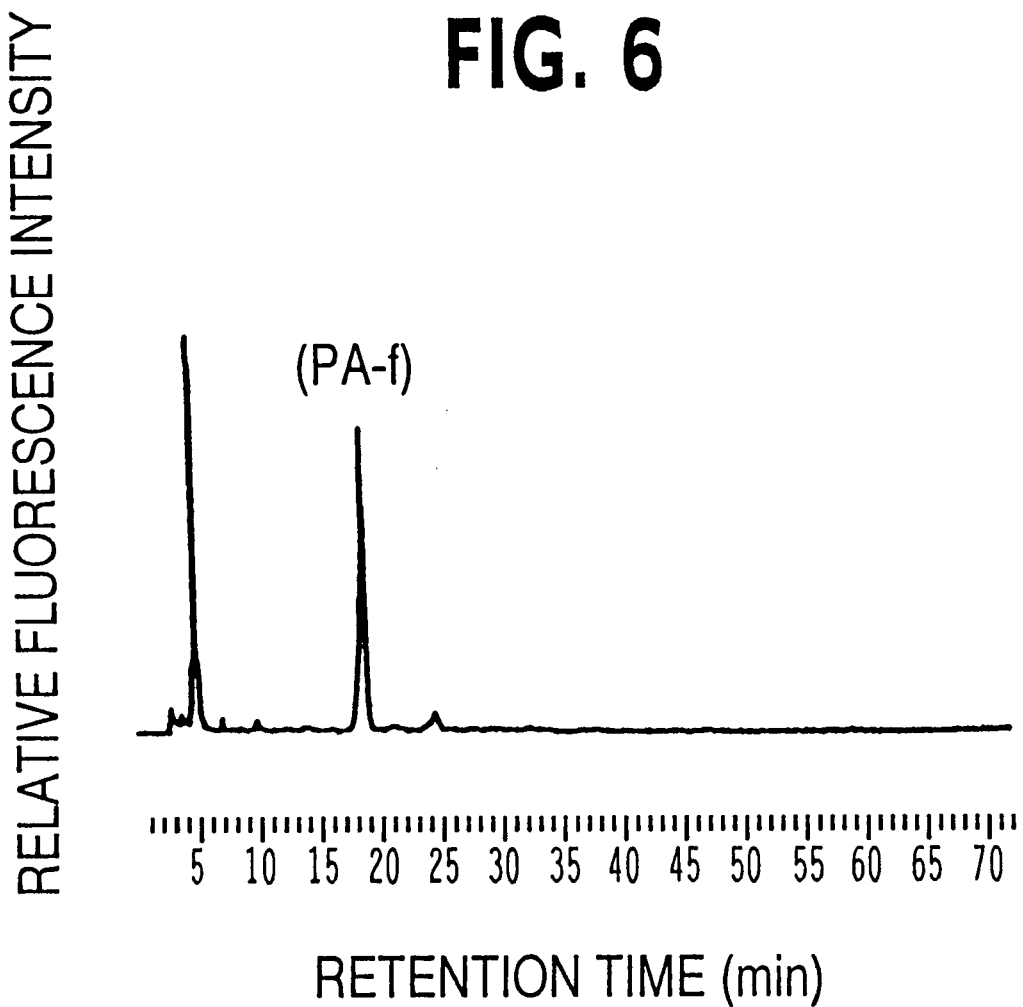
FIG. 6 shows the elution pattern of the sugar compound (f) having been pyridyl-(2)-aminated (PA-f) which is eluted from an L-column.
Figure 7:
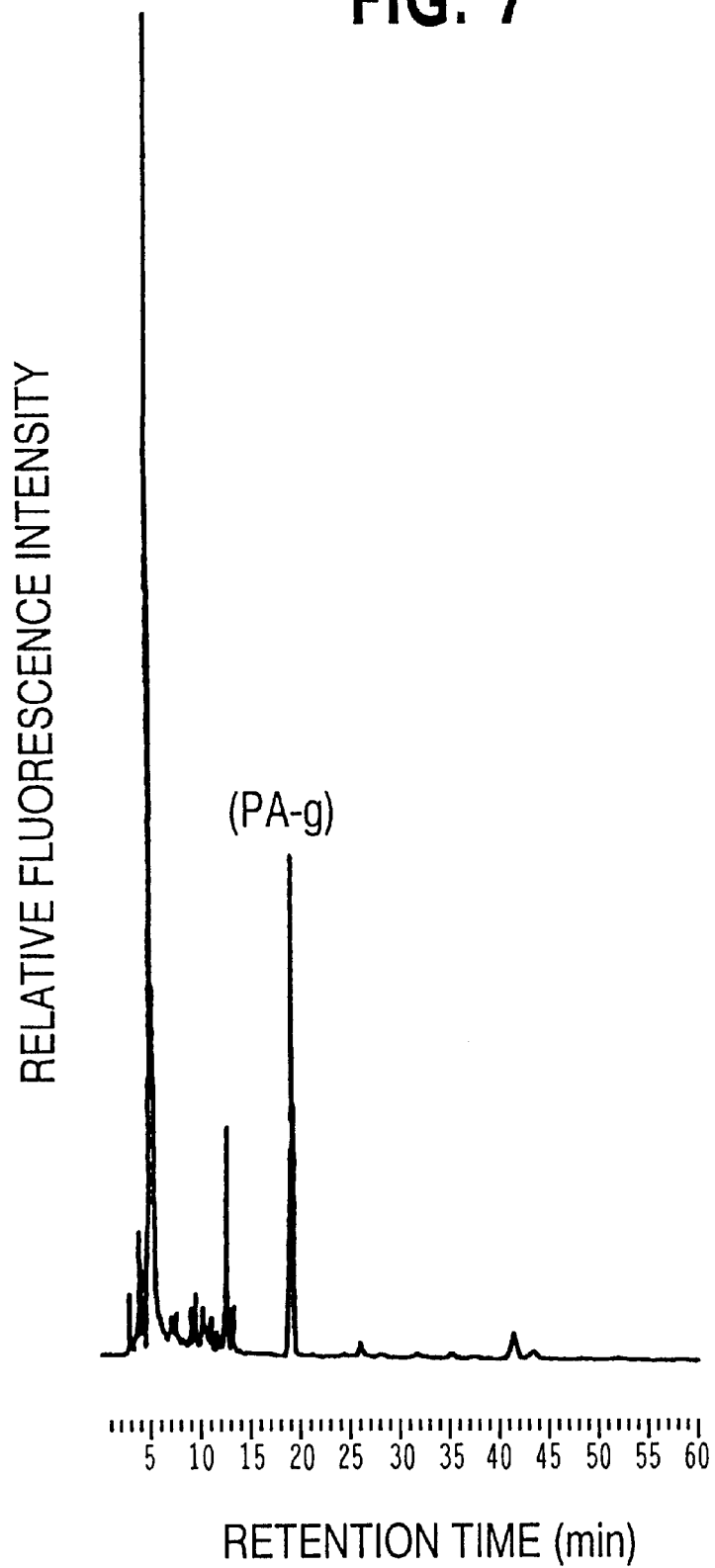
FIG. 7 shows the elution pattern of the sugar compound (g) having been pyridyl-(2)-aminated (PA-g) which is eluted from an L-column.
Figure 8:
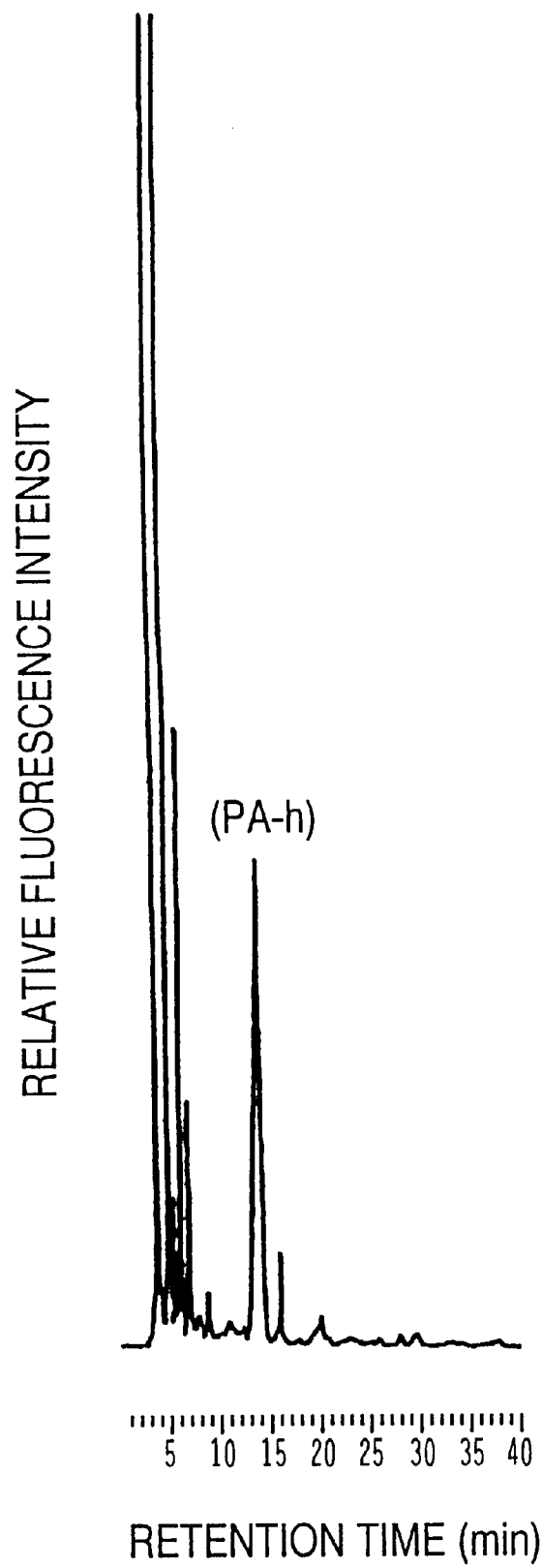
FIG. 8 shows the elution pattern of the sugar compound (h) having been pyridyl-(2)-aminated (PA-h) which is eluted from an L-column.
Figure 9:
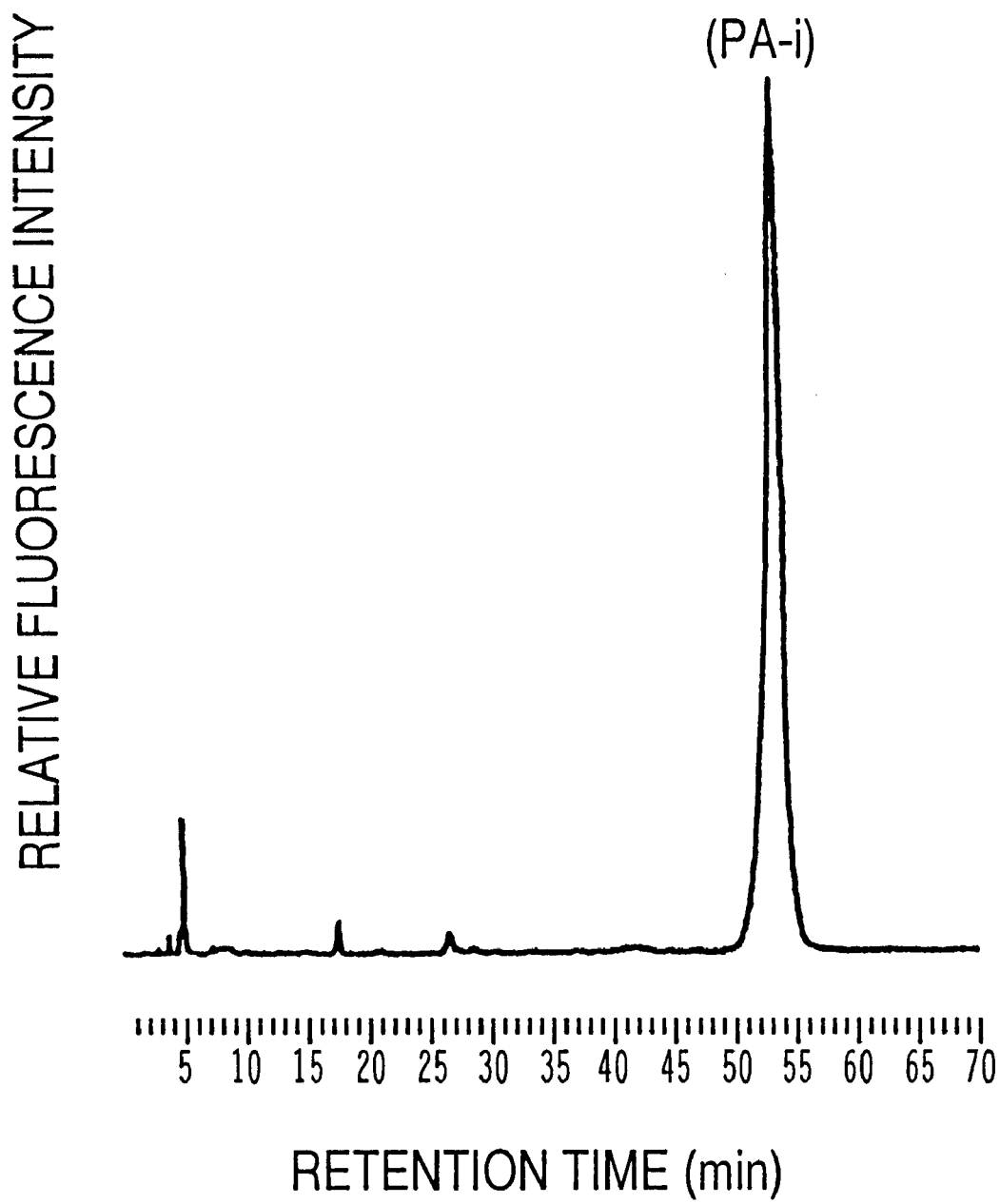
FIG. 9 shows the elution pattern of the sugar compound (i) having been pyridyl-(2)-aminated (PA-i) which is eluted from an L-column.
Figure 10:
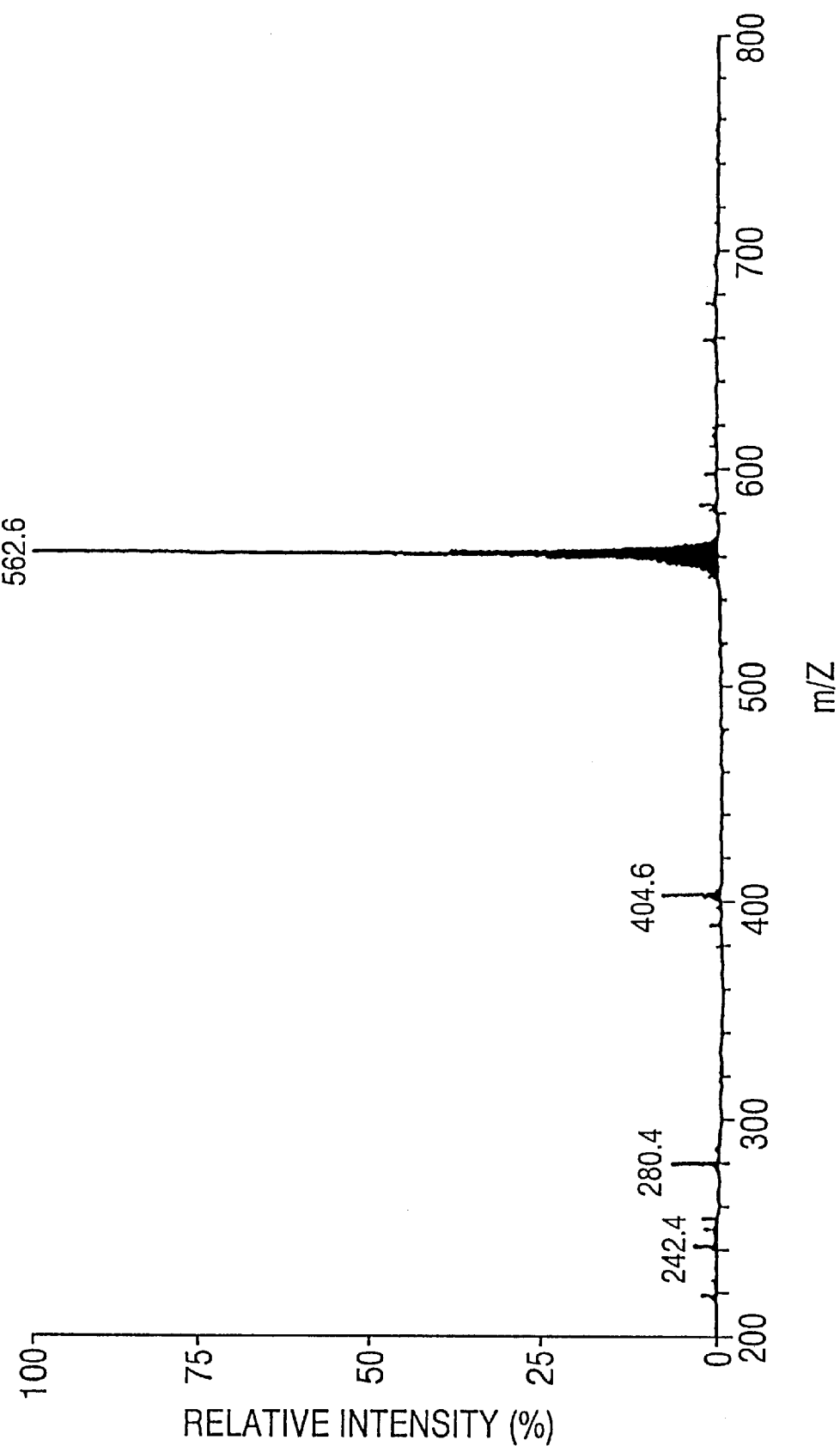
FIG. 10 is the mass spectrogram (negative measurement) of the sugar compound (a).
Figure 11:
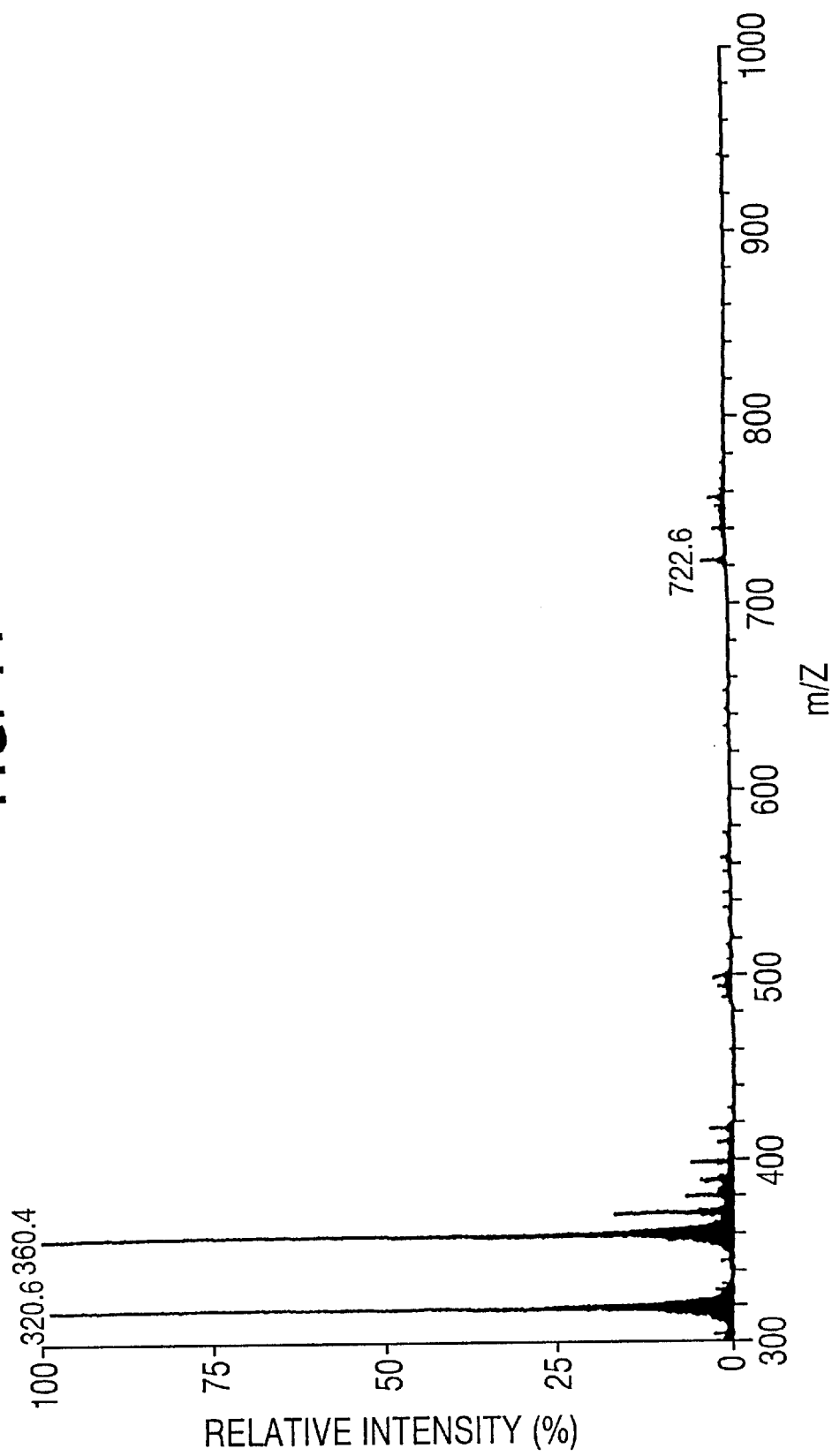
FIG. 11 is the mass spectrogram (negative measurement) of the sugar compound (b).
Figure 12:
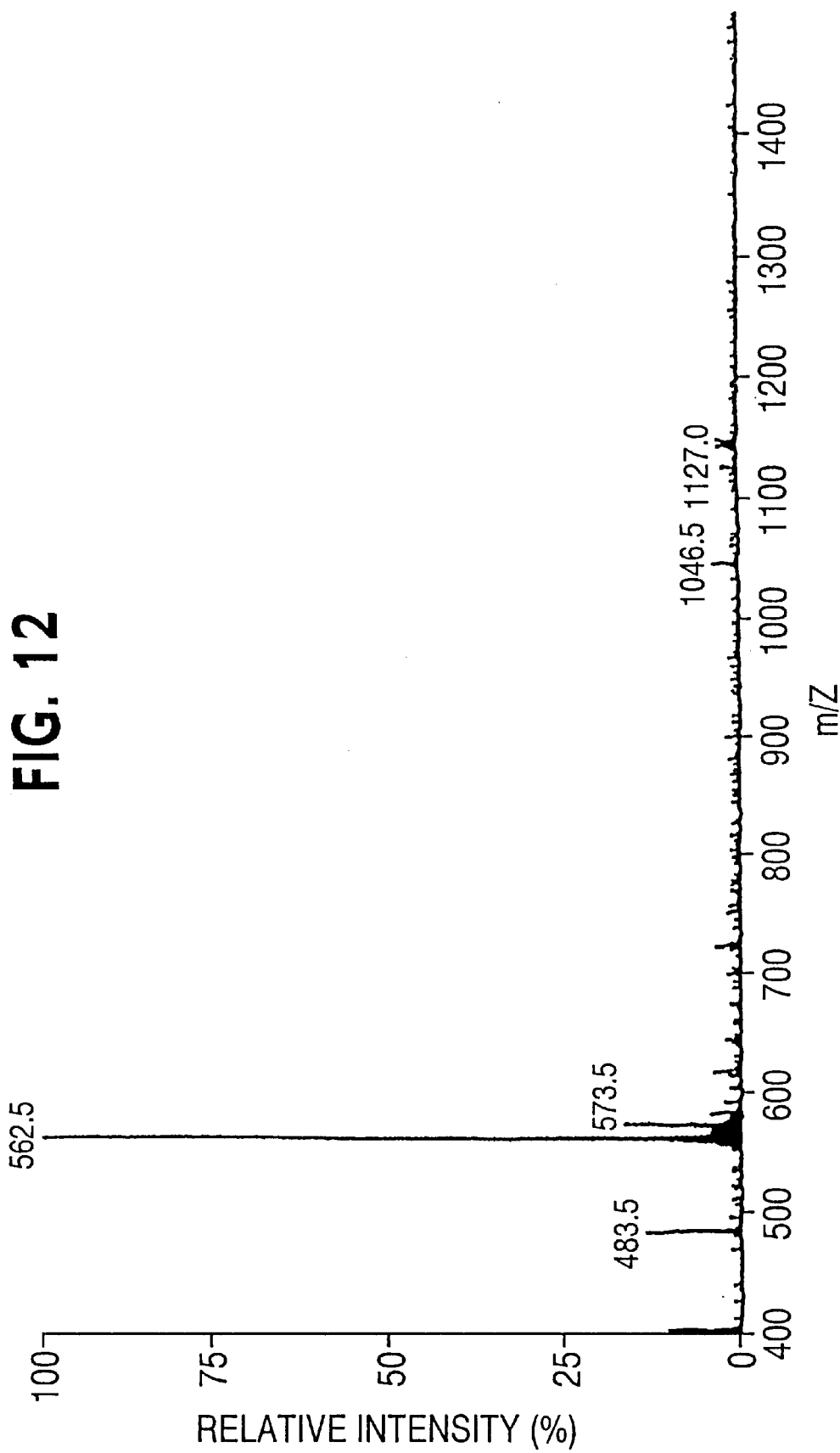
FIG. 12 is the mass spectrogram (negative measurement) of the sugar compound (c).
Figure 13:
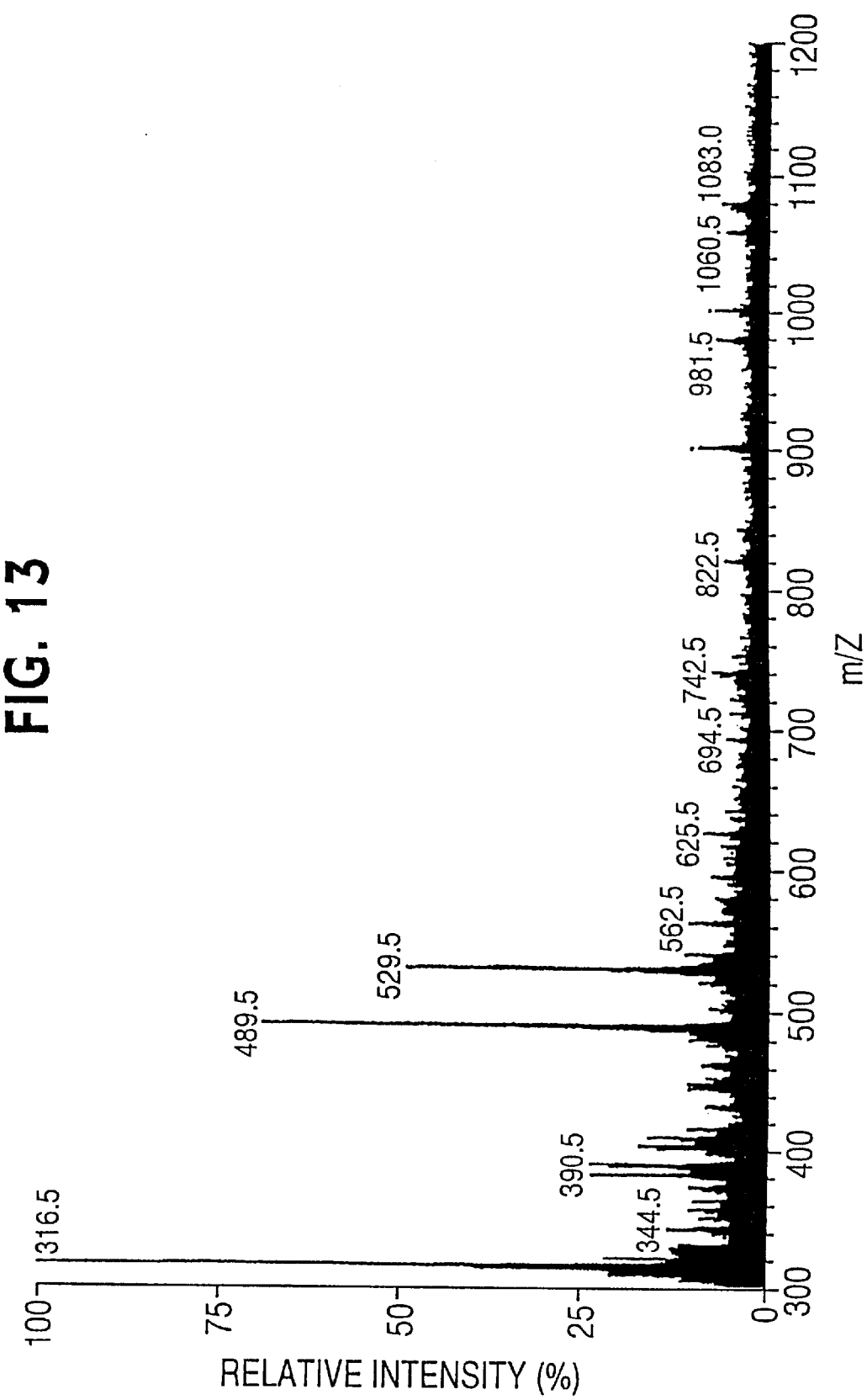
FIG. 13 is the mass spectrogram (negative measurement) of the sugar compound (d).
Figure 14:
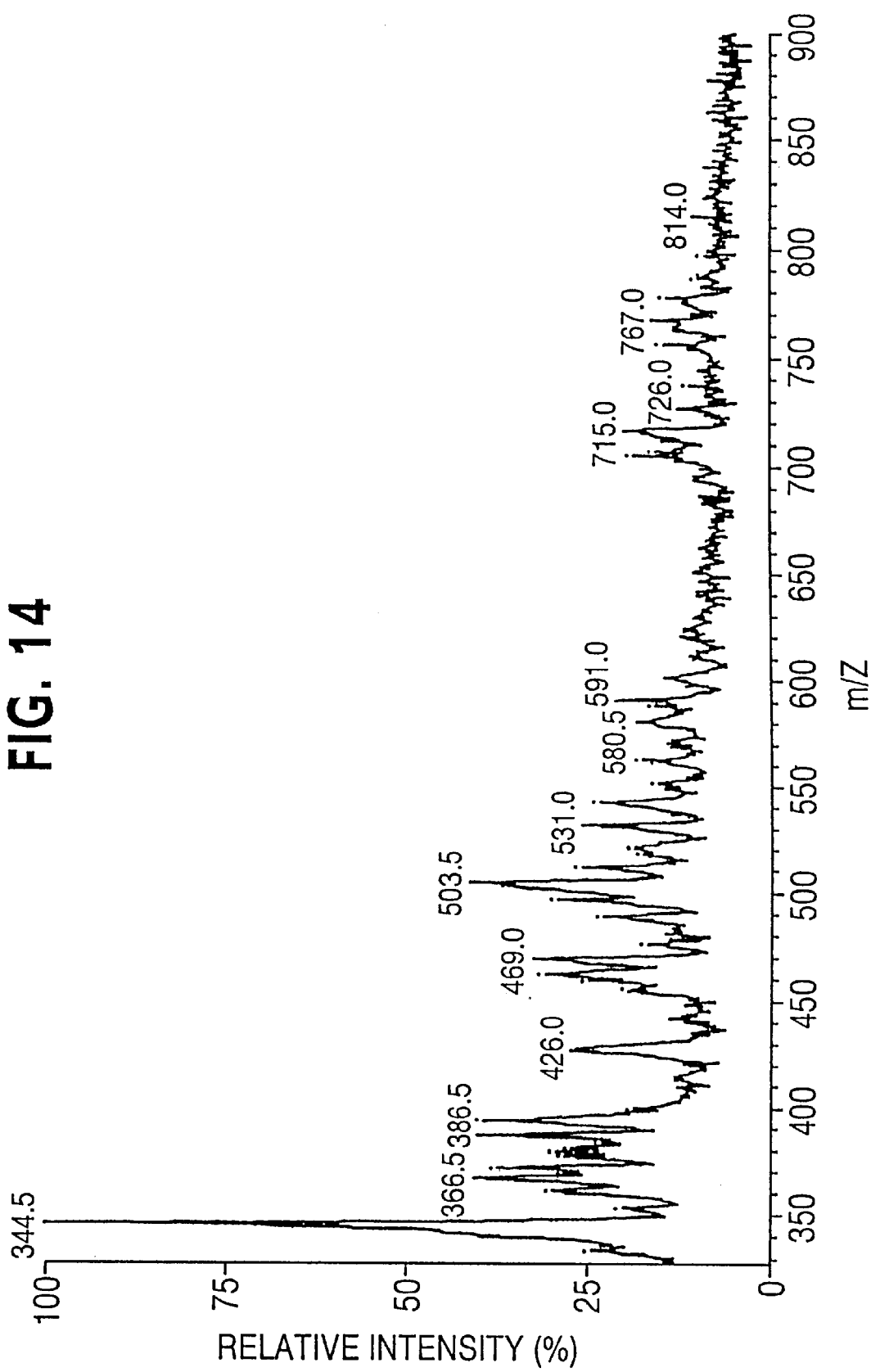
FIG. 14 is the mass spectrogram (negative measurement) of the sugar compound (e).
Figure 15:
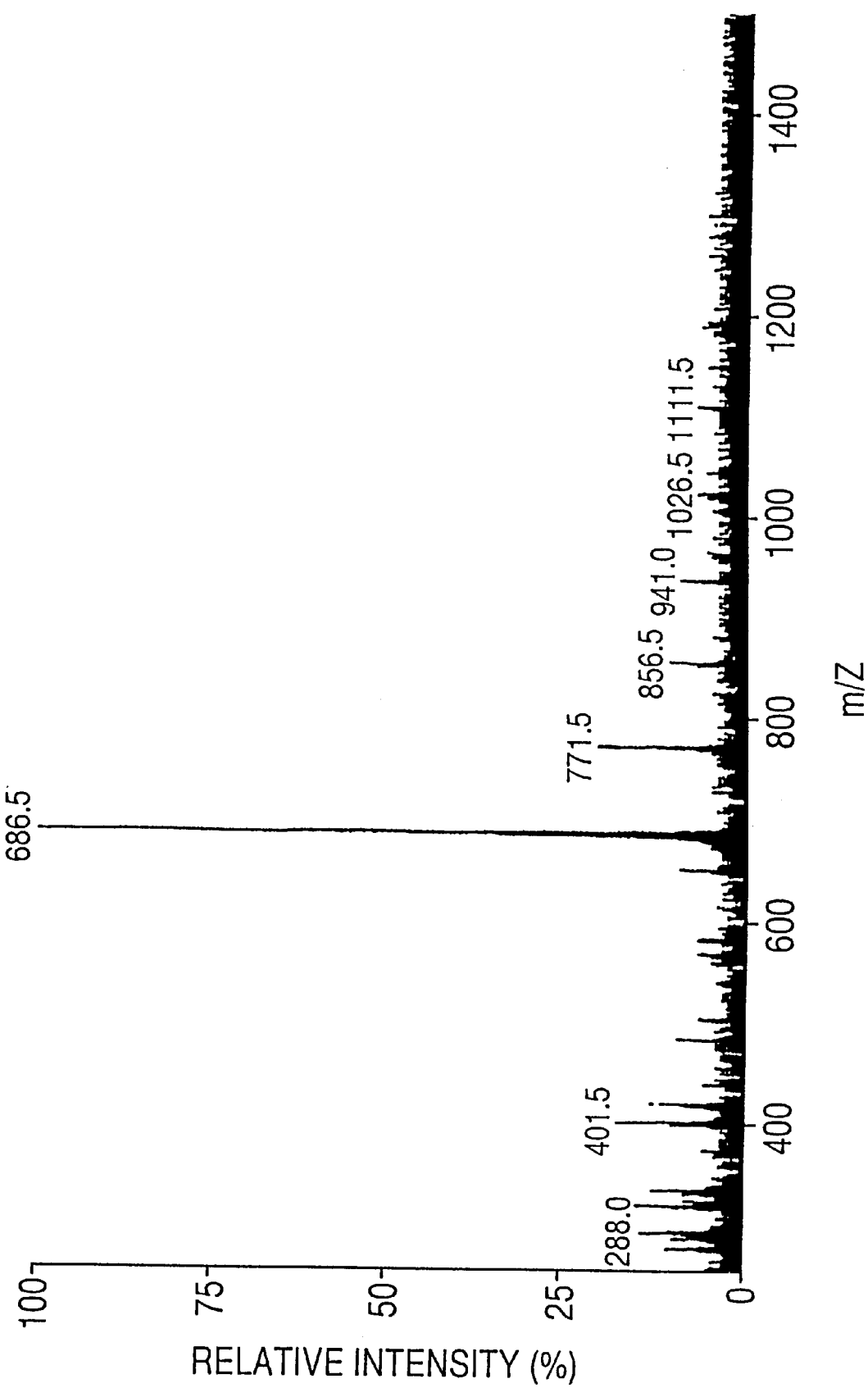
FIG. 15 is the mass spectrogram (negative measurement) of the sugar compound (f).
Figure 16:
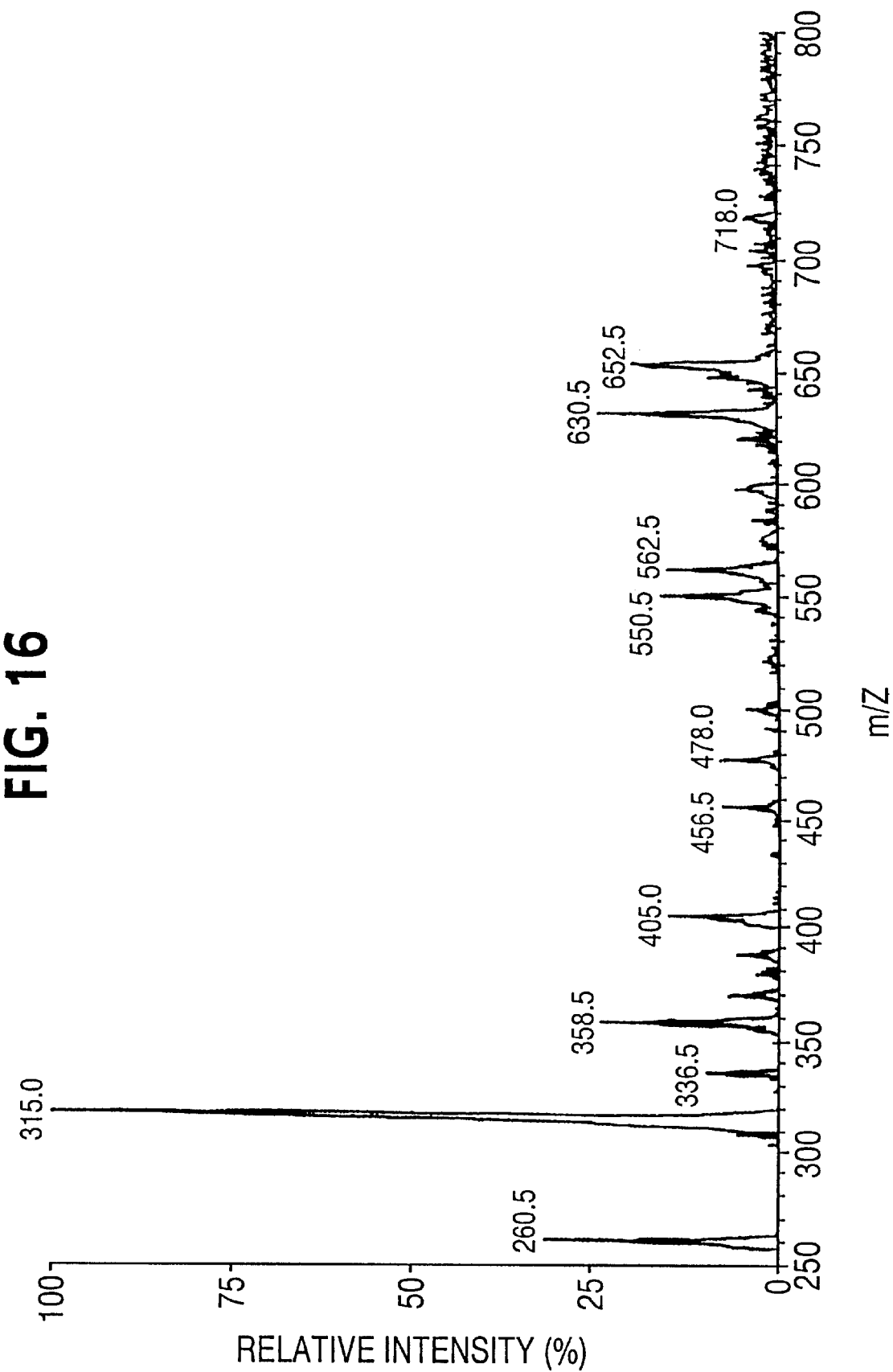
FIG. 16 is the mass spectrogram (negative measurement) of the sugar compound (g).
Figure 17:
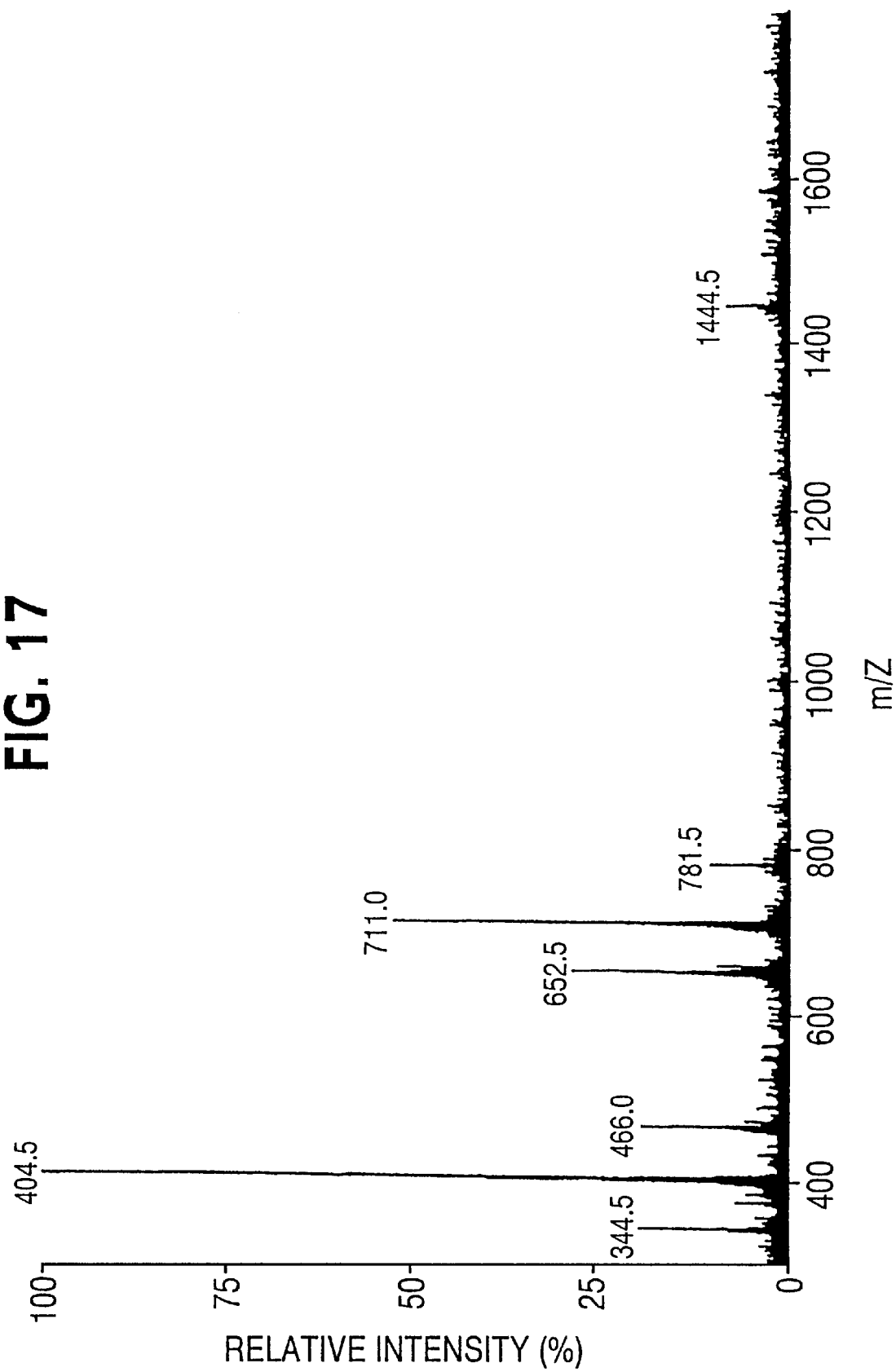
FIG. 17 is the mass spectrogram (negative measurement) of the sugar compound (h).
Figure 18:
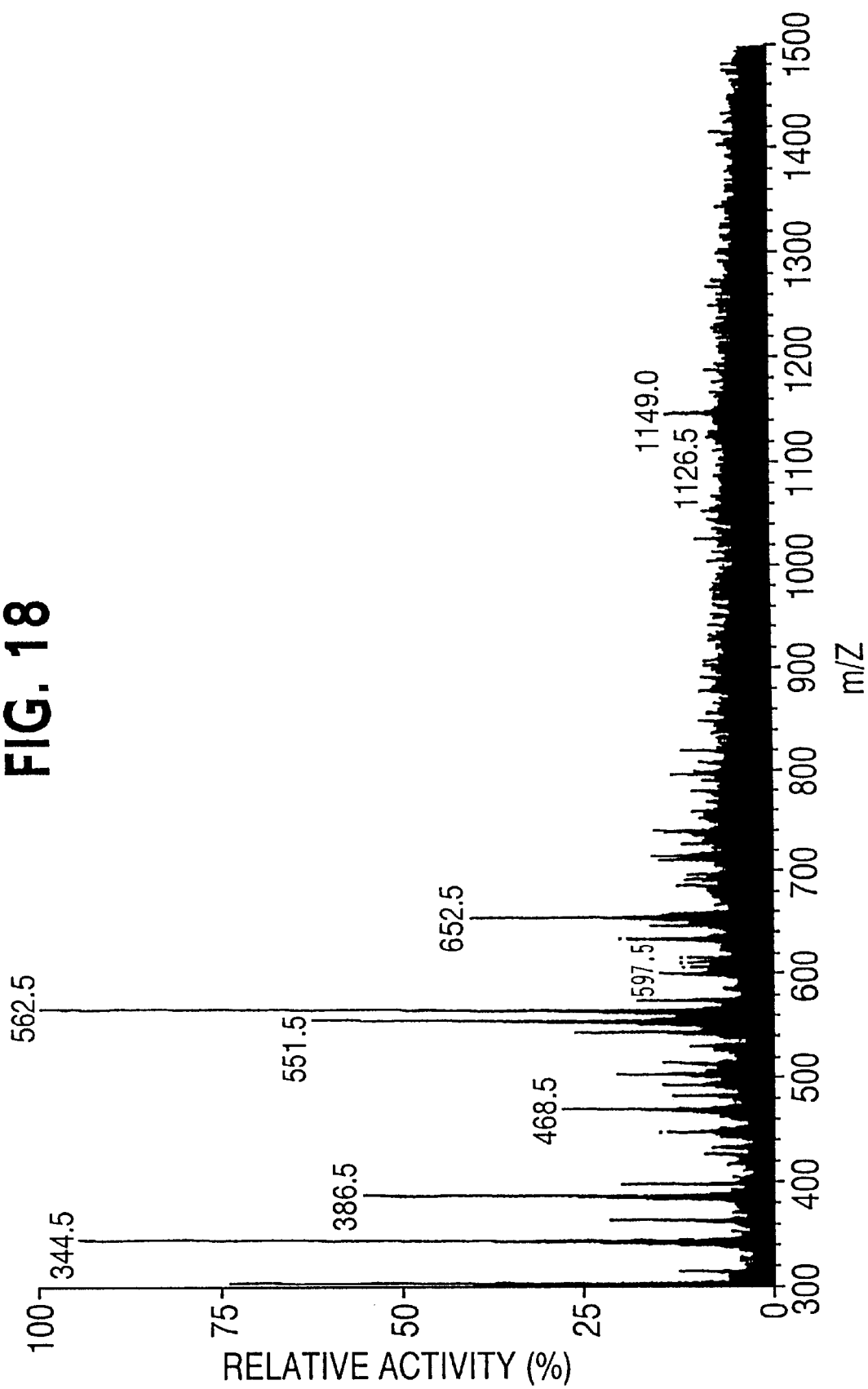
FIG. 18 is the mass spectrogram (negative measurement) of the sugar compound (i).
Figure 19:
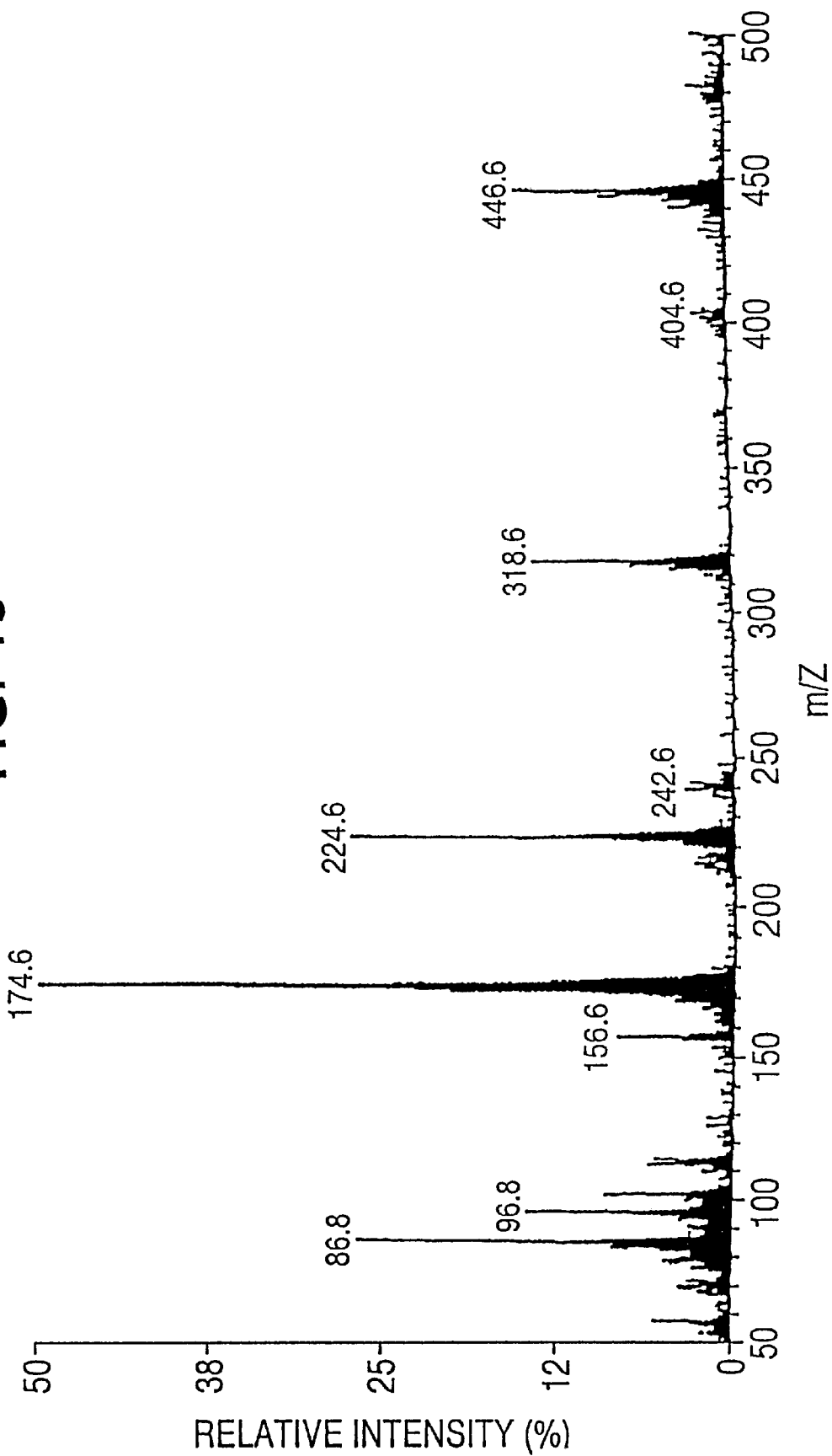
FIG. 19 is the mass-mass spectrogram (negative measurement) of the sugar compound (a).
Figure 20:
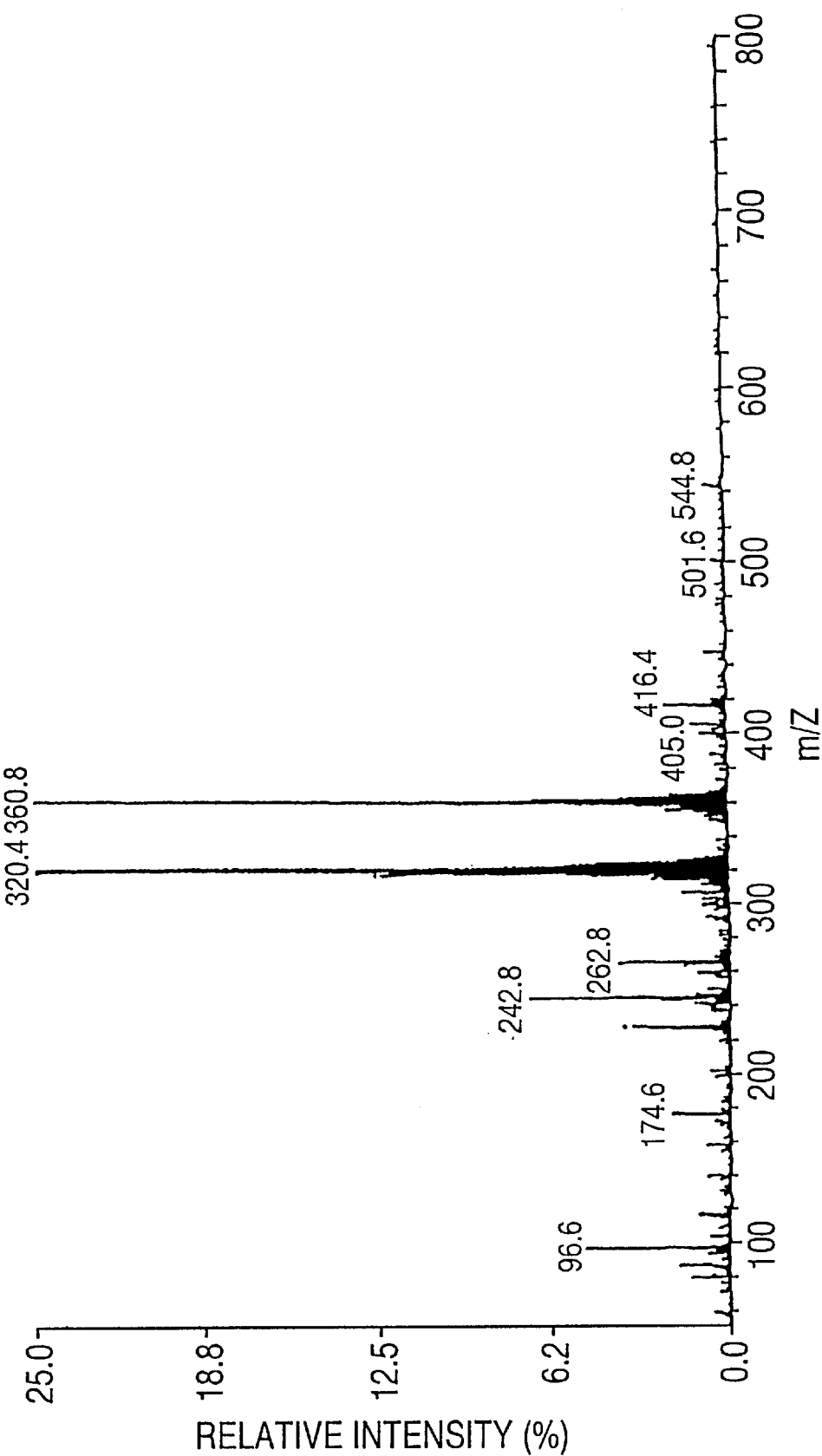
FIG. 20 is the mass-mass spectrogram (negative measurement) of the sugar compound (b).
Figure 21:
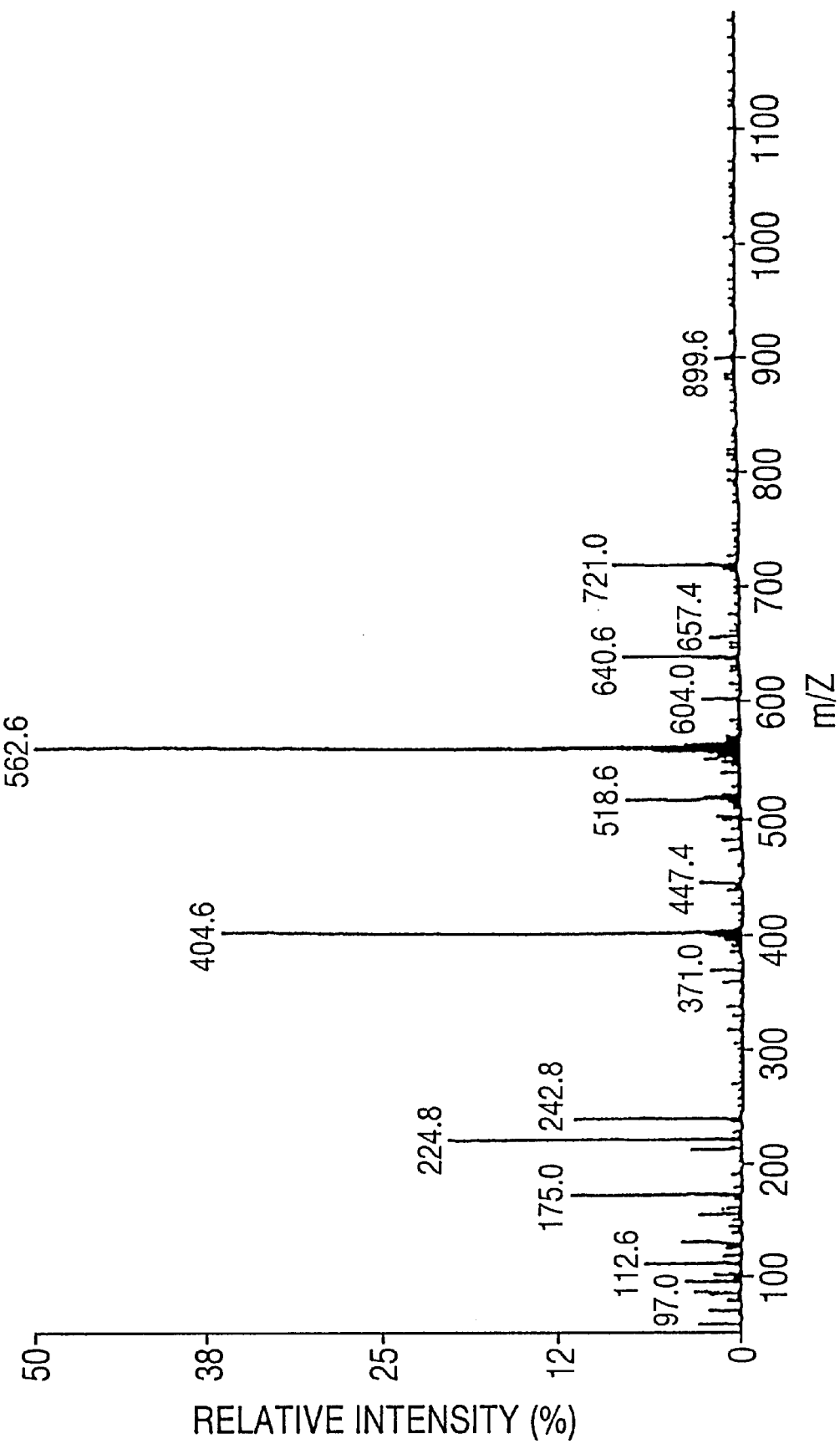
FIG. 21 is the mass-mass spectrogram (negative measurement) of the sugar compound (c).
Figure 22:
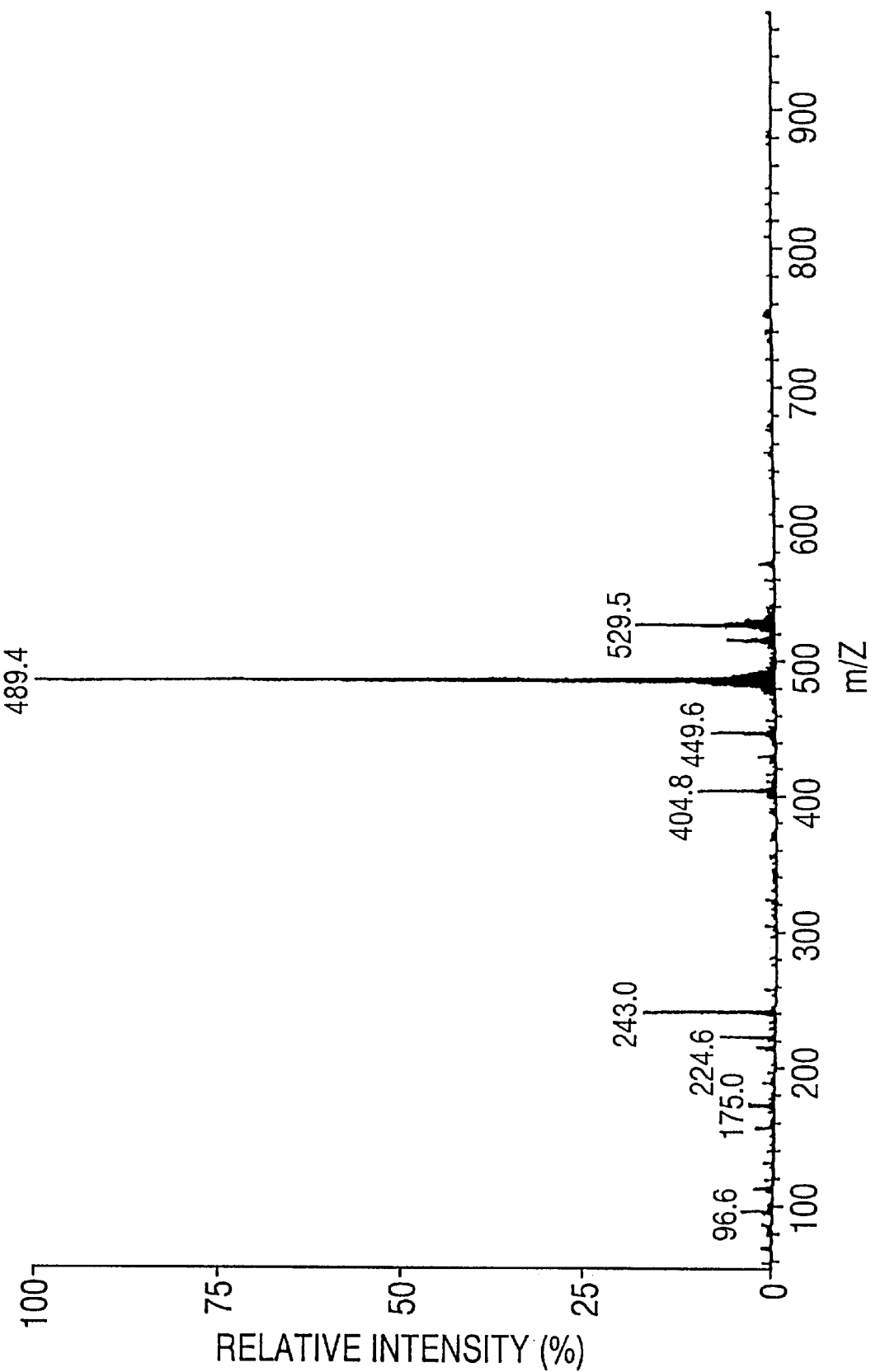
FIG. 22 is the mass-mass spectrogram (negative measurement) of the sugar compound (d).
Figure 23:
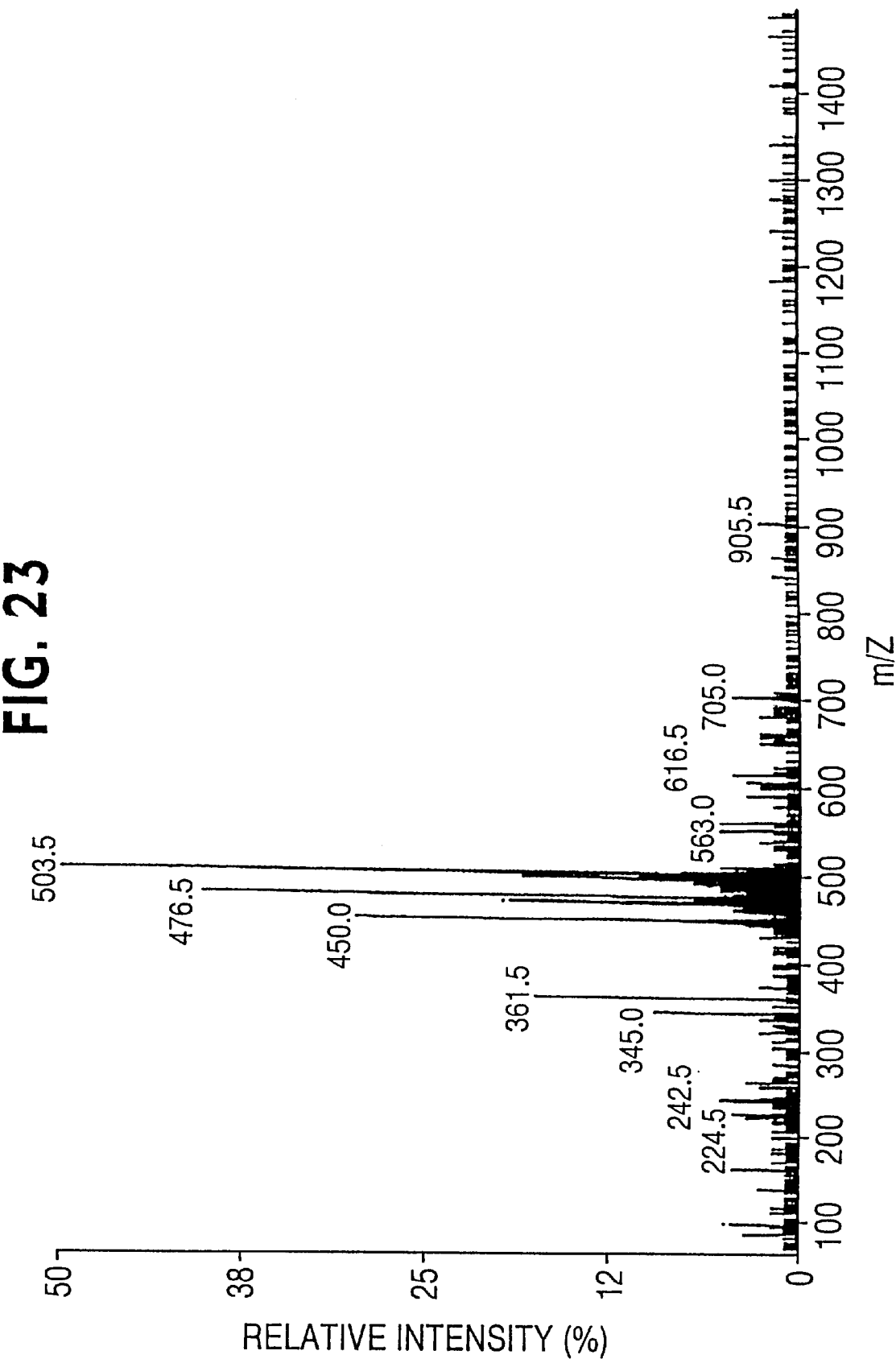
FIG. 23 is the mass-mass spectrogram (negative measurement) of the sugar compound (e).
Figure 24:
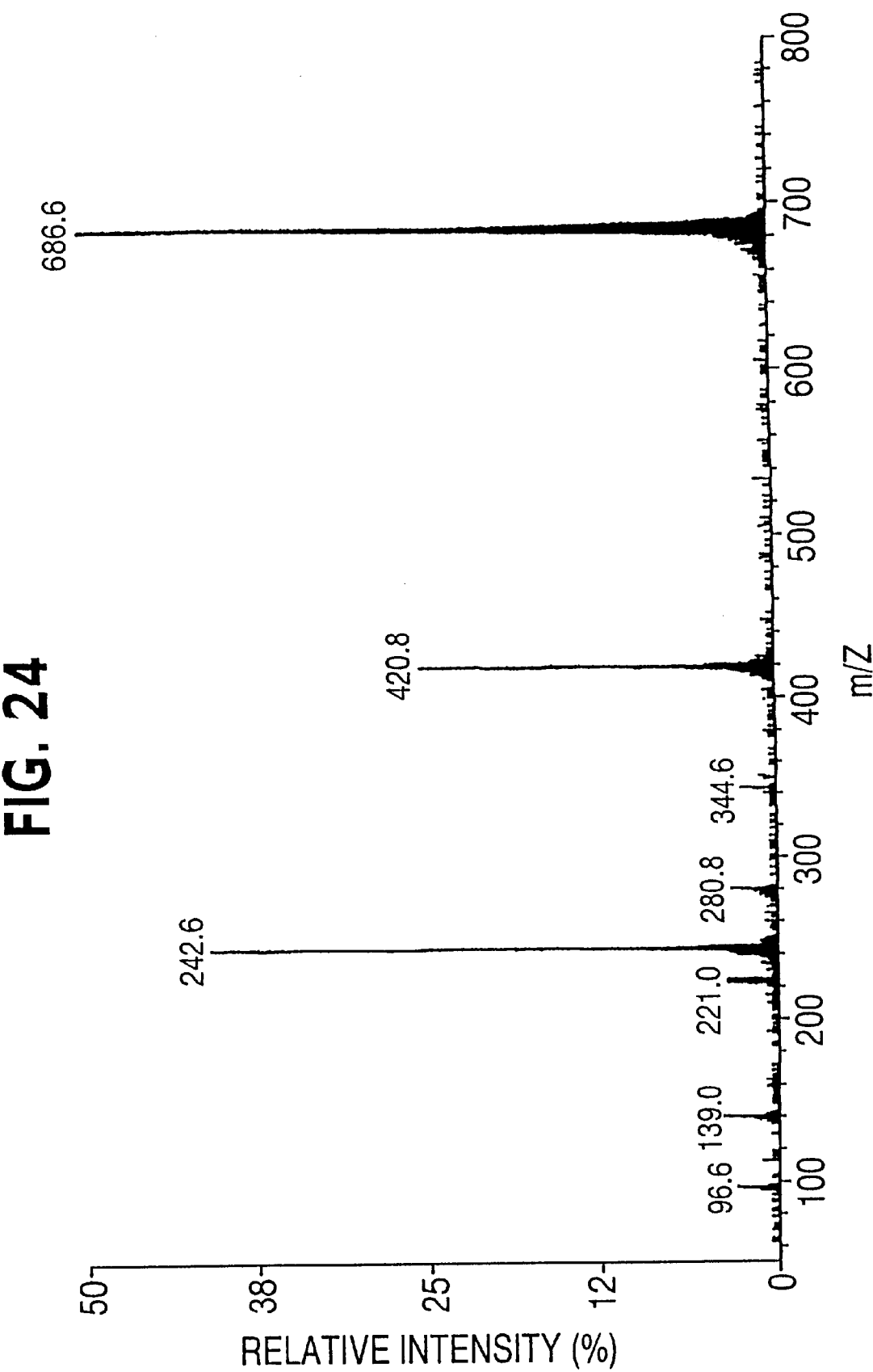
FIG. 24 is the mass-mass spectrogram (negative measurement) of the sugar compound (f).
Figure 25:
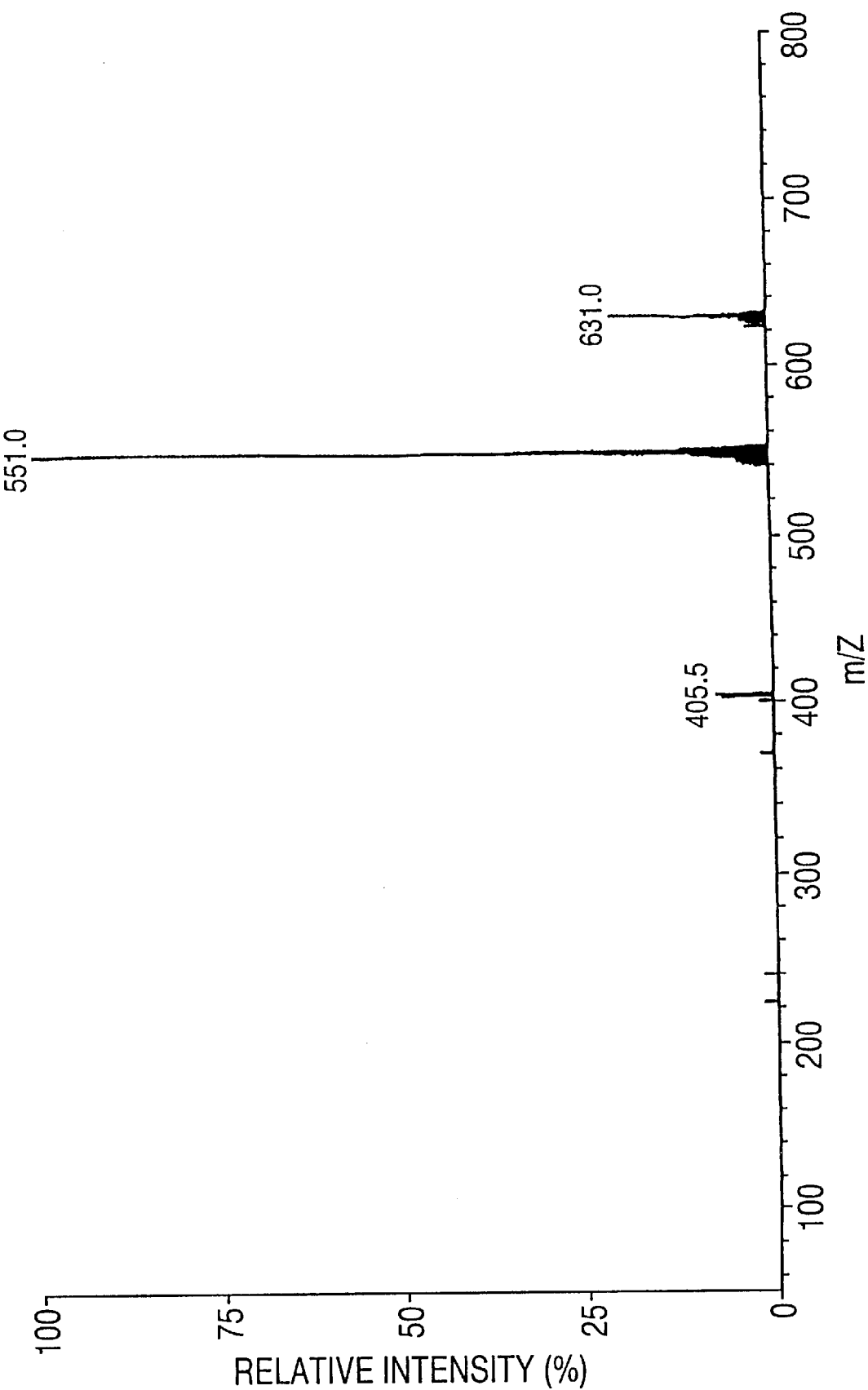
FIG. 25 is the mass-mass spectrogram (negative measurement) of the sugar compound (g).
Figure 26:
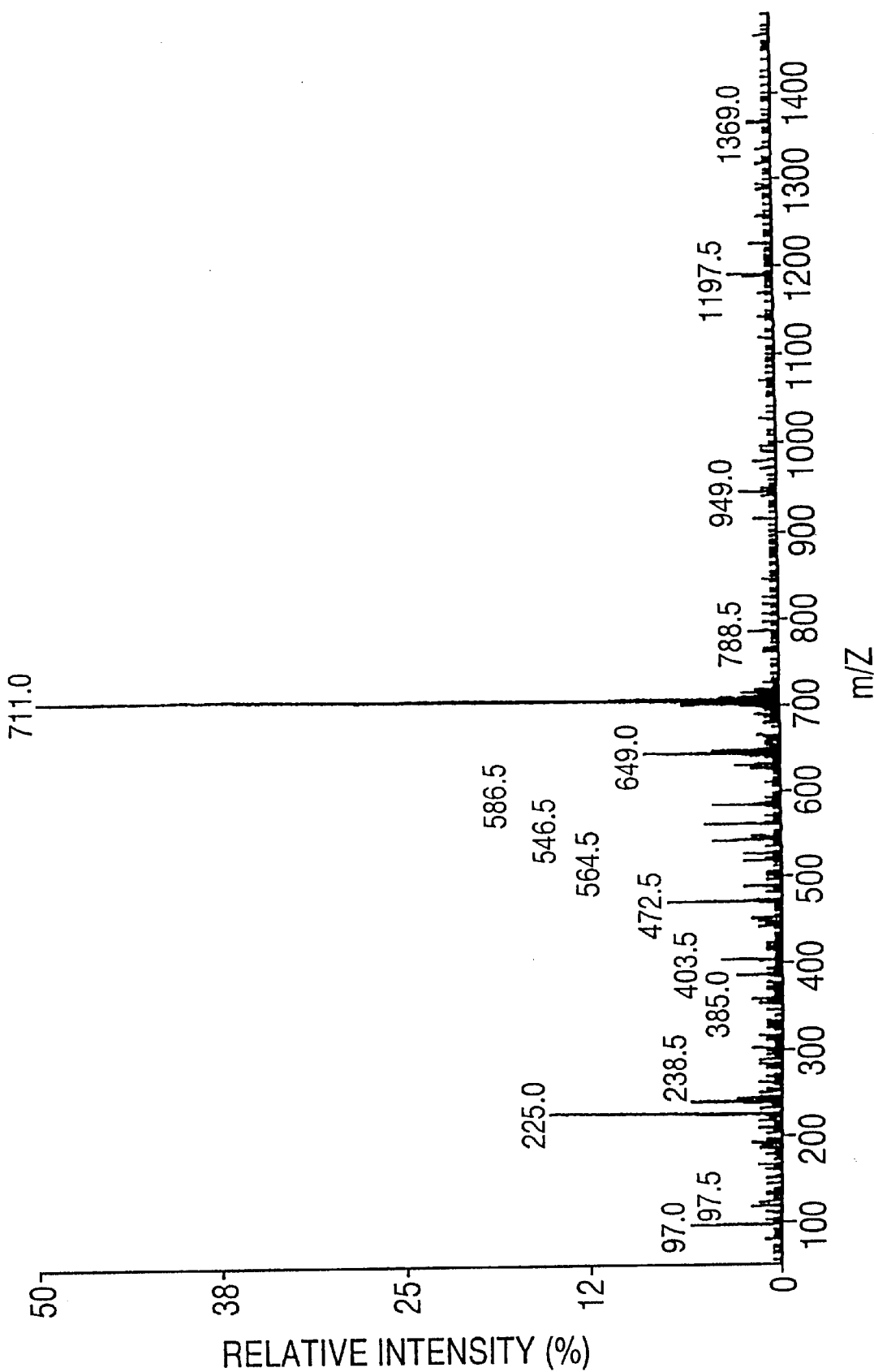
FIG. 26 is the mass-mass spectrogram (negative measurement) of the sugar compound (h).
Figure 27:
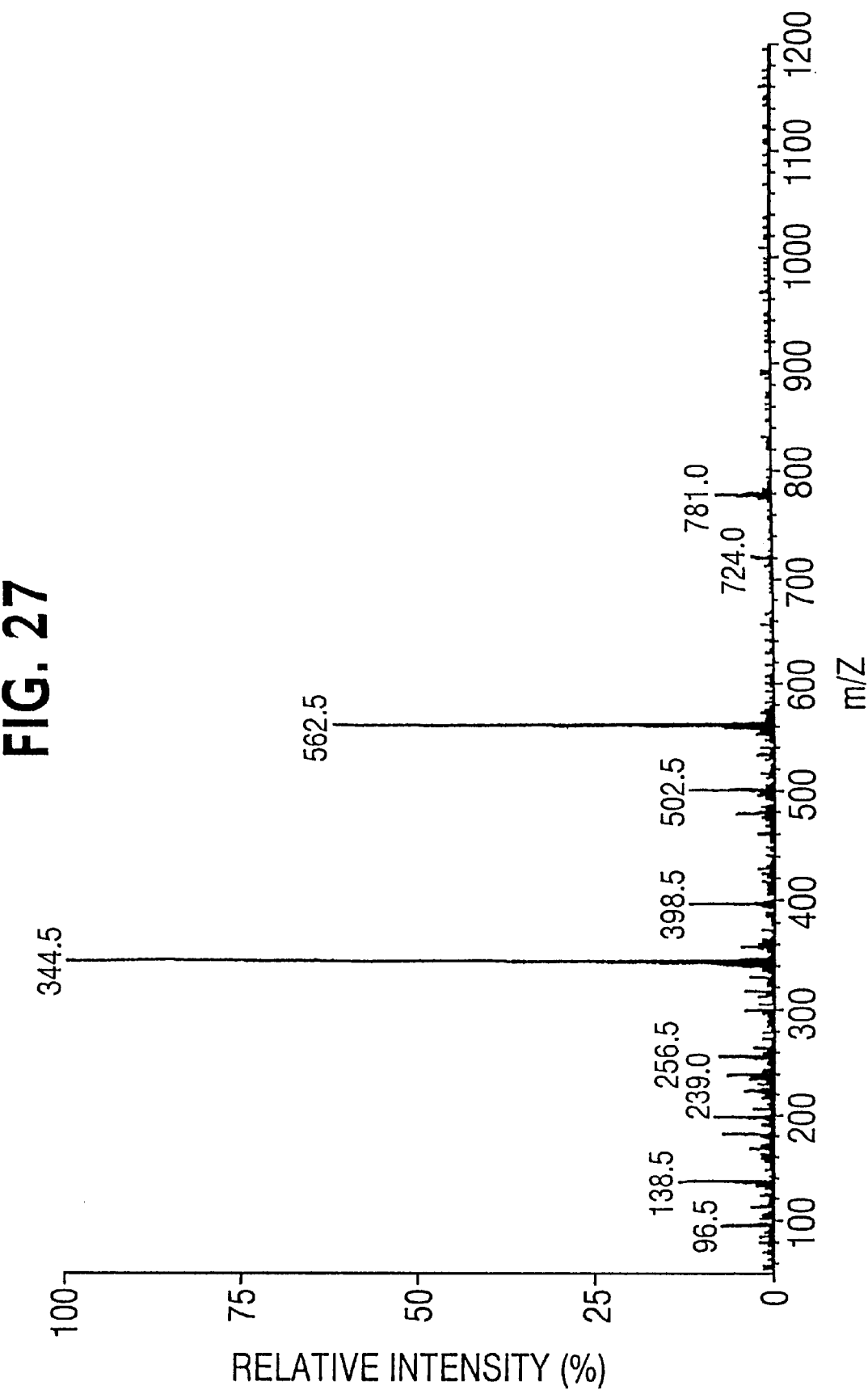
FIG. 27 is the mass-mass spectrogram (negative measurement) of the sugar compound (i).
Figure 28:
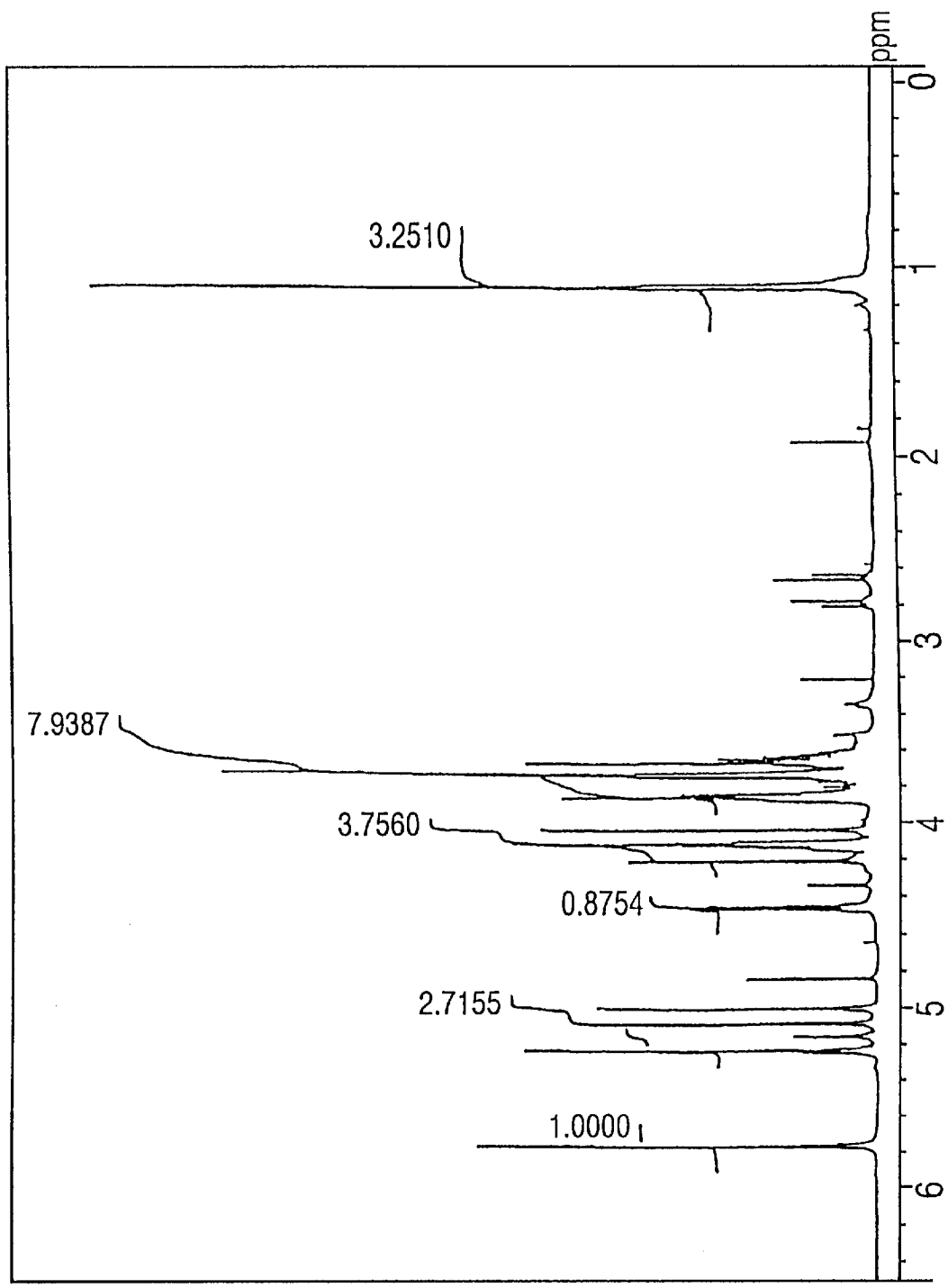
FIG. 28 is the H-NMR spectrum of the sugar compound (a).
Figure 29:
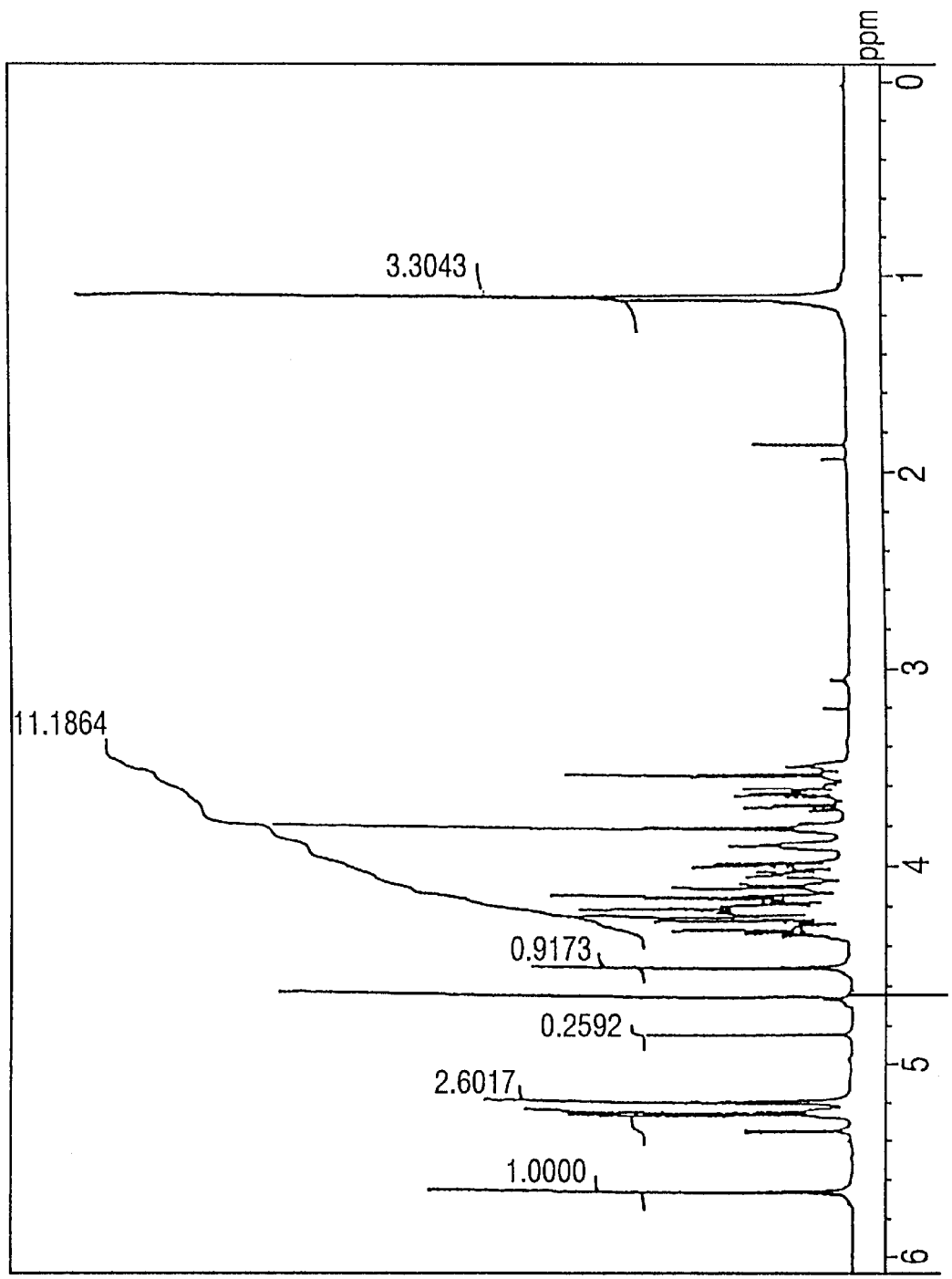
FIG. 29 is the $^1$H-NMR spectrum of the sugar compound (b).
Figure 30:
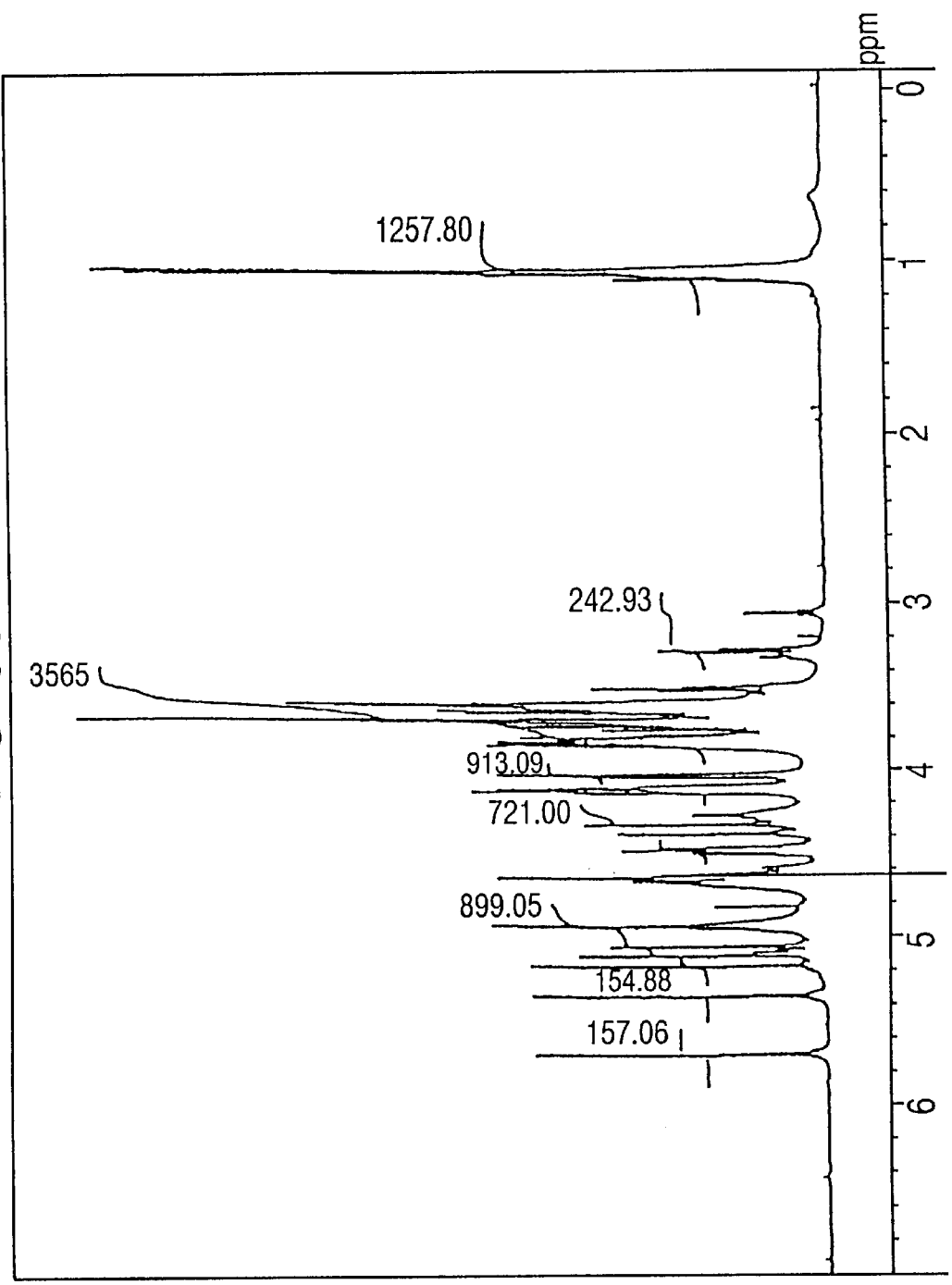
FIG. 30 is the $^1$H-NMR spectrum of the sugar compound (c).
Figure 31:
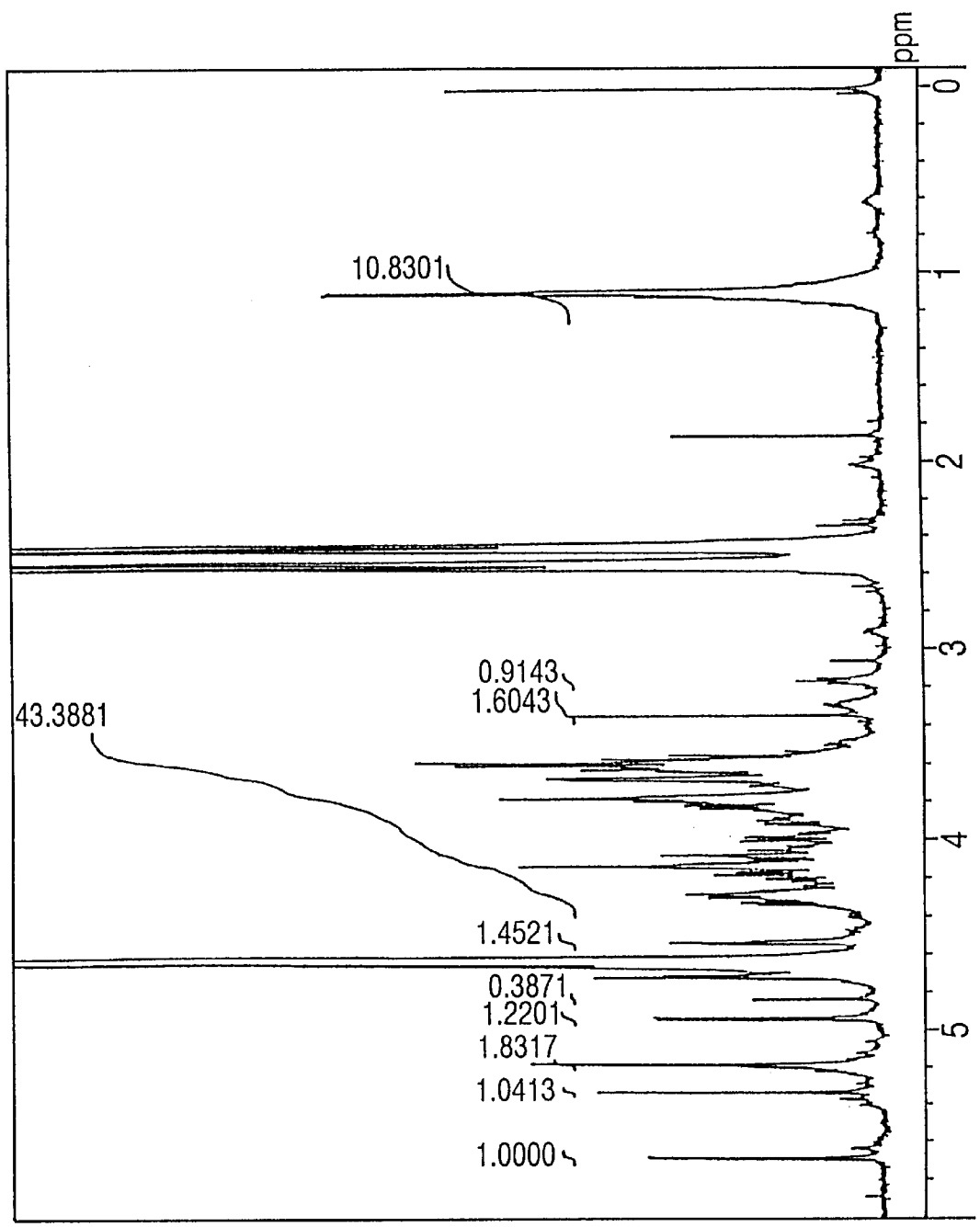
FIG. 31 is the $^1$H-NMR spectrum of the sugar compound (d).
Figure 32:
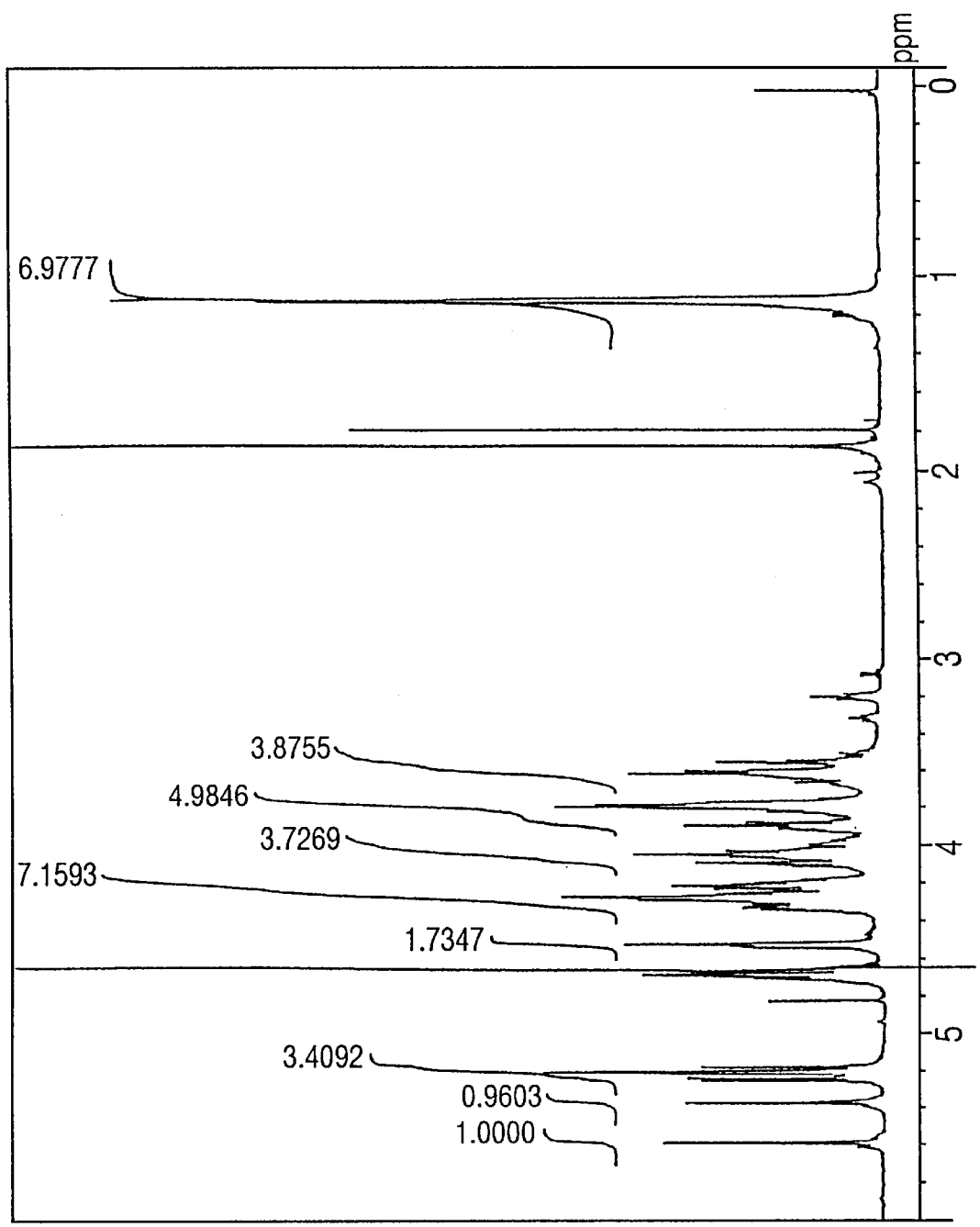
FIG. 32 is the $^1$H-NMR spectrum of the sugar compound (e).
Figure 33:
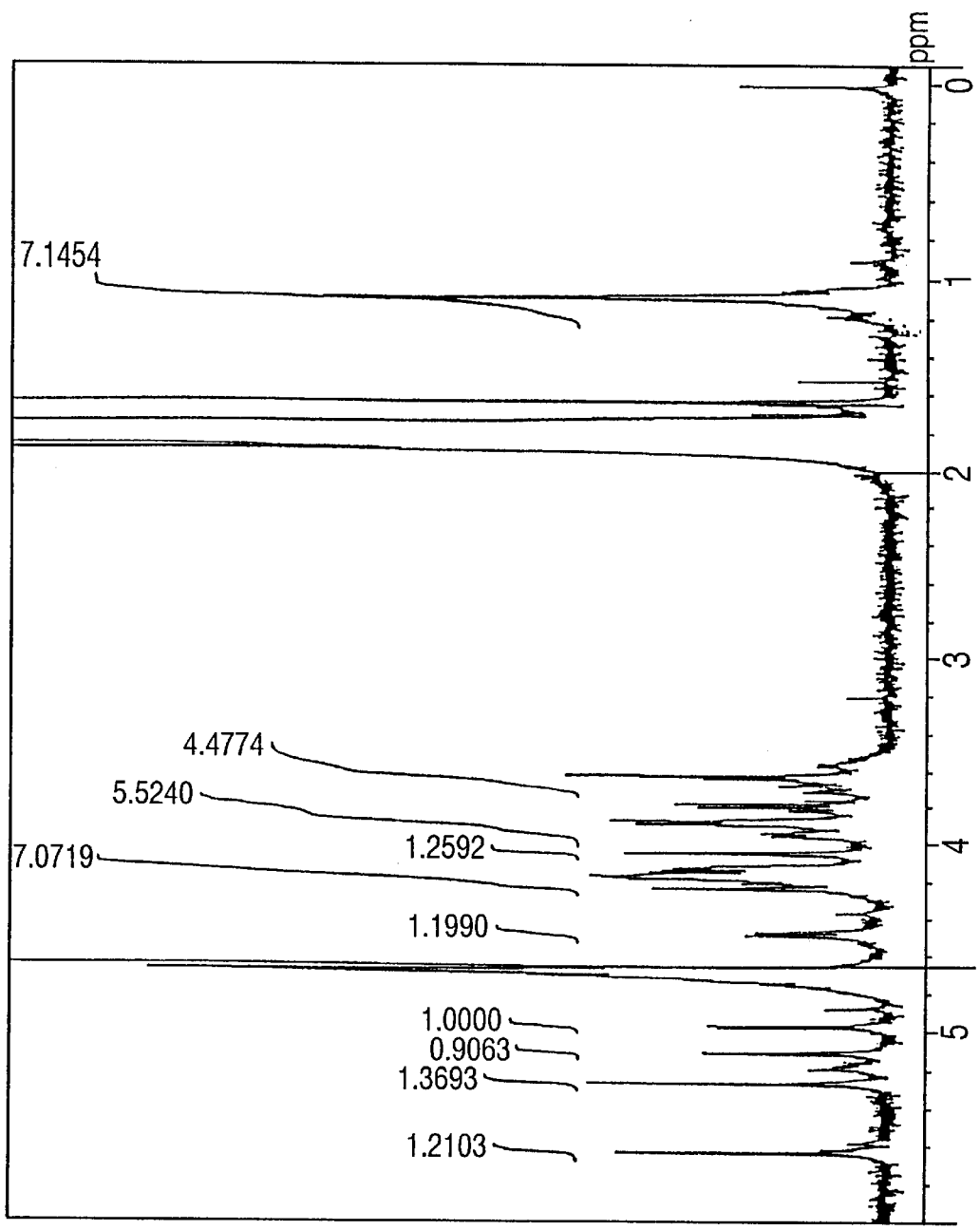
FIG. 33 is the $^1$H-NMR spectrum of the sugar compound (f).
Figure 34:
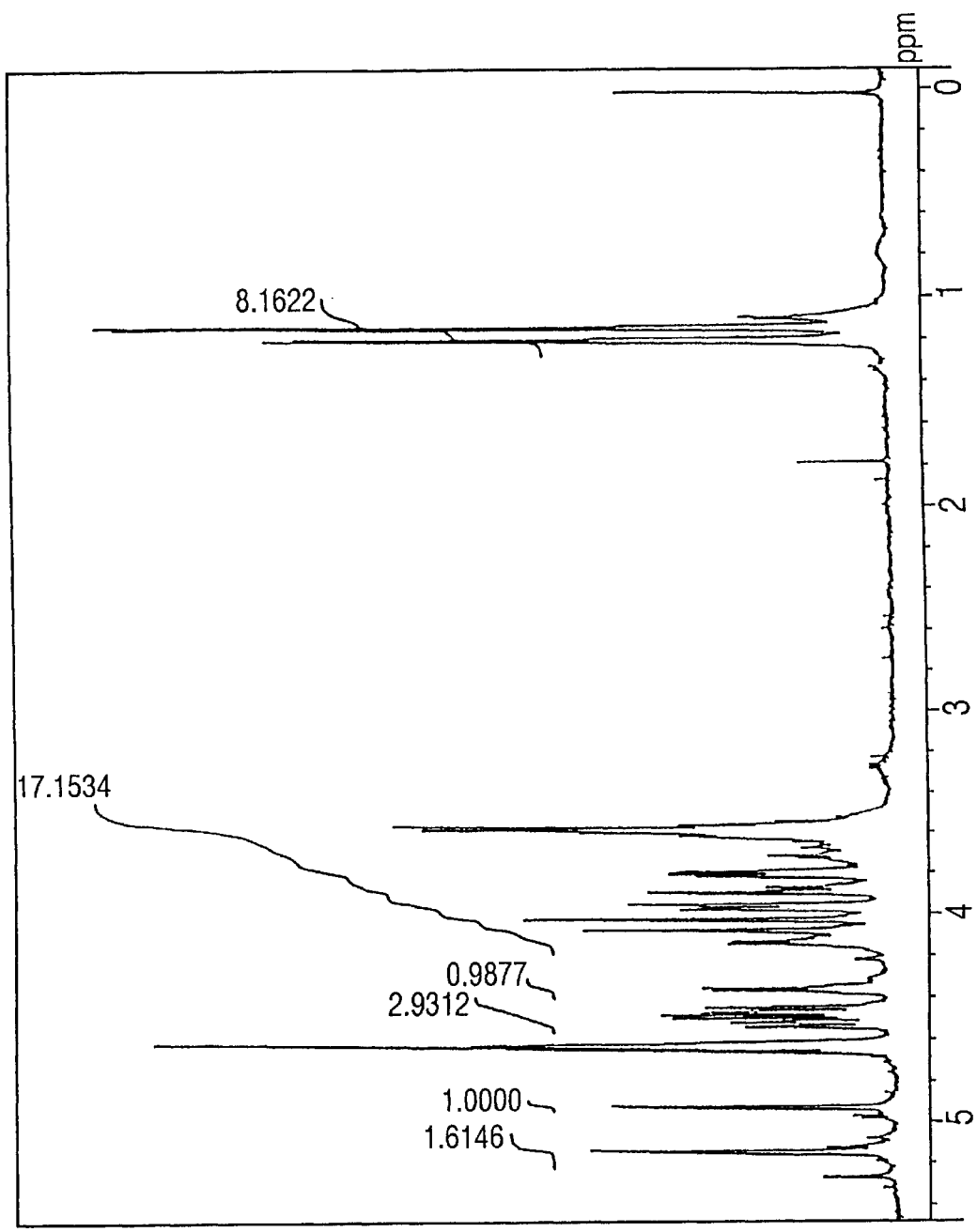
FIG. 34 is the $^1$H-NMR spectrum of the sugar compound (g).
Figure 35:
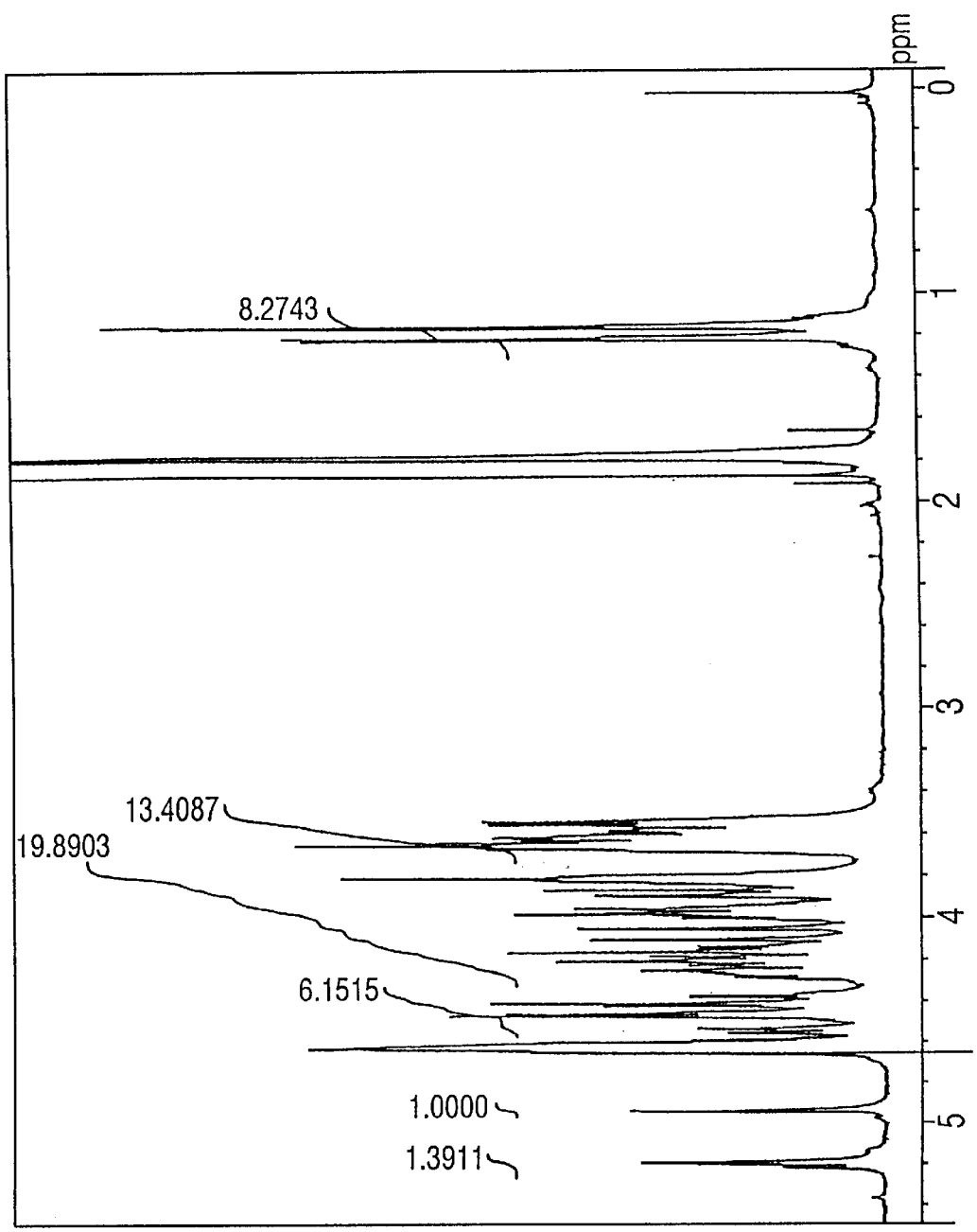
FIG. 35 is the $^1$H-NMR spectrum of the sugar compound (h).
Figure 36:
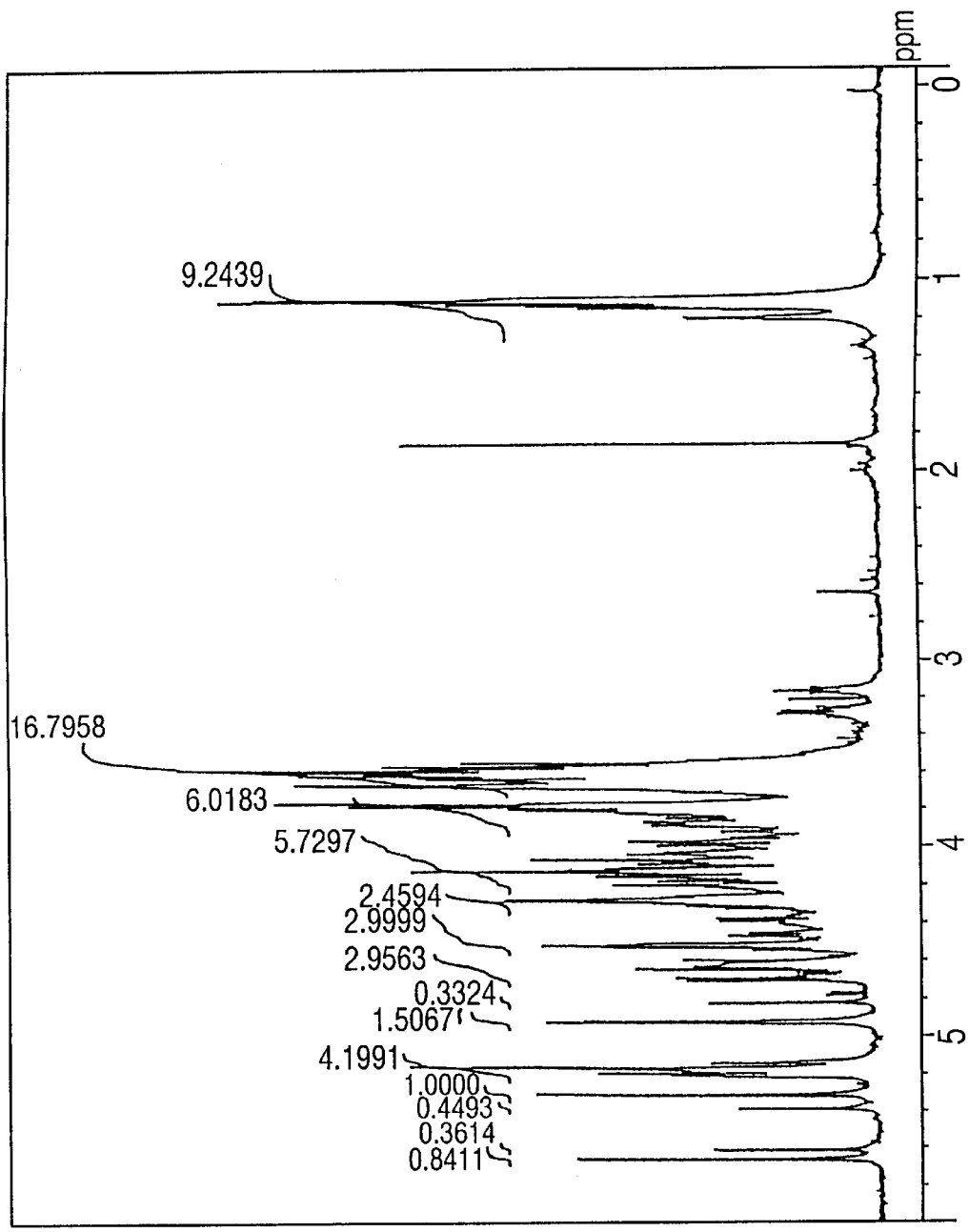
FIG. 36 is the $^1$H-NMR spectrum of the sugar compound (i).

Now, the present invention will be described in greater detail.

The strain to be used in the second invention of the present invention may be an arbitrary one, so long as it belongs to the genus Flavobacterium and is capable of producing the endo-fucoidan-lyase of the present invention. As a particular example of the strain capable of producing the endo-fucoidan-lyase, citation can be made of Flavobacterium sp. SA-0082 strain. The sugar compounds of the first invention of the present invention can be obtained by treating fucoidan with the endo-fucoidan-lyase originating in this strain.

This strain, which has been found out for the first time by the present inventors from seawater in Aomori, has the following mycological properties.

1. Flavobacterium sp. SA-0082 Strain
   a. Morphological properties

| | |
|---|---|
| (1) Short rod; | |
| width | : 0.8–1.0 μm |
| length | : 1.0–1.2 μm |
| (2) Spore | : none |
| (3) Gram-staining | : – | b. Physiological properties
(1) Growth temperature range: capable of growing at 37° C. or less, appropriate growth temperature ranging from 15 to 28° C.

| | | | |
|---|---|---|---|
| (2) Attitude to oxygen | : aerobic | | |
| (3) Catalase | : + | | |
| (4) Oxidase | : + | | |
| (5) Urease | : weakly + | | |
| (6) Acid formation | D-glucose | : + | |
| | lactose | : + | |
| | maltose | : + | |
| | D-mannitol | : + | |
| | sucrose | : – | |
| | trehalose | : – | |
| (7) Hydrolysis | starch | : – | |
| | gelatin | : + | |
| | casein | : – | |
| | esculin | : + | |
| (8) Reduction of nitrate | : – | | |
| (9) Indole formation | : – | | |
| (10) Hydrogen sulfide formation | : – | | |
| (11) Solidification of milk | : – | | |
| (12) Sodium requirement | : + | | |
| (13) Salt requirement | | | |
| Growth in NaCl-free medium | : – | | |
| Growth in 1% NaCl medium | : – | | |
| Growth in seawater medium | : + | | |
| (14) Quinone | : menaquinone 6 | | |
| (15) GC content of intracellular DNA: 32% | | | |
| (16) OF-test | : O | | |
| (17) Colony color | : yellow | | |
| (18) Motility | : none | | |
| (19) Gliding | : none. | | |

It may be estimated that this strain is a bacterium analogous to *Flavobacterium aquatile* and *Flavobacterium meningosepticum* described in Bergey's Manual of Systematic Bacteriology, Vol. 1 (1984) and Bergey's Manual of Determinative Bacteriology, Vol. 9 (1994). However, this strain differs from the former in incapable of forming any acid via the metabolism of sucrose, incapable of decomposing casein, capable of decomposing esculin, capable of liquefying gelatin and being positive to urease, and from the latter in incapable of decomposing casein and slowly growing at 37° C. Accordingly, this strain has been identified as a bacterium belonging to the genus Flavobacterium and named Flavobacterium sp. SA-0082.

The above strain is designated as Flavobacterium sp. SA-0082 and has been deposited at National Institute of Bioscience and Human-Technology, Agency of Industrial Science and Technology (address: 1-3, Higashi 1-chome, Tsukuba, Ibaragi, 305 JAPAN) under the accession number FERM P-14872 since Mar. 29, 1995 and deposited at National Institute of Bioscience and Human-Technology as described above under the accession number FERM BP-5402 (transfer to international deposition was requested on Feb. 15, 1996).

The nutrients to be added to the medium for incubating the strain to be used in the second invention of the present invention may be arbitrary ones so long as the strain employed can utilize them so as to produce the endo-fucoidan-lyase of the second invention of the present invention. Appropriate examples of the carbon source include fucoidan, marine alga powder, alginic acid, fucose, glucose, mannitol, glycerol, saccharose, maltose, lactose and starch, while appropriate examples of the nitrogen source include yeast extract, peptone, casamino acids, corn steep liquor, meat extract, defatted soybean, ammonium sulfate and ammonium chloride. The medium may further contain inorganic substances and metal salts such as sodium salts, phosphates, potassium salts, magnesium salts and zinc salts.

This strain also grows well in seawater or artificial seawater containing the above-mentioned nutrients.

In the incubation of the strain producing the endo-fucoidan-lyase of the second invention of the present invention, the yield of the enzyme varies depending on the incubation conditions. In general, it is preferable that the incubation temperature ranges from 15 to 30° C. and the pH value of the medium ranges from 5 to 9. The yield of the endo-fucoidan-lyase attains the maximum by incubating the strain under aeration and agitation for 5 to 72 hours. As a matter of course, the incubation conditions are appropriately selected depending on the strain employed, the medium composition, etc. so as to achieve the maximum yield.

The endo-fucoidan-lyase of the second invention of the present invention is contained in both of the cells and the culture supernatant.

The above-mentioned Flavobacterium sp. SA-0082 is incubated in an appropriate medium and the cells are harvested and disrupted by a means commonly employed for disrupting cells such as ultrasonication. Thus a cell-free extract can be obtained.

Subsequently, the extract is purified by purification means commonly employed in the art to thereby give a purified enzyme preparation. For example, the purification may be effected by salting out, ion exchange chromatography, hydrophobic bond column chromatography, gel filtration or the like to thereby give the purified endo-fucoidan-lyase of the second invention of the present invention free from any other fucoidan degrading enzymes.

The culture supernatant obtained by eliminating the cells from the above-mentioned culture medium also contains a large amount of this enzyme (extracellular enzyme) which can be purified by the same means as those employed for purifying the intracellular enzyme.

The endo-fucoidan-lyase of the second invention of the present invention has the following chemical and physicochemical properties. The extracellular enzyme is identical with the intracellular enzyme in the properties other than molecular weight.

(I) Function: acting on fucoidan to cause the liberation of at least the sugar compounds represented by the above formulae (7) and (8).

Figure 37:
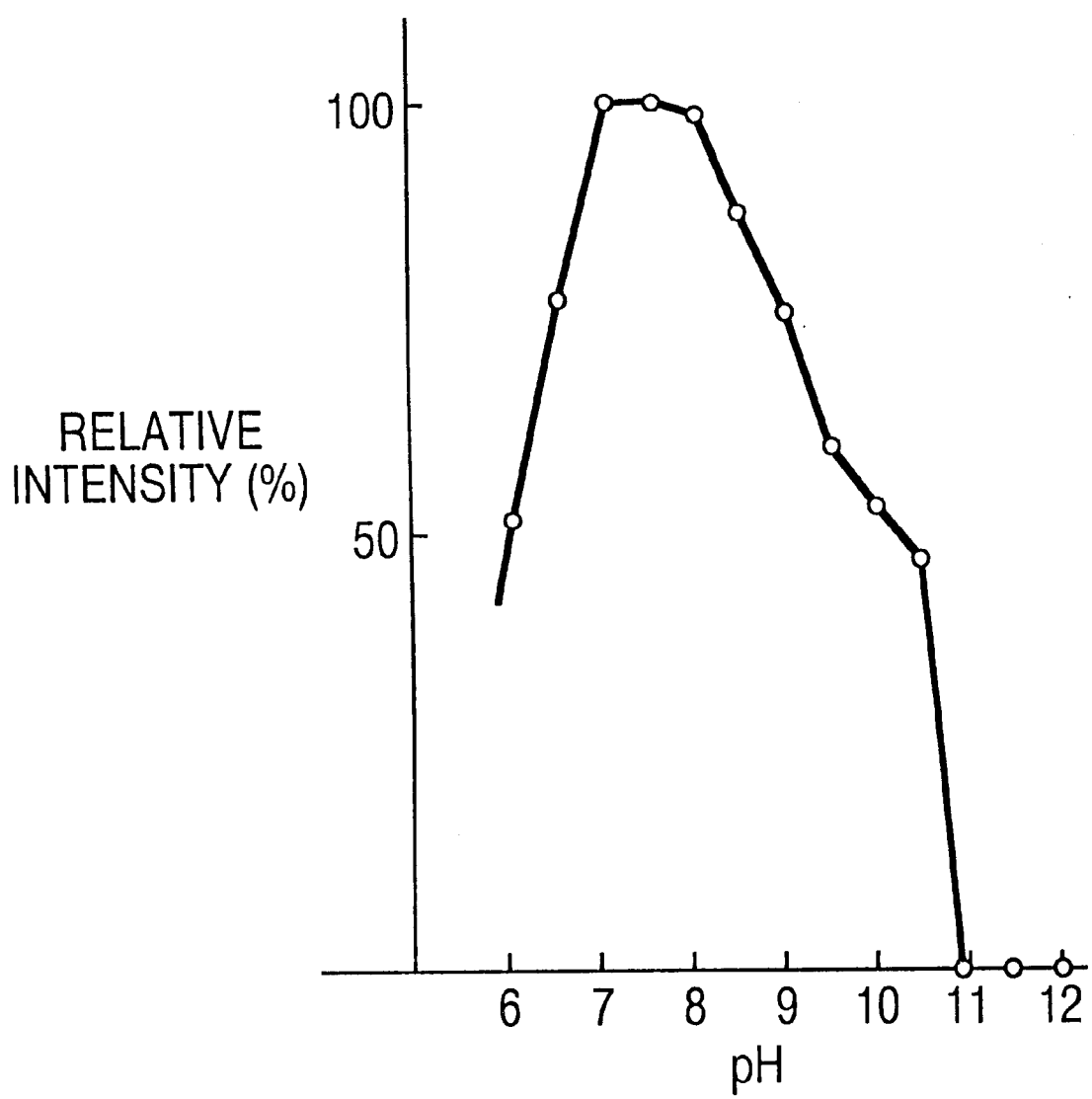
FIG. 37 is a graph which shows the relationship between the relative activity (%) of the enzyme according to the second invention of the present invention and the pH value.

(II) Optimum pH value: ranging from pH 6 to 10 (FIG. 37).

Namely, FIG. 37 is a graph which shows the relationship between the relative activity of this enzyme and the pH value wherein the ordinate refers to the relative activity (%) while the abscissa refers to the pH value.

(III) Optimum temperature: ranging from 30 to 40° C. (FIG. 38).

Figure 38:
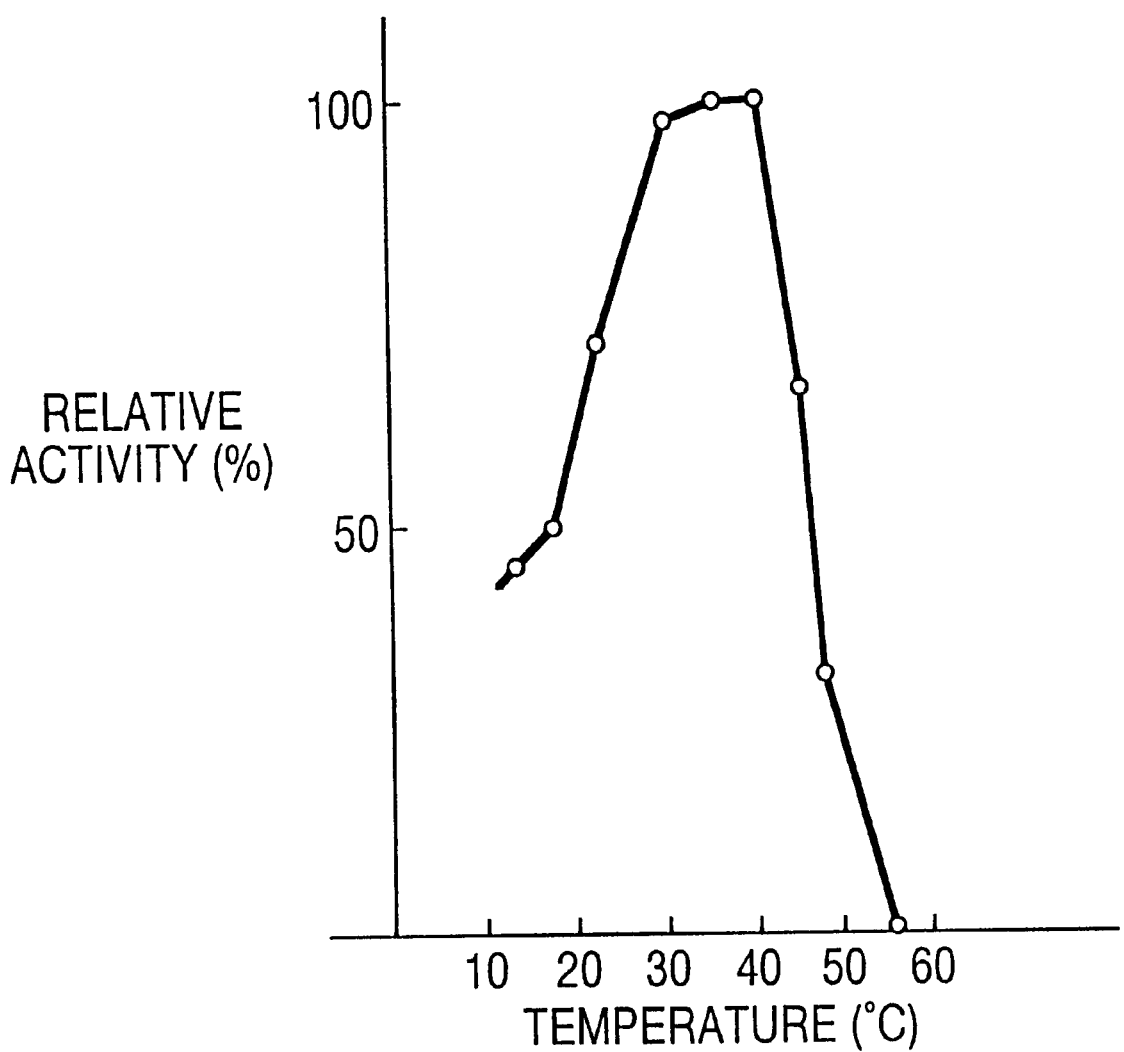
FIG. 38 is a graph which shows the relationship between the relative activity (%) of the enzyme according to the second invention of the present invention and the temperature (° C.).

Namely, FIG. 38 is a graph which shows the relationship between the relative activity of this enzyme and the temperature wherein the ordinate refers to the relative activity (%) while the abscissa refers to the temperature (° C.).

Figure 39:
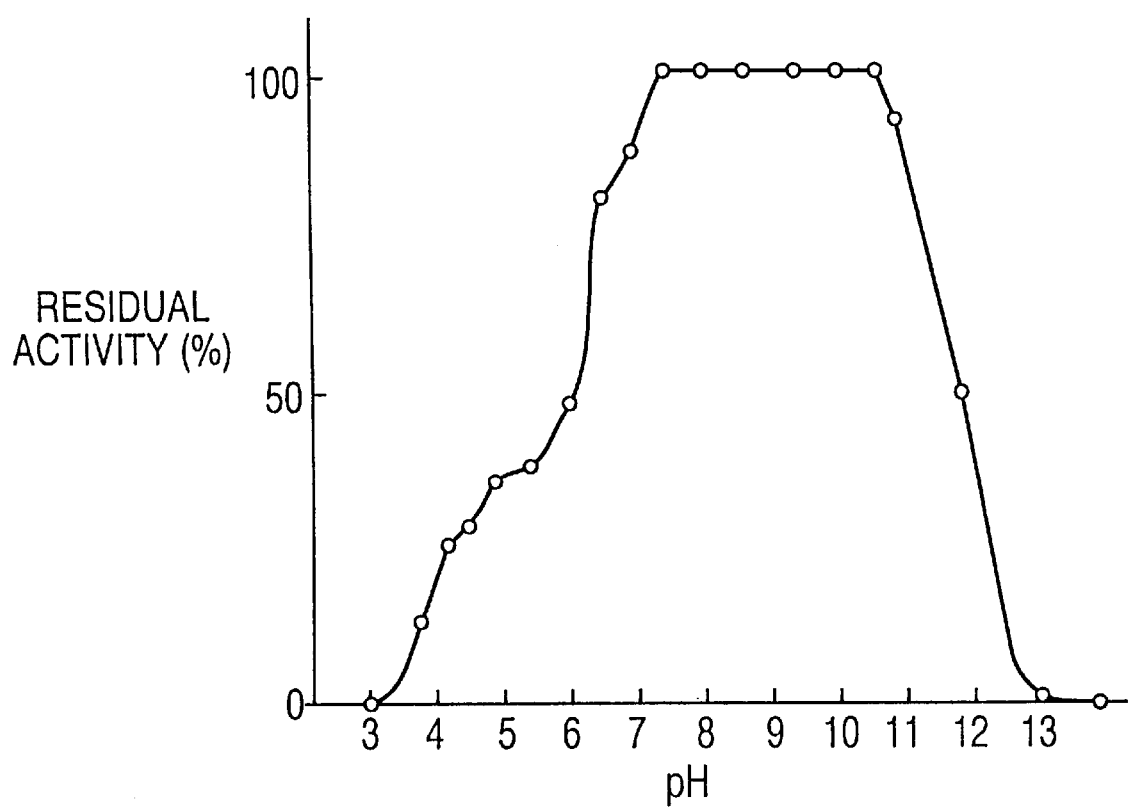
FIG. 39 is a graph which shows the relationship between the residual activity (%) of the enzyme according to the second invention of the present invention and the pH value at the treatment.

(IV) pH stability: being stable within a range of from pH 6 to 11.5 (FIG. 39).

Namely, FIG. 39 is a graph which shows the relationship between the residual activity of this enzyme and the pH value at the treatment wherein the ordinate refers to the residual activity (%) while the abscissa refers to the pH value.

Figure 40:
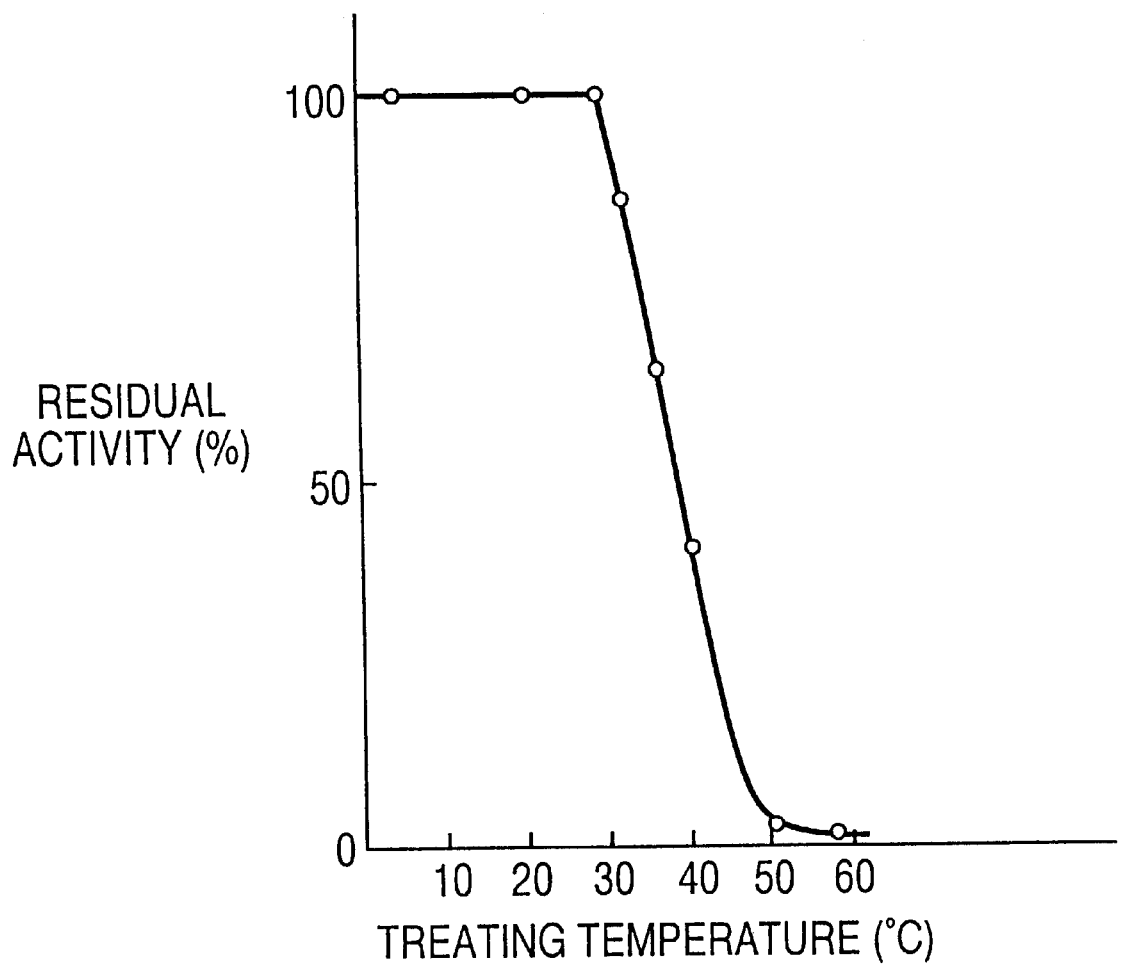
FIG. 40 is a graph which shows the relationship between the residual activity (%) of the enzyme according to the second invention of the present invention and the temperature (° C.) at the treatment.

(V) Temperature stability: being stable at temperatures of about 30° C. or less (FIG. 40).

Namely, FIG. 40 is a graph which shows the relationship between the residual activity of this enzyme and the temperature at the treatment wherein the ordinate refers to the residual activity (%) while the abscissa refers to the temperature (° C.).

(VI) Molecular weight: the molecular weight of this enzyme determined by gel filtration with the use of Sephacryl S-200 (mfd. by Pharmacia) is about 70,000 in the case of the extracellular enzyme of the strain Flavobacterium sp. SA-0082 or about 460,000 in the case of the intracellular enzyme of this strain.

(VII) Method for measuring enzymatic activity:

The activity of the endo-fucoidan-lyase of the second invention of the present invention is measured in the following manner.

50 $\mu$l of a 2.5% solution of fucoidan originating in Kjellmaniella crassifolia, 10 $\mu$l of the endo-fucoidan-lyase of the second invention of the present invention and 60 $\mu$l of an 83 mM phosphate buffer (pH 7.5) containing 667 mM of sodium chloride are mixed together and reacted at 37° C. for 3 hours. Then 105 $\mu$l of the reaction mixture is mixed with 2 ml of water under stirring and the absorbance (AT) is measured at 230 nm. As controls, use is made of a reaction mixture prepared by the same method but substituting the endo-fucoidan-lyase of the second invention of the present invention by the above-mentioned buffer alone employed for dissolving the enzyme and another reaction mixture prepared by the same method but substituting the fucoidan solution by water alone and the absorbances (AB1 and AB2) thereof are also measured.

The amount of the enzyme by which 1 $\mu$mol of the glycoside bond between mannose and uronic acid can be exclusively cleaved in one minute is referred to as one U. The bond thus cleaved is determined by taking the millimolar molecular extinction coefficient of the unsaturated uronic acid formed in the elimination reaction as 5.5. The activity of the enzyme is determined in accordance with the following equation:

$$\text{Activity (U/ml)}=(AT-AB1-AB2)\times 2.105\times 120/(5.5\times 105\times 0.01\times 180);$$

2.105: volume (ml) of the sample the absorbance of which is to be measured;

120: volume ($\mu$l) of the enzyme reaction mixture;

5.5: millimolar molecular extinction coefficient (/mM) of unsaturated uronic acid at 230 nm;

105: volume ($\mu$l) of the reaction mixture employed for dilution;

0.01: volume (ml) of the enzyme; and

180: reaction time (min).

The protein is determined by measuring the absorbance of the enzyme solution at 280 nm and calculated by taking the absorbance of the 1 mg/ml protein solution as 1.0.

The present inventors have determined the action mechanism of the endo-fucoidan-lyase of the second invention of the present invention in the following manner.

(1) Preparation of Kjellmaniella crassifolia Fucoidan

Dry Kjellmaniella crassifolia is ground with a free mill Model M-2 (mfd. by Nara Kikai Seisakusho) and treated in 10 times as much 85% methanol at 70° C. for 2 hours. Then it is filtered and the residue is further treated in 10 times as much methanol at 70° C. for 2 hours. After filtering, 20 times as much water is added to the residue. Then the mixture is treated at 100° C. for 3 hours and filtered to thereby give an extract. The salt concentration of the extract is adjusted to the same level as that of a 400 mM solution of sodium chloride. Then cetylpyridinium chloride is added thereto until no precipitate is formed any more. After centrifuging, the precipitate is thoroughly washed with ethanol to thereby completely eliminate the cetylpyridinium chloride. Next, it is subjected to desalting and the removal of low-molecular weight substances by using an ultrafilter (exclusion molecular weight of ultrafiltration membrane: 100,000, mfd. by Amicon). The precipitate thus formed is eliminated by centrifugation. The supernatant is freeze-dried to thereby give purified Kjellmaniella crassifolia fucoidan. The yield of the product is about 4% based on the weight of the dry Kjellmaniella crassifolia powder.

(2) Degradation of Fucoidan by Endo-fucoidan-lyase and Purification of Degradation Product The purified fucoidan originating in Kjellmaniella crassifolia is treated with the endo-fucoidan-lyase of the second invention of the present invention to thereby give the degradation products in large amounts.

Namely, 600 ml of a 5% solution of the fucoidan originating in Kjellmaniella crassifolia, 750 ml of a 100 mM phosphate buffer (pH 8.0), 150 ml of 4 M sodium chloride and 3.43 ml of a 1750 mU/ml solution of the endo-fucoidan-lyase of the present invention are mixed together and reacted at 25° C. for 144 hours.

Figure 41:
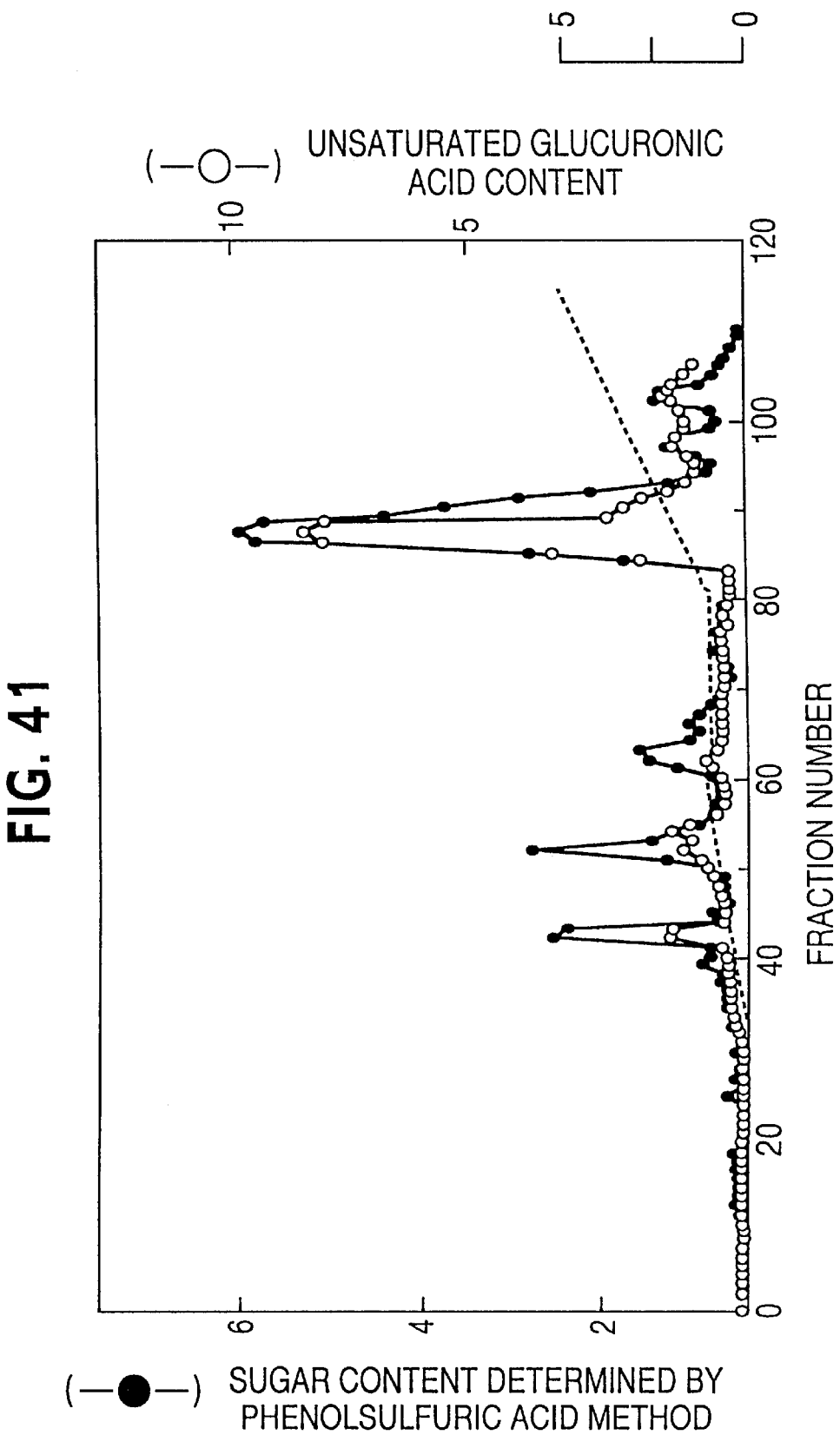
FIG. 41 shows the elution patterns of the sugar compounds (a) to (i) isolated by DEAE-Sepharose FF.

Then the reaction mixture is dialyzed by using a dialysis membrane of 3500 in pore size and a fraction of molecular weight of 3500 or less is taken up. After desalting with a Micro Acilyzer G3 (mfd. by Asahi Chemical Industry Co., Ltd.), this fraction is fractionated into nine fractions (a), (b), (c), (d), (e), (f), (g), (h) and (i) with DEAE-Sepharose FF. FIG. 41 shows the elution patterns thereof wherein the abscissa refers to the fraction number, the left ordinate and close circles refer to the sugar content of the sample determined by the phenol-sulfuric acid method and expressed in the absorbance at 480 nm, the right ordinate and open circles refer to the unsaturated glucuronic acid content of the sample expressed in the absorbance at 235 nm, and the rightmost ordinate and the dotted line refer to the ammonium acetate concentration (M) in the eluate. The fraction numbers of the fractions are respectively as follows: (a): from 42 to 43, (b): from 84 to 91, (c), from 51 to 52, (d): 79, (e): from 102 to 103, (f): from 62 to 63, (g): 45, (h): 75, and (i): 77.

Figure 42:
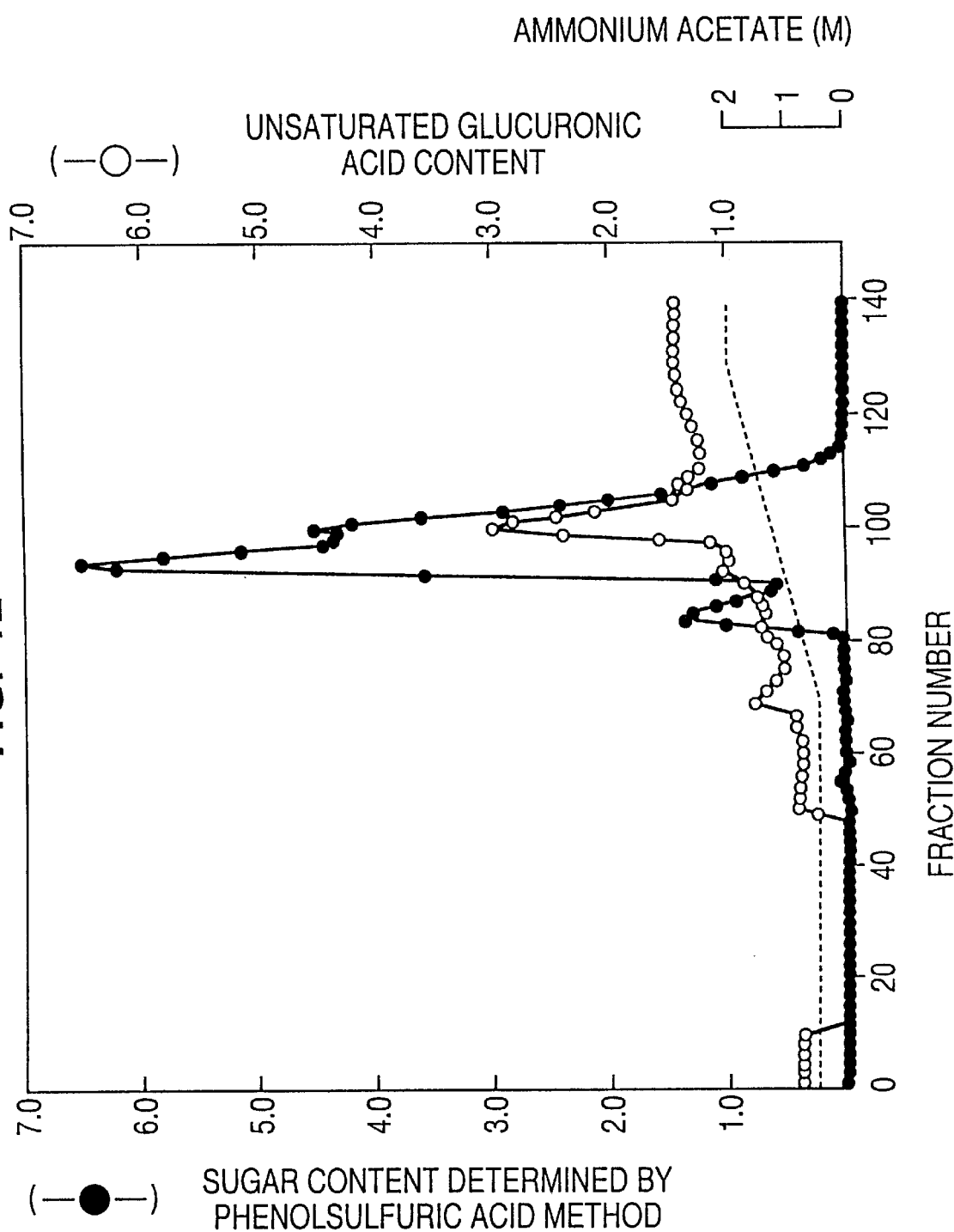
FIG. 42 shows the elution patterns of the sugar compounds (h) and (i) isolated by DEAE-Sepharose FF.

With respect to the fractions (h) and (i), the above-mentioned fractions of Nos. 64 to 78 are combined and re-purified with DEAE-Sepharose FF. FIG. 42 shows the elution patterns thereof wherein the abscissa refers to the fraction number, the left ordinate and close circles refer to the sugar content of the sample determined by the phenol-sulfuric acid method and expressed in the absorbance at 480 nm, the right ordinate and open circles refer to the unsaturated glucuronic acid content of the sample expressed in the absorbance at 235 nm, and the rightmost ordinate and the dotted line refer to the ammonium acetate concentration (M) in the eluate. The fraction numbers of the fractions are respectively as follows: (h): from 92 to 96, and (i): from 99 to 103.

(3) Analysis of the Structure of Enzymatic Reaction Product

① Confirmation of Uniformity of Each Fraction

A portion of each of the above-mentioned nine fractions (a), (b), (c), (d), (e), (f), (g), (h) and (i) is pyridyl-(2)- aminated (PA) at the reducing end by using GlycoTAG and GlycoTAG Reagent Kit (each mfd. by Takara Shuzo Co., Ltd.) to thereby give PA saccharides (PA-a), (PA-b), (PA-c) (PA-d), (PA-e), (PA-f), (PA-g), (PA-h) and (PA-i), which are then analyzed by HPLC. Thus it is confirmed that (PA-a), (PA-b), (PA-c) (PA-d), (PA-e), (PA-f), (PA-g), (PA-h) and (PA-i) are each a uniform substance.

The HPLC is effected under the following conditions.
Apparatus: Model L-6200 (mfd. by Hitachi, Ltd.).
Column: L-column (4.6×250 mm) [Kagaku Yakuhin Kensa Kyokai (Foundation)].
Eluent:
  50 mM acetic acid-triethylamine (pH 5.5) for the substances of the above formulae (7), (8) and (9) [i.e., (PA-a), (PA-b) and (PA-c)];
  100 mM acetic acid-triethylamine (pH 5) for the substances of the above formulae (10), (12) (13) and (15) [i.e., (PA-d), (PA-f), (PA-g) and (PA-i)];
  200 mM acetic acid-triethylamine (pH 3.8) from 0 to 10 minutes and 200 mM acetic acid-triethylamine (pH 3.8) and 200 mM acetic acid-triethylamine (pH 3.8) containing 0.5% of tetrahydrofuran from 10 to 60 minutes while linearly changing the ratio of the former to the latter from 100:0 to 20:80 for the substance of the above formula (11) [i.e., (PA-e)]; and 200 mM acetic acid-triethylamine (pH 3.8) and 200 mM acetic acid-triethylamine (pH 3.8) containing 0.5% of tetrahydrofran from 0 to 60 minutes while linearly changing the ratio of the former to the latter from 80:20 to 50:50 for the substance of the above formula (14) [i.e., (PA-h)].
Detection: Fluorometric Detector F-1150 (mfd. by Hitachi, Ltd.), excitation wavelength: 320 nm, fluorescent wavelength: 400 nm.
Flow rate: 1 ml/min.
Column temperature: 40° C.

② Analysis of Reducing End Sugar and Neutral Sugar Composition of Enzymatic Reaction Product The PA-sugars (PA-a), (PA-b), (PA-c), (PA-d), (PA-e), (PA-f), (PA-g), (PA-h) and (PA-i) are each hydrolyzed by treating with 4 N hydrochloric acid at 100° C. for 3 hours and the reducing end sugar is examined by HPLC.

Subsequently, the reducing ends of these hydrolyzates are pyridyl-(2)-aminated (PA) by using GlycoTAG and Glyco-TAG Reagent Kit (each mfd. by Takara Shuzo Co., Ltd.) and the neutral sugar compositions are analyzed by HPLC. The HPLC is effected under the following conditions.
Apparatus: Model L-6200 (mfd. by Hitachi, Ltd.).
Column: PALPAK Type A (4.6 mm×150 mm, mfd. by Takara Shuzo, Co., Ltd.).
Eluent: 700 mM borate buffer (pH 9.0): acetonitrile=9:1.
Detection: Fluorometric Detector F-1150 (mfd. by Hitachi, Ltd.), excitation wavelength: 310 nm, fluorescent wavelength: 380 nm;
Flow rate 0.3 ml/min; and
Column temperature: 65° C.

As a result, it is found out that (PA-a), (PA-b), (PA-c), (PA-d), (PA-e), (PA-f) and (PA-i) all carry mannose as the reducing end sugar. Regarding the neutral sugar composition, (PA-a), (PA-b), (PA-c), (PA-e), (PA-f) and (PA-i) contain mannose and fucose in equimolar amounts while (PA-d) contains mannose and fucose at a ratio of 2:1.

(PA-g) and (PA-h) each carry galactose as the reducing end sugar. Regarding the neutral sugar composition, (PA-g) contains galactose and fucose at a ratio of 1:2 while (PA-h) contains galactose and fucose at a ratio of 2:1.

Further, the configuration of mannose which is one of the constituting sugars is examined in the following manner. By using F-Kits Glucose/Fructose and Phosphomannose Isomerase (each mfd. by Boehringer Mannheim-Yamanouchi), a reaction system by which D-mannose alone can be determined is constructed in accordance with the manufacturer's description. Separately, 100 μg portions of the sugar compounds (a), (b), (c), (d), (e), (f) and (i) are each hydrolyzed with 2 N hydrochloric acid at 100° C. for 3 hours and, after neutralization, subjected to the determination in this reaction system. As a result, D-mannose is detected from all of the sugar compounds (a), (b), (c), (d), (e), (f) and (i). Thus it is proved that the sugar compounds (a), (b), (c), (d), (e), (f) and (i) all have D-mannose as the constituting sugar.

Further, the configuration of galactose which is one of the constituting sugars of (g) and (h) is examined by using F-Kit Lactose/Galactose (mfd. by Boehringer Mannheim-Yamanouchi) by which D-galactose alone can be detected. Namely, 100 μg portions of (g) and (h) are each hydrolyzed with 2 N hydrochloric acid at 100° C. for 3 hours and, after neutralization, subjected to the determination in this reaction system. As a result, galactose is detected from (g) and (h). Thus it is proved that (g) and (h) both have D-galactose as the constituting sugar.

Furthermore, the configuration of fucose which is another constituting sugar is examined in the following manner. In accordance with the method described in Clinical Chemistry, 36, 474–476 (1990), 100 μg portions of the above-mentioned compounds (a), (b), (c), (d), (e), (f), (g), (h) and (i) are hydrolyzed with 2 N hydrochloric acid at 100° C. for 3 hours and, after neutralization, subjected to the determination in this reaction system by which not D-fucose but L-fucose alone can be detected. As a result, L-fucose is detected from the sugar compounds (a), (b), (c), (d), (e), (f), (g), (h) and (i).

③ Analysis of Molecular Weight of Enzymatic Reaction Product

Next, the sugar compounds (a), (b), (c), (d), (e), (f), (g), (h) and (i) are subjected to mass spectrometry with the use of an API-III mass spectrograph (mfd. by Perkin-Elmer Science). Thus, it is found out that these substances have molecular weights of 564, 724, 1128, 1062, 1448, 644, 632, 1358 and 1288, respectively. In (b) and (c), divalent anions form major signals. A monovalent ion, a monovalent ion having sodium attached thereto and a divalent ion are detected from (d). A divalent ion having four sodium ions attached thereto, a trivalent ion having three sodium ions attached thereto, a tetravalent ion having a sodium ion attached thereto, etc. are detected from (e). A monovalent ion having two sodium ions attached thereto is detected from (f). A monovalent ion, a monovalent ion having sodium attached thereto and a divalent ion are detected from (g). Monovalent, divalent, trivalent and tetravalent ions respectively having four, three, two and one sodium ion, etc. are detected from (h). A monovalent ion from which two sulfate groups have been eliminated and to which a sodium ion has been attached and a divalent ion from which two sulfate groups have been eliminated are detected from (i).

By the mass-mass (MS/MS) spectrometry of the negative mode, detection is made from (a) of a monovalent sulfate ion (molecular weight 97), a monovalent ion (molecular weight 157) wherein a water molecule and a hydrogen ion have been eliminated from an unsaturated hexuronic acid, a monovalent ion (molecular weight 175) wherein a hydrogen ion has been eliminated from an unsaturated hexuronic acid, a monovalent ion (molecular weight 225) wherein a water molecule and a hydrogen ion have been eliminated from sulfated fucose, a monovalent ion (molecular weight 243)

wherein a hydrogen ion has been eliminated from sulfated fucose, a monovalent ion (molecular weight 319) wherein a water molecule and a hydrogen ion have been eliminated from an unsaturated hexuronic acid bonded to mannose, and a monovalent ion (molecular weight 405) wherein a hydrogen ion has been eliminated from sulfated fucose bonded to mannose.

By the MS/MS spectrometry of the negative mode, detection is made similarly from (b) of a monovalent sulfate ion (molecular weight 97), a monovalent ion (molecular weight 175) wherein a hydrogen ion has been eliminated from an unsaturated hexuronic acid, a monovalent ion (molecular weight 243) wherein a hydrogen ion has been eliminated from sulfated fucose, a divalent ion (molecular weight 321) wherein two hydrogen ions have been eliminated from an unsaturated hexuronic acid and sulfated fucose bonded to sulfated mannose, a monovalent ion (molecular weight 405) wherein a hydrogen ion has been eliminated from sulfated fucose bonded to mannose or fucose bonded to sulfated mannose, and a monovalent ion (molecular weight 417) wherein a hydrogen ion has been eliminated from an unsaturated hexuronic acid bonded to sulfated mannose.

By the MS/MS spectrometry of the negative mode, detection is made from (c) of a monovalent sulfate ion (molecular weight 97), a monovalent ion (molecular weight 175) wherein a hydrogen ion has been eliminated from an unsaturated hexuronic acid, a monovalent ion (molecular weight 225) wherein a water molecule and a hydrogen ion have been eliminated from sulfated fucose, a monovalent ion (molecular weight 243) wherein a hydrogen ion has been eliminated from sulfated fucose, a divalent ion (molecular weight 371) wherein two hydrogen ions have been eliminated from sulfated fucose bonded to mannose bonded to a hexuronic acid bonded to mannose, a monovalent ion (molecular weight 405) wherein a hydrogen ion has been eliminated from sulfated fucose bonded to mannose, and a monovalent ion (molecular weight 721) wherein water and a hydrogen ion have been eliminated from sulfated fucose and an unsaturated hexuronic acid bonded mannose bonded to hexuronic acid.

By the MS/MS spectrometry of the negative mode, detection is made from the divalent ions of (d) of a monovalent sulfate ion (molecular weight 97), a monovalent ion (molecular weight 175) wherein a hydrogen ion has been eliminated from an unsaturated hexuronic acid, a monovalent ion (molecular weight 225) wherein a water molecule and a hydrogen ion have been eliminated from sulfated fucose, a monovalent ion (molecular weight 243) wherein a hydrogen ion has been eliminated from sulfated fucose, a monovalent ion (molecular weight 405) wherein a hydrogen ion has been eliminated from sulfated fucose bonded to mannose, a divalent ion (molecular weight 450) wherein two sulfate groups and two hydrogen ions have been eliminated from (d), and a divalent ion (molecular weight 490) wherein sulfate group and two hydrogen ions have been eliminated from (d).

By the MS/MS spectrometry of the negative mode, detection is made from (e) of a monovalent sulfate ion (molecular weight 97), a monovalent ion (molecular weight 225) wherein a water molecule and a hydrogen ion have been eliminated from sulfated fucose, a monovalent ion (molecular weight 243) wherein a hydrogen ion has been eliminated from sulfated fucose, a monovalent ion (molecular weight 345) wherein two hydrogen ions have been eliminated from and a sodium ion has been attached to disulfated fucose, a trivalent ion (molecular weight 450) wherein two sulfate groups have been eliminated, three sodium ions have been attached and six hydrogen ions have been eliminated from (e), a trivalent ion (molecular weight 476) wherein a sulfate group and six hydrogen ions have been eliminated from (e) and three sodium ions have been attached thereto, a monovalent ion (molecular weight 563) wherein a hydrogen ion has been eliminated from an unsaturated hexuronic acid and sulfated fucose bonded to mannose, and a monovalent ion (molecular weight 705) wherein a water molecule and a hydrogen ion have been eliminated from an unsaturated hexuronic acid and disulfated fucose bonded to sulfated mannose.

By the MS/MS spectrometry of the negative mode, detection is made from (f) of a monovalent sulfate ion (molecular weight 97), a monovalent ion (molecular weight 243) wherein a hydrogen ion has been eliminated from sulfated fucose, and a monovalent ion (molecular weight 421) wherein water and two hydrogen ions have been eliminated from and a sodium ion has been attached to an unsaturated hexuronic acid bonded to sulfated mannose.

By the MS/MS spectrometry of the negative mode, detection is made from (g) of a monovalent ion (molecular weight 405) wherein a hydrogen ion has been eliminated from sulfated fucose bonded to galactose and a monovalent ion (molecular weight 551) wherein a hydrogen ion has been eliminated from sulfated fucose bonded to fucose bonded to galactose or fucose bonded to sulfated fucose bonded to galactose.

By the MS/MS spectrometry of the negative mode, detection is made from the substance, wherein three sodium ions have been attached to (h) and five hydrogen ions have been eliminated therefrom, of a monovalent sulfate ion (molecular weight 97), a monovalent ion (molecular weight 225) wherein a water molecule and a hydrogen ion have been eliminated from sulfated fucose, and a monovalent ion (molecular weight 1197) wherein a hydrogen ion and two sulfate groups have been eliminated from (h).

By the MS/MS spectrometry of the negative mode, detection is made from the divalent ion, wherein two sulfate groups and two hydrogen ions have been eliminated from (i), of a monovalent sulfate ion (molecular weight 97) and a monovalent ion (molecular weight 345) wherein two hydrogen ions have been eliminated from and a sodium ion has been attached to disulfated fucose.

④ Analysis of Sugar Composition of Enzymatic Reaction Product

As the above results of mass spectrometry indicate, there is a high possibility that the sugar compounds (a), (b), (c), (d), (e), (f) and (i) might each contain an unsaturated hexuronic acid in its molecule.

Thus the following experiment is conducted to prove that these enzymatic reaction products each contains a hexuronic acid carrying an unsaturated bond in its molecule. It is known that a strong absorption at 230 to 240 nm is assignable to an unsaturated bond in a molecule. Thus, the absorbance of the aqueous solution of each of the purified oligosaccharides (a), (b), (c), (d), (e), (f), (g), (h) and (i) is measured at 230 to 240 nm. As a result, the aqueous solutions of (a), (b), (c), (d), (e), (f) and (i) each shows a strong absorption, which suggests the presence of an unsaturated bond in the molecule. It is also confirmed that the absorbance at 230 to 240 nm increases as the degradation of fucoidan by this enzyme proceeds. These facts strongly suggest that this enzyme would cleave the glycoside bond between mannose and a hexuronic acid or galactose and a hexuronic acid in fucoidan via an elimination reaction.

Most of the enzymatic reaction products have an unsaturated hexuronic acid at the nonreducing ends and carry mannose at the reducing ends, which suggests that the fucoidan prepared involves a molecular species composed of a hexuronic acid and mannose alternately bonded to each other.

Because of containing fucose as the main constituting saccharide, fucoidan is more liable to be degraded with acids than common polysaccharides. On the other hand, it is known that the bonds of hexuronic acids and mannose are relatively highly tolerant to acids. The present inventors have attempted to identify the hexuronic acid in the sugar chain which is composed of the hexuronic acid and mannose alternately bonded to each other and contained in the fucoidan originating in *Kjellmaniella crassifolia* in the following manner with reference to the method described in Carbohydrate Research, 125, 283–290 (1984). First, the fucoidan is dissolved in 0.3 M oxalic acid and treated at 100° C. for 3 hours. Then it is subjected to molecular weight fractionation and fractions of molecular weight of 3,000 or more are combined. Then it is further treated with an anion exchange resin and the adsorbed matters are collected. The substance thus obtained is freeze-dried and hydrolyzed with 4 N hydrochloric acid. After adjusting the pH value to 8, it is pyridyl-(2)-aminated and uronic acid is analyzed by HPLC. The HPLC is effected under the following conditions.

Apparatus: Model L-6200 (mfd. by Hitachi, Ltd.);
Column: PALPAK Type N (4.6 mm×250 mm, mfd. by Takara Shuzo, Co., Ltd.);
Eluent: 200 mM acetic acid-triethylamine buffer (pH 7.3): acetonitrile=25:75;
Detection: Fluorometric Detector F-1150 (mfd. by Hitachi, Ltd.), excitation wavelength: 320 nm, fluorescent wavelength: 400 nm;
Flow rate : 0.8 ml/min;
Column temperature: 40° C.

As the standards for PA hexuronic acids, use is made of those prepared by pyridyl-(2)-amination of glucuronic acid manufactured by Sigma Chemical Co., galacturonic acid manufactured by Wako Pure Chemical Industries, Ltd., iduronic acid obtained by hydrolyzing 4-methylumbelliferyl-α-L-iduronide manufactured by Sigma Chemical Co., and mannuronic acid and guluronic acid obtained by hydrolyzing alginic acid (mfd. by Wako Pure Chemical Industries, Ltd.) in accordance with the method described in Acta Chemica Scandinavicaj, 15, 1397–1398 (1961) followed by the separation with an anion exchange resin.

As a result, it is found out that glucuronic acid alone is contained as the hexuronic acid in the above-mentioned molecular species of fucoidan.

Further, the glucuronic acid in the hydrolyzate of the above-mentioned molecular species is separated from D-mannose by using an anion exchange resin and freeze-dried. Then the specific rotation thereof is measured. It is thus clarified that the glucuronic acid is a dextrorotatory one, i.e., D-glucuronic acid.

Further, the fucoidan originating in *Kjellmaniella crassifolia* is treated with the endo-fucoidan hydrolase of the second invention of the present invention and then hydrolyzed with the use of oxalic acid similar to the above case. However, no polymer having D-glucuronic acid and D-mannose alternately bonded to each other is found out. Based on these results, it is clarified that the enzyme of the present invention cleaves, via the elimination reaction, a molecular species having a skeleton structure composed of D-glucuronic acid and D-mannose alternately bonded to each other.

Further, the polymer obtained by the hydrolysis with oxalic acid is subjected to NMR spectrometry to thereby examine the anomeric configuration of the binding sites of D-glucuronic acid and D-mannose and the glycoside bond.

The obtained NMR spectra of the polymer are as follows. The chemical shifts in the $^1$H-NMR spectra are expressed by taking the chemical shift of the methyl group in triethylamine as 1.13 ppm, while those in the $^{13}$C-NMR spectra are expressed by taking the chemical shift of the methyl group in triethylamine as 9.32 ppm.

$^1$H-NMR (D$_2$O) δ5.25(1H, br-s, 1-H), 4.32(1H, d, J=7.6 Hz, 1'-H), 4.00(1H, br-s, 2-H), 3.71(1H, m, 5'-H), 3.69(1H, m, H of 5-CH), 3.68(1H, m, 3-H), 3.63(1H, m, H of 5-CH), 3.63(1H, m, 4'-H), 3.57(1H, m, 4-H), 3.54(1H, m, 3'-H), 3.53(1H, m, 5-H), 3.25(1H, t, J=8.5 Hz, 2'-H)

$^{13}$C-NMR (D$_2$O) δ175.3(C of 5'-COOH), 102.5(1'-C), 99.6(1-C), 78.5(2-C), 77.9(4'-C), 77.0(3'-C), 76.7(5'-C), 73.9(5-C), 73.7(2'-C), 70.6(3-C), 67.4(4-C), 61.0(C of 5-CH$_2$OH)

The peaks are assignable respectively to the positions shown by the numerical values in the following formula (16):

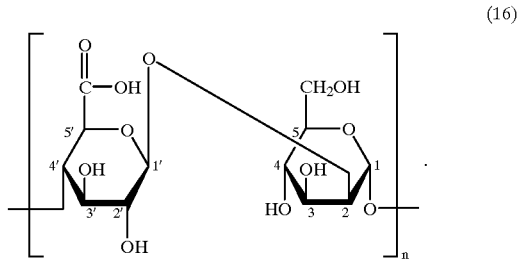

(16)

Regarding the configuration at the 1-position of the D-glucuronic acid, it is identified as β-D-glucuronic acid because of its vicinal binding constant of 7.6 Hz.

Regarding the configuration at the 1-position of the D-mannose, it is identified as α-D-mannose because of its chemical shift of 5.25 ppm.

The binding manners of the constituting sugars are analyzed by the HMBC method, i.e., the $^1$H-dtected multiple-bond heteronuclear multiple quantum coherence spectrum.

The DQF-COSY and HOHAHA methods are employed in the assignment in the $^1$H-NMR spectra while the HSQC method is employed in the assignment in the $^{13}$C-NMR spectra.

In the HMBC spectrum, cross peaks are observed between 1-H and 4'-C with between 4'-H and 1-C, and between 1'-H and 2-C with between 2-H and 1'-C. These facts indicate that D-glucuronic acid is bonded to the 2-position of D-mannose via a β-bond while D-mannose is bonded to the 4-position of D-glucuronic acid via an α-bond.

⑤ Analysis on Sugar Binding Manner and Binding Site of Sulfate Group in Enzymatic Reaction Product To examine the binding manner of the constituting sugars and sulfate groups, the enzymatic reaction products are analyzed by NMR spectrometry with the use of a nuclear magnetic resonance spectrometer Model JNM-α500 (500 Mz; mfd. by JEOL Ltd.). The analytical data thus obtained indicate that the sugar compounds (a), (b), (c), (d), (e), (f), (g), (h) and (i) are represented respectively by the above formulae (7), (8), (9), (10), (11), (12), (13), (14) and (15). That is to say, the facts thus clarified are as follows. The sugar compound (a) has a structure wherein unsaturated D-glucuronic acid and L-fucose having a sulfate group bonded thereto are attached to D-mannose which is a reducing end residue. The sugar compound (b) has a structure wherein unsaturated D-glucuronic acid and L-fucose having two sulfate groups bonded thereto are attached to D-mannose which is a reducing end residue having a sulfate group bonded thereto. The sugar compound (c) has a structure wherein D-glucuronic acid and L-fucose having a sulfate group bonded thereto are attached to D-mannose which is a reducing end residue, D-mannose is attached further to the D-glucuronic acid and unsaturated D-glucuronic acid, and L-fucose having a sulfate group bonded thereto are attached furthermore to the D-mannose. The sugar compound (d) has a structure wherein a sulfate group, D-glucuronic acid and L-fucose having two sulfate groups bonded thereto are attached to D-mannose which is a reducing end residue, D-mannose is attached further to the D-glucuronic acid, and unsaturated D-glucuronic acid is attached furthermore to the D-mannose. The sugar compound (e) has a structure wherein a sulfate group, D-glucuronic acid and L-fucose having two sulfate groups bonded thereto are attached to D-mannose which is a reducing end residue, D-mannose having a sulfate group bonded thereto is attached further to the D-glucuronic acid, and L-fucose having two sulfate groups bonded thereto and unsaturated D-glucuronic acid are attached furthermore to the D-mannose. The sugar compound (f) has a structure wherein unsaturated D-glucuronic acid and L-fucose having a sulfate group bonded thereto are attached to D-mannose which is a reducing end residue having a sulfate group bonded thereto. The sugar compound (g) has a structure wherein L-fucose having a sulfate group bonded thereto is attached to D-galactose which is a reducing end residue and L-fucose having a sulfate group is attached further to the L-fucose. The sugar compound (h) has a structure consisting of two branched chains starting with D-galactose which is a reducing end residue having a sulfate group bonded thereto wherein L-fucose having a sulfate group bonded thereto is attached to D-galactose and L-fucose having a sulfate group is attached further to the L-fucose in one of the sugar chains while D-galactose having a sulfate group bonded thereto is attached to D-galactose having a sulfate group bonded thereto in another sugar chain. The sugar compound (i) has a structure wherein a sulfate group, D-glucuronic acid and L-fucose having a sulfate group bonded thereto are attached to D-mannose which is a reducing end residue, D-mannose is attached further to the D-glucuronic acid, and L-fucose having two sulfate groups bonded thereto and unsaturated D-glucuronic acid are attached furthermore to the D-mannose.

The compounds involved in the first invention of the present invention are obtained by treating fucoidan with the endo-fucoidan-lyase of the second invention of the present invention.

Next, the physical properties of the compounds represented by the formulae (7), (8), (9), (10), (11), (12), (13), (14) and (15), i.e., the sugar compounds (a), (b), (c), (d), (e), (f), (g), (h) and (i) which are examples of the sugar compounds of the present invention will be described.

FIGS. 1, 2, 3, 4, 5, 6, 7, 8 and 9 show the HPL Celution patterns of the pyridyl-(2)-aminated sugar compounds (PA-a), (PA-b), (PA-c), (PA-d), (PA-e), (PA-f), (PA-g), (PA-h) and (PA-i), respectively. In each figure, the ordinate refers to the relative fluorescence intensity while the abscissa refers to the retention time (min). Further, FIGS. 10, 11, 12, 13, 14, 15, 16, 17 and 18 show the mass spectra of the sugar compounds (a), (b), (c), (d), (e), (f), (g), (h) and (i), respectively, while FIGS. 19, 20, 21, 22, 23, 24, 25, 26 and 27 show the mass-mass spectra of the sugar compounds (a), (b), (c), (d), (e), (f), (g), (h) and (i), respectively. In each figure, the ordinate refers to the relative intensity (%) while the abscissa refers to m/z.

Furthermore, FIGS. 28, 29, 30, 31, 32, 33, 34, 35 and 36 show the $^1$H-NMR spectra of the sugar compounds (a), (b), (c), (d), (e), (f), (g), (h) and (i), respectively. In each figure, the ordinate refers to the signal intensity while the abscissa refers to the chemical shift (ppm).

The chemical shifts in the $^1$H-NMR spectra are expressed by taking the chemical shift of HOD as 4.65 ppm.

Physical properties of the compound (a):

Molecular weight: 564.

MS m/z: 563 [M–H$^+$]$^-$.

MS/MS m/z: 97 (HSO$_4$)$^-$, 157 [unsaturated D-glucuronic acid-H$_2$O—H$^+$]$^-$, 175 [unsaturated D-glucuronic acid-H$^+$]$^-$, 225 [sulfated L-fucose-H$_2$O—H$^+$]$^-$, 243 [sulfated L-fucose-H$^+$]$^-$, 319 [unsaturated D-glucuronic acid bonded to D-mannose-H$_2$O—H$^{+1-}$, 405 [M-unsaturated D-glucuronic acid-H$^+$]$^-$, 483 [M—SO$_3$—H$^+$]$^-$.

$^1$H-NMR (D$_2$O) δ5.78(1H, d, J=3.7 Hz, 4"-H), 5.26(1H, d, J=1.2 Hz, 1-H), 5.12(1H, d, J=4.0 Hz, 1'-H), 5.03(1H, d, J=6.1 Hz, 1"-H), 4.47(1H, d-d, J=3.4, 10.4 Hz, 3'-H), 4.21 (1H, br-s, 2-H), 4.12(1H, m, 5'-H), 4.10(1H, d-d, J=3.7, 5.8 Hz, 3"-H), 4.03(1H, d, J=3.4 Hz, 4'-H), 3.86(1H, m, 3-H), 3.83(1H, d-d, J=4.0, 10.4 Hz, 2'-H), 3.72(1H, m, 4-H), 3.72(1H, m, 5-H), 3.70(2H, m, H$_2$ of 5-CH$_2$), 3.65(1H, d-d, J=5.8, 6.1 Hz, 2"-H), 1.08(3H, d, J=6.7 Hz, H$_3$ of 5'-CH$_3$)

Sugar composition:

L-fucose:unsaturated D-glucuronic acid:D-mannose =1:1:1 (each one molecule).

Sulfate group:

one molecule (at the 3-position of L-fucose).

The peaks in the $^1$H-NMR spectra are assignable respectively to the positions shown by the numerical values in the following formula (17):

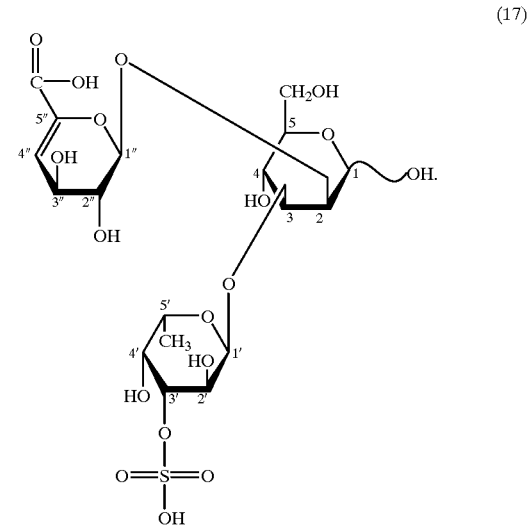

(17)

Physical properties of the compound (b):

Molecular weight: 724.

MS m/z: 723 [M–H$^+$]$^-$, 361 [M–2H$^+$]$^{2-}$.

MS/MS m/z: 97 [HSO$_4$]$^-$, 175 [unsaturated D-glucuronic acid-H$^+$]$^-$, 243 [sulfated L-fucose-H$^+$]$^-$, 321 [M—SO$_3$—2H$^+$]$^{2-}$, 405 [M-unsaturated D-glucuronic acid-2SO$_3$—H$^+$]$^-$, 417 (M-L-fucose-2SO$_3$—H$^+$]$^-$.

$^1$H-NMR (D$_2$O) δ5.66(1H, d, J=3.4 Hz, 4"-H), 5.27(1H, d, J=7.3 Hz, 1"-H), 5.25(1H, d, J=1.8 Hz, 1-H), 5.21(1H, d,

J=3.7 Hz, 1'-H), 4.50(1H, d, J=3.1 Hz, 4'-H), 4.32(1H, q, J=6.7 Hz, 5'-H), 4.27(1H, d-d, J=3.7, 10.4 Hz, 2'-H), 4.21 (1H, d-d, J=3.4, 6.7 Hz, 3"-H), 4.18(1H, d-d, J=1.8, 11.0 Hz, H of 5-CH), 4.15(1H, br-s, 2-H), 4.10(1H, d-d, J=5.8, 11.0 Hz, H of 5-CH), 3.99(1H, d-d, J=3.1, 10.4 Hz, 3'-H), 3.90(1H, m, 5-H), 3.82(1H, m, 3-H), 3.82(1H, m, 4-H), 3.54(1H, br-t, J=7.3 Hz, 2"-H), 1.11(3H, d, J=6.7 Hz, $H_3$ of 5'-$CH_3$)

Sugar composition:

L-fucose:unsaturated D-glucuronic acid:D-mannose= 1:1:1 (each one molecule).

Sulfate group:

three molecules (at the 2- and 4-positions of L-fucose and the 6-position of D-mannose).

The peaks in the $^1$H-NMR spectra are assignable respectively to the positions shown by the numerical values in the following formula (18):

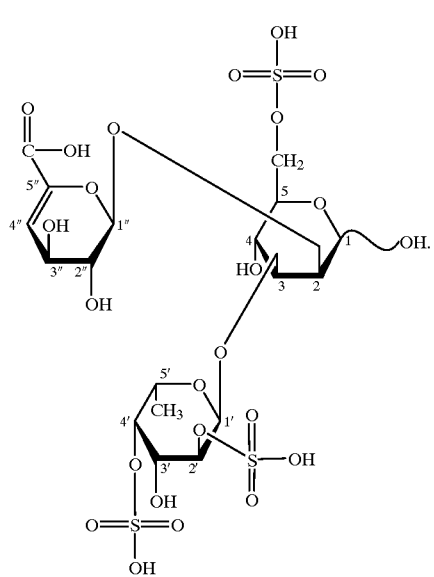

(18)

Physical properties of the compound (c):

Molecular weight 1128.

MS m/z: 1127 [M–H$^+$]$^-$.

MS/MS m/z: 97 [HSO$_4$]$^-$, 175 [unsaturated D-hexuronic acid-H$^+$]$^-$, 225 [sulfated L-fucose-H$_2$O—H$^+$]$^-$, 243 [sulfated L-fucose-H$^+$]$^-$, 371 [M-unsaturated D-glucuronic acid-L-fucose-SO$_3$— 2H$^+$]$^{2-}$, 405 [sulfated L-fucose bonded to D-mannose-H$^+$]$^-$, 721 [M-D-mannose-L-fucose-SO$_3$—H$_2$O—H$^+$]$^-$.

$^1$H-NMR (D$_2$O) δ5.69(1H, d, J=3.7 Hz, (4)"-H), 5.34(1H, s, (1)-H), 5.16(1H, s, 1-H), 5.10(1H, d, J=4.0 Hz, (1) '-H), 5.05(1H, d, J=3.7 Hz, 1'-H), 4.93(1H, d, J=6.4 Hz, (1)"-H), 4.50(1H, d-d, J=3.4, 10.7 Hz, 3'-H), 4.47(1H, d-d, J=3.4, 10.4 Hz, (3)'-H), 4.39(1H, d, J=7.9 Hz, 1"-H), 4.33(1H, br-s, (2)-H), 4.14(1H, m, 2-H), 4.12(1H, m, (3) "-H), 4.12(1H, m, 5'-H), 4.12(1H, m, (5) '-H), 4.04(1H, m, 4'-H), 4.03(1H, m, (4)'-H), 3.85(1H, m, 2'-H), 3.85(1H, m, (2)'-H), 3.82(1H, m, 3-H), 3.82(1H, m, (3)-H), 3.73(1H, m, 4-H), 3.73(1H, m, 5-H), 3.73(1H, m, (4)-H), 3.70(2H, m, H$_2$ of 5-CH$_2$), 3.70(2H, m, H$_2$ of (5)-CH$_2$), 3.67(1H, m, 5"-H), 3.62(1H, m, 4"-H), 3.62(1H, m, (2)"-H), 3.62(1H, m, (5)-H), 3.51(1H, t, J=8.9 Hz, 3"-H), 3.28(1H, t, J=7.9 Hz, 2"-H), 1.09(3H, d, J=6.7 Hz, H$_3$ of (5)'-CH$_3$), 1.07(1H, d, J=6.7 Hz, H$_3$ of 5'-CH$_3$)

Sugar composition:

L-fucos:unsaturated D-glucuronic acid:D-glucuronic acid:D-mannose=2:1:1:2 (L-fucose and D-mannose: each two molecules, unsaturated D-glucuronic acid and D-glucuronic acid: each one molecule).

Sulfate group:

two molecules (at the 3-position of each L-fucose).

The peaks in the $^1$H-NMR spectra are assignable respectively to the positions shown by the numerical values in the following formula (19):

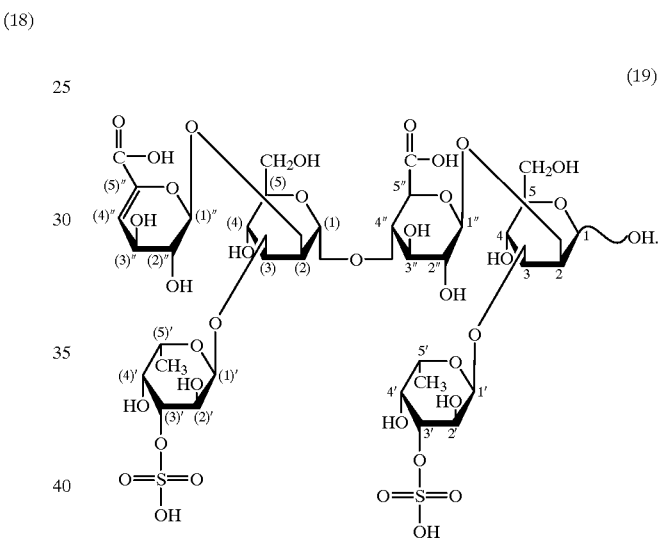

(19)

Physical properties of the compound (d):

Molecular weight 1062.

MS m/z: 1061 [M–H$^+$]$^-$.

MS/Ms m/z: 97 [HSO$_4$]$^-$, 175 [unsaturated hexuronic acid-H$^+$]$^-$, 225 [sulfated L-fucose-H$_2$O—H$^+$]$^-$, 243 [sulfated L-fucose-H$^+$]$^-$, 405 [sulfated L-fucose bonded to D-mannose-H$^+$]$^-$ or [L-fucose bonded to sulfated D-mannose-H$^+$]$^-$, 450 [M—2SO$_3$—2H$^+$]$^{2-}$, 490 [M—SO$_3$—2H$^+$]$^{2-}$.

$^1$H-NMR (D$_2$O) δ5.67(1H, d, J=3.7 Hz, (4)"-H), 5.32(1H, br-s, (1)-H), 5.17(1H, d, J=3.5 Hz, 1'-H), 5.17(1H, br-s, 1-H), 4.93(1H, d, J=6.4 Hz, (1)"-H), 4.71(1H, m, 1"-H), 4.53(1H, d, J=3.4 Hz, 4'-H), 4.33(1H, q, J=6.7 Hz, 5'-H), 4.28(1H, d-d, J=3.5, 11.0 Hz, 2'-H), 4.18(1H, m, H of 5-CH$_2$), 4.13(1H, m, (2)-H), 4.12(1H, m, (3)"-H), 4.08(1H, m, H of 5-CH$_2$), 4.07(1H, m, 2-H), 3.98(1H, d-d, J=3.4, 11.0, 3'-H), 3.88(1H, m, 5-H), 3.82(1H, m, 4"-H), 3.78(1H, m, 3-H), 3.78(1H, m, 4-H), 3.78(1H, m, (3)-H), 3.67(2H, m, H$_2$ of (5)-CH$_2$), 3.63(1H, m, (2)"-H), 3.60(1H, m, 3"-H), 3.59(1H, m, 5"-H), 3.57(1H, m, (4)-H), 3.57(1H, m, (5)-H), 3.16(1H, t, J=7.9 Hz, 2"-H), 1.10(3H, d, J=6.7 Hz, H$_3$ of 5'-CH$_3$)

Sugar composition:

L-fucose:unsaturated D-glucuronic acid:D-glucuronic acid:D-mannose=1:1:1:2 (L-fucose, unsaturated D-glucuronic acid and D-glucuronic acid: each one molecule, D-mannose: two molecules).

Sulfate group:

three molecule (at the 2-and 4-positions of L-fucose and the 6-position on the reducing end side of D-mannose).

The peaks in the $^1$H-NMR spectra are assignable respectively to the positions shown by the numerical values in the following formula (20):

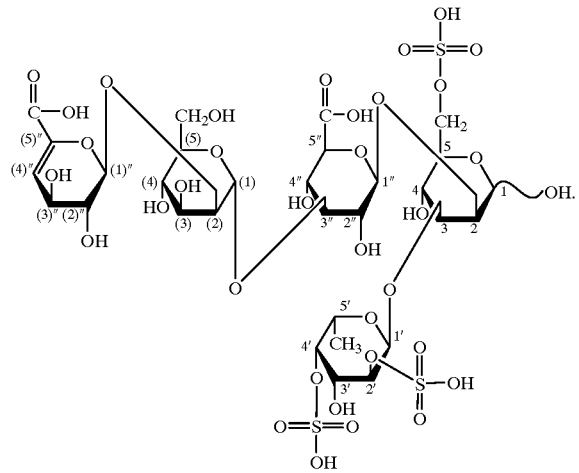

(20)

Physical properties of the compound (e):

Molecular weight: 1448.

MS m/z: 767 [M+4Na$^+$—6H$^+$]$^{2-}$, 503.7 [M+3Na$^+$—6H$^+$]$^{3-}$ and 366.5 [M+Na$^+$-5H$^+$]$^{4-}$.

MS/MS m/z: 97 [HSO$_4$]$^-$, 255 [sulfated L-fucose-H$_2$O—H$^+$]$^-$ 243 [sulfated L-fucose-H$^+$]$^-$, 345 [disulfated L-fucose +Na$^+$—2H$^+$]$^-$, 450 [M+3Na$^+$—2SO$_3$—6H$^+$]$^{3-}$, 477 [M+3Na$^+$—SO$_3$—6H$^+$]$^{3-}$, 563 [unsaturated D-glucuronic acid and sulfated L-fucose bonded to D-mannose-H$^+$]$^-$ or [unsaturated D-glucuronic acid and L-fucose bonded to sulfated D-mannose-H$^+$]$^-$, 705 [unsaturated D-glucuronic acid and disulfated L-fucose bonded to sulfated D-mannose-H$_2$O—H$^+$]$^-$.

$^1$NMR (D$_2$O) δ5.58(1H, d, J=3.4 Hz, (4)″-H) .5.35(1H, br-s, (1) -H), 5.22(1H, d, J=6.7 Hz, (1)″-H), 5.19(1H, d, J=3.7 Hz, 1′-H), 5.19(1H, d, J=3.7 Hz, (1)′-H), 5.16(1H, d, J=1.8 Hz, 1-H), 4.62(1H, d, J=7.6 Hz, 1″-H), 4.50(1H, m, 4′-H), 4.50(1H, m, (4)′-H), 4.30(1H, m, 5′-H), 4.30(1H, m, (5)′-H), 4.30(1H, m, H of (5)-CH$_2$), 4.25(1H, m, 2′-H), 4.25(1H, m, (2)-H), 4.25(1H, m, (2)′-H), 4.20(1H, m, H of (5)-CH$_2$), 4.18(1H, m, H of 5-CH$_2$), 4.16 (1H, m, (3)″-H), 4.08 (1H, m, H of 5-CH$_2$), 4.07(1H, m, 2-H), 4.02(1H, m, 3′-H), 4.02(1H, m, (3)′-H), 3.85(1H, m, 5-H), 3.85(1H, m, (5)-H), 3.78 (1H, m, 3-H), 3.78 (1H, m, (3)-H), 3.76 (1H, m, 4″-H), 3.76(1H, m, 5″-H), 3.75(1H, m, 4-H), 3.75(1H, m, (4)-H), 3.58 (1H, m, 3″-H), 3.55($_1$H, m, (2)″-H), 3.18 (1H, t, J=8.2 Hz, 2″-H), 1.10(3H, d, J=6.7 Hz, H$_3$ of (5)′-CH$_3$), 1.09(3H, d, J=6.7 Hz, H$_3$ of 5′-CH$_3$)

Sugar composition:

L-fucose:unsaturated D-glucuronic acid:D-glucuronic acid:D-mannose=2:1:1:2 (L-fucose and D-mannose: each two molecules, unsaturated D-glucuronic acid and D-glucuronic acid: each one molecule).

Sulfate group:

six molecules (at the 2-and 4-positions of each L-fucose and the 6-position of each D-mannose).

The peaks in the $^1$H-NMR spectra are assignable respectively to the positions shown by the numerical values in the following formula (21):

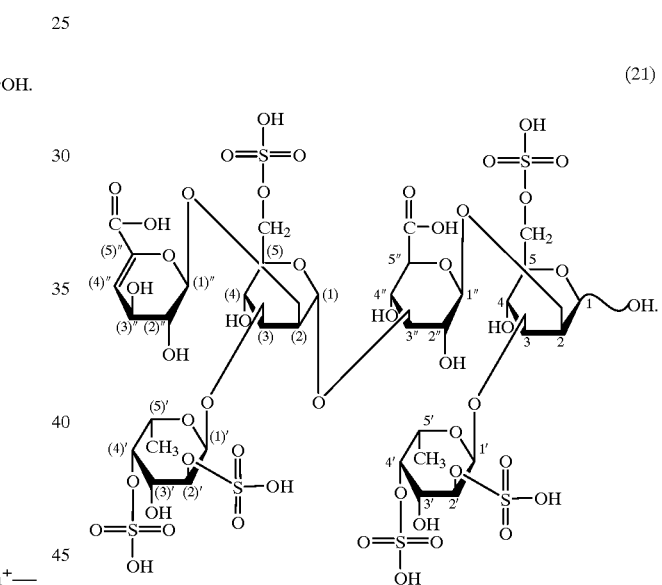

(21)

Physical properties of the compound (f):

Molecular weight: 644.

MS m/z: 687 [M+2Na$^+$—3H$^+$]$^-$.

MS/MS m/z: 97 [HSO$_4$]$^-$, 243 [sulfated L-fucose-H$^+$]$^-$, 421 [unsaturated D-glucuronic acid bonded to sulfated D-mannose+Na$^+$—H$_2$O—2H$^+$]$^-$.

$^1$NMR (D$_2$O) δ5.60(1H, d, J=3.4 Hz, 4″-H), 5.24(1H, br-s, 1-H), 5.08(1H, d, J=4.0 Hz, 1′-H), 4.94(1H, d, J=6.7 Hz, 1″-H), 4.45(1H, d-d, J=3.1, 10.4 Hz, 3′-H), 4.20(1H, br-s, 2-H), 4.14(2H, m, H$_2$ of 5-CH$_2$), 4.14(1H, m, 5′-H), 4.09, (1H, m, 3″-H), 4.01(1H, d, J=3.1 Hz, 4′-H), 3.91(1H, m, 5-H), 3.85(1H, m, 3-H), 3.85(1H, m, 2′-H), 3.75(1H, t, J=9.8 Hz, 4-H), 3.59(1H, t, J=6.7 Hz, 2″-H), 1.06(3H, d, J=6.4 Hz, H$_3$ of 5′-CH$_3$)

Sugar composition:

L-fucose:unsaturated D-glucuronic acid:D-mannose= 1:1:1 (L-fucose, D-mannose and unsaturated D-glucuronic acid: each one molecule).

Sulfate group:

two molecules (at the 3-position of L-fucose and the 6-position of D-mannose).

The peaks in the $^1$H-NMR spectra are assignable respectively to the positions shown by the numerical values in the following formula (22):

(22)

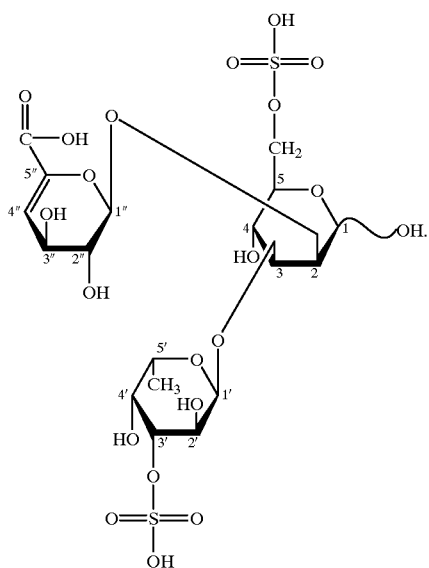

Physical properties of the compound (g):

Molecular weight: 632.

MS m/z: 631 [M–H$^+$]$^-$.

MS/MS m/z: 405 [sulfated L-fucose bonded to D-galactose-H$^+$]$^-$, 551 [L-fucose bonded to sulfated L-fucose bonded to D-galactose-H$^+$]$^-$ or [sulfated L-fucose bonded to L-fucose bonded to D-galactose-H$^+$]$^-$ or [M—SO$_3$—H$^+$]$^-$.

$^1$NMR (D$_2$O) δ5.15(1H, d, J=4.3 Hz, F$_1$1-H), 4.93(1H, d, J=3.7 Hz, F$_2$1-H), 4.53(1H, d-d, J=2.4, 10.4 Hz, F$_1$3-H), 4.49(1H, d, J=7.6 Hz, G$_1$1-H), 4.46(1H, d-d, J=3.1, 10.7 Hz, F$_2$3-H), 4.36(1H, q, J=6.7 Hz F$_2$5-H), 4.14(1H, q, J=6.7 Hz F$_1$5-H), 4.09(1H, d, J=2.4 Hz F$_1$4-H), 4.03(1H, d, J=3.1 Hz F$_2$4-H), 3.97 (1H, d-d, J=4.3, 10.4 Hz, F$_1$2-H) , 3.90 (1H, br-s, G$_1$4-H, 3.81 (1H, d-d, J=3.7, 10.7 Hz, F$_2$2-H), 3.59 (1H, m, G$_1$3-H), 3.59(1H, m, G$_1$5-H), 3.59(2H, m, H$_2$ of G$_1$5-CH$_2$), 3.56(1H, m, G$_1$2-H), 1.19(3H, d, J=6.7 Hz, H$_3$ of F$_1$5-CH$_3$), 1.14(3H, d, J=6.7 Hz, H$_3$ of F$_2$5-CH$_3$)

Sugar composition:

L-fucose:D-galactose=2:1 (two L-fucose molecules and one D-galactose molecule).

Sulfate group:

two molecules (at the 3-position of each L-fucose).

The peaks in the $^1$H-NMR spectra are assignable respectively to the positions shown by the numerical values in the following formula (23):

(23)

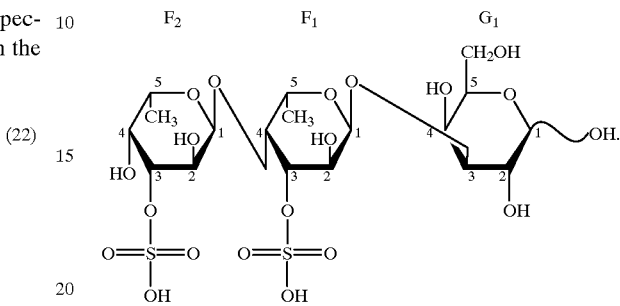

Physical properties of the compound (h):

Molecular weight: 1358.

MS m/z: 1445 [M+4Na$^+$—5H$^+$]$^-$.

MS/MS m/z: 97 [HSO$_4$]$^-$, 225 [sulfated L-fucose-H$_2$O—H$^+$]$^-$, 1197 [M—2So$_3$-H$^+$]$^-$.

$^1$NMR (D$_2$O) δ5.19(1H, d, J=4.3 Hz, F$_1$1-H), 4.93(1H, d, J=3.7 Hz, F$_2$1-H), 4.62(1H, m, G$_2$1-H), 4.59(1H, m, G$_1$1-H), 4.54(1H, d-d, J=2.7, 10.6 Hz, F$_1$3-H), 4.46(1H, m, F$_2$3-H), 4.46(1H, d, J=7.6 Hz G$_3$1-H), 4.41(1H, br-s, G$_1$4-H), 4.41 (1H, d, J=7.6 Hz, G$_4$1-H), 4.37(1H, q, J=6.4 Hz F$_2$5-H), 4.27(1H, m, G$_1$3-H), 4.24(1H, br-s, G$_3$4-H), 4.21(1H, m, G$_3$3-H), 4.19(1H, m, G$_4$3-H), 4.15(1H, br-s, G$_4$4-H), 4.13 (1H, q, J=6.7 Hz, F$_1$5-H), 4.09(1H, d, J=2.7 Hz, F$_1$4-H), 4.04(1H, d, J=2.8 Hz, F$_2$4-H), 3.98(1H, m, H of G$_1$5-CH$_2$), 3.96(1H, d-d, J=4.3, 10.6 Hz, F$_1$2-H), 3.88(1H, br-s, G$_2$4-H), 3.93(1H, m, H of G$_3$5-CH$_2$), 3.86(1H, m, G$_1$5-H), 3.81(1H, m, F$_2$2-H), 3.81(1H, m, H of G$_1$5-CH$_2$), 3.80(1H, m, G$_3$5-H), 3.80(1H, m, H of G$_3$5-CH$_2$), 3.66(1H, m, G$_2$3-H), 3.65(1H, m, G$_1$2-H), 3.64(1H, m, H of G$_2$5-CH$_2$), 3.64(1H, m, H of G$_4$5-CH$_2$), 3.61(1H, m, G$_4$5-H), 3.58(1H, m, G$_2$2-H), 3.56(1H, m, H of G$_2$5-CH$_2$), 3.56(1H, m, H of G$_4$5-CH$_2$), 3.55(1H, m, G$_4$2-H), 3.54(1H, m, G$_2$5-H), 3.54 (1H, m, G$_3$2-H), 1.20(3H, d, J=6.7 Hz, H$_3$ of F$_1$5-CH$_3$), 1.14(3H, d, J=6.4 Hz, H$_3$ of F$_2$5-CH$_3$)

Sugar composition:

L-fucose:D-galactose=1:2 (two L-fucose molecules and four D-galactose molecules).

Sulfate group:

five molecules (at the 3-position of each L-fucose, the 3-position of D-galactose of the reducing end, and the 3-position of D-galactose bonded to the 6-position of D-galactose of the reducing end, and the 3-position of D-galactose bonded to the 6-position of the above-mentioned D-galactose).

The peaks in the $^1$H-NMR spectra are assignable respectively to the positions shown by the numerical values in the following formula (24):

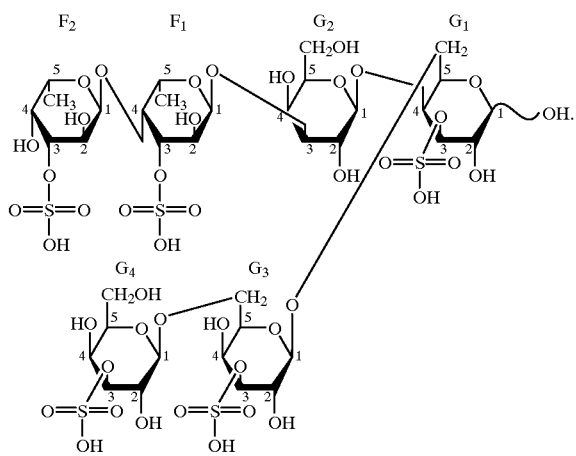

(24)

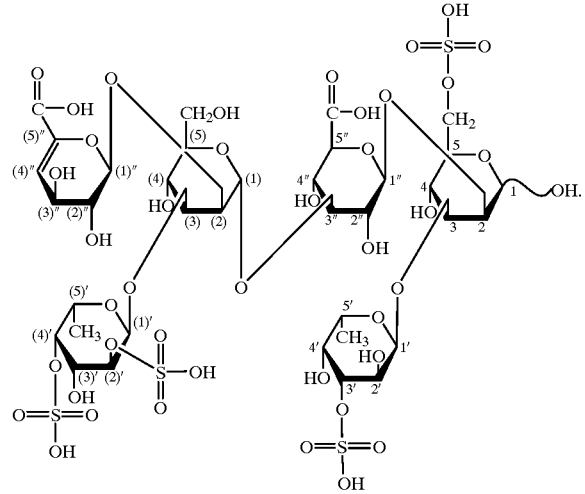

(25)

Physical properties of the compound (i):

Molecular weight: 1288.

MS m/z: 1149 [M+Na$^+$-2SO$_3$-2H$^+$]$^-$.

MS/MS m/z: 97 [HSO$_4$]$^-$, 345 [disulfated L-fucose+Na$^+$-2H$^+$]$^-$.

$^1$H-NMR (D$_2$O)

δ5.68(1H, d, J=3.4 Hz, (4)"-H), 5.34(1H, br-s, (1)-H), 5.19(1H, m, 1-H), 5.19(1H, m, (1)'-H), 4.94(1H, m, 1'-H), 4.94(1H, d, J=6.4 Hz, (1)"-H), 4.72(1H, d, J=7.9 Hz, 1"-H), 4.54 (1H, m, (4)'-H), 4.48(1H, d-d, J=3.3, 10.6 Hz, 3'-H), 4.38(1H, q, J=6.4 Hz, 5'-H), 4.34(1H, q, J=6.7 Hz, (5)'-H), 4.29(1H, m, (2)'-H), 4.20(1H, m, H of 5-CH$_2$), 4.14(1H, m, (2)-H), 4.13(1H, m, (3)"-H), 4.09(1H, m, H of 5-CH$_2$), 4.08(1H, m, 2-H), 4.05(1H, d, J=3.3 Hz, 4'-H), 3.99(1H, m, (3)'-H), 3.89(1H, m, 5-H), 3.83(1H, m, 4"-H), 3.81(1H, m, 2'-H), 3.80(1H, m, 4-H), 3.78(1H, m, 3-H), 3.78(1H, m, (3)-H), 3.68(2H, m, H$_2$ of (5)-CH$_2$), 3.62(1H, m, (2)"-H), 3.60(1H, m, 3"-H), 3.60(1H, m, 5"-H), 3.58(1H, m, (5)-H), 3.56(1H, m, (4)-H), 3.17(1H, t, J=7.9 Hz, 2"-H), 1.15(3H, d, J=6.4 Hz, H$_3$ of 5'-CH$_3$), 1.11(3H, d, J=6.7 Hz, H$_3$ of (5)'-CH$_3$)

Sugar composition:

L-fucose:unsaturated D-glucuronic acid:D-glucuronic acid:D-mannose=2:1:1:2 (L-fucose and D-mannose: each two molecules, unsaturated D-glucuronic and D-glucuronic acid: each one molecule).

Sulfate group:

four molecules (at the 3-position of L-fucose bonded to D-mannose of the reducing end, the 2- and 4-positions of another L-fucose, and the 6-position of D-mannose on the reducing end side).

The peaks in the $^1$H-NMR spectra are assignable respectively to the positions shown by the numerical values in the following formula (25):

Also, the sugar compounds of the first invention of the present invention can be produced by treating fucoidan with a cell extract or culture supernatant of the bacterium of the third invention of the present invention belonging to the genus Fucoidanobacter.

The strain of the third invention of the present invention may be an arbitrary one so long as it is a strain of the present invention belonging to the genus Fucoidanobacter. As a particular example thereof, citation may be made of *Fucoidanobacter marinus* SI-0098, strain.

This strain *Fucoidanobacter marinus* SI-0098, which has been found out for the first time by the present inventors from seawater in Aomori, has the following mycological properties.

2. *Fucoidanobacter marinus* SI-0098 Strain a. Morphological Properties

| (1) Short rod (sometimes diplococcal); | |
| --- | --- |
| width | : 0.5–0.7 μm |
| length | : 0.5–0.7 μm |
| (2) Spore | : none |
| (3) Gram-staining | : – | b. Physiological Properties

| (1) Growth temperature range : capable of growing at 37° C., appropriate growth temperature ranging from 15 to 28° C. | |
| --- | --- |
| (2) Attitude to oxygen | : aerobic |
| (3) Catalase | : + |
| (4) Oxidase | : – |
| (5) Urease | : – |
| (6) Hydrolysis starch | : + |
| gelatin | : – |
| casein | : – |
| esculin | : + |
| (7) Reduction of nitrate | : – |
| (8) Indole formation | : – |
| (9) Hydrogen sulfide formation | : + |
| (10) Solidification of milk | : – |
| (11) Sodium requirement | : + |
| (12) Salt requirement | |
| Growth in NaCl-free medium | : – |

-continued

|      |                                    |                              |
| ---- | ---------------------------------- | ---------------------------- |
|      | Growth in 1% NaCl medium           | : –                          |
|      | Growth in seawater medium          | : +                          |
| (13) | Quinone                            | : menaquinone 7              |
| (14) | GC content of intracellular DNA    | : 61%                        |
| (15) | Diaminopimelic acid in cell wall   | : –                          |
| (16) | Glycolyl test                      | : –                          |
| (17) | Presence of hydroxy fatty acid     | : +                          |
| (18) | OF-test                            | : O                          |
| (19) | Colony color                       | : forming no characteristic color |
| (20) | Motility                           | : yes                        |
| (21) | Gliding                            | : none                       |
| (22) | Flagellum                          | : polar monotrichous.        |

According to the classification described in Bergey's Manual of Determinative Bacteriology, 9 (1994), this strain falls in Group 4 (Gram-negative aerobic bacilli and cocci). However, this strain largely differs from the bacteria belonging to Group 4 in having menaquinone in the electron transport chain and containing 61% of GC. Fundamentally, gram-negative bacteria have ubiquinone in the electron transport chain while gram-positive bacteria have menaquinone.

Although gram-negative bacteria belonging to the genera Flavobacterium and Cytophaga exceptionally have menaquinone in the electron transport chain, they are largely different in GC content from the above-mentioned strain, such that *Cytophaga arvensicola*, which is a soil bacterium contains from 43 to 46% of GC and *Cytophaga diffluens, C. fermentans, C. marina* and *C. uliginosa*, which are marine bacteria each contains 42% of GC. When this strain is compared in the homology in 16SrDNA sequence with strains which have been identified, even the most homologous one (*Verrucomicrobium spinosum*) shows a homology of 76.6% therewith. It is widely known that two bacteria with a homology of 90% or less with each other are different in genus. Accordingly, the present inventors have decided that this strain is a novel bacterium belonging to none of the existing genera and named it *Fucoidanobacter marinus* SI-0098.

The above strain is designated as *Fucoidanobacter marinus* SI-0098 and has been deposited at National Institute of Bioscience and Human-Technology, Agency of Industrial Science and Technology (1-3, Higashi 1-chome, Tsukuba, Ibaragi, 305 JAPAN) under the accession number FERM BP-5403 (original deposition was made on Mar. 29, 1995 and transfer to international deposition was requested on Feb. 15, 1996).

It is possible that a microorganism of the third invention of the present invention belonging to the genus Fucoidanobacter is incubated in a medium and fucoidan is treated with the cell extract or the culture supernatant to thereby liberate the sugar compounds of the first invention of the present invention. The microorganism to be used therefor may be an arbitrary one, so long as it belongs to the genus Fucoidanobacter and is capable of giving the sugar compounds of the first invention of the present invention when fucoidan is treated with the cell extract or the culture supernatant thereof. As a particular example of the strain, citation may be made of *Fucoidanobacter marinus* SI-0098 strain.

The nutrients to be added to the medium of the bacterial strain belonging to the genus Fucoidanobacter may be arbitrary ones so long as the strain employed can utilize them so as to give the cell extract or the culture supernatant by which the sugar compounds of the first invention of the present invention can be produced. Appropriate examples of the carbon source include fucoidan, marine alga powder, alginic acid, fucose, glucose, mannitol, glycerol, saccharose, maltose, lactose and starch, while appropriate examples of the nitrogen source include yeast extract, peptone, casamino acids, corn steep liquor, meat extract, defatted soybean, ammonium sulfate and ammonium chloride. The medium may further contain inorganic substances and metal salts such as sodium salts, phosphates, potassium salts, magnesium salts and zinc salts.

This strain also grows well in seawater or artificial seawater containing the above-mentioned nutritional sources.

To incubate the bacterium belonging to the genus of Fucoidanobacter according to the third invention of the present invention, it is generally preferable that the incubation temperature ranges from 15 to 30° C. and the pH value of the medium ranges from 5 to 9. The endo-fucoidan-lyase activity in the cell extract and culture supernatant attains the maximum by incubating the strain under aeration and agitation for 5 to 72 hours. As a matter of course, the incubation conditions are appropriately selected depending on the strain employed, the medium composition, etc. so as to achieve the maximum activity of endo-fucoidan-lyase of the intracellular extract and the culture supernatant.

The *Fucoidanobacter marinus* SI-0098 strain is incubated in an appropriate medium and, after the completion of the incubation, the culture medium is centrifuged to thereby give the cells and the culture supernatant. Further the cells thus harvested are disrupted by a means commonly employed for disrupting cells such as ultrasonication. By centrifuging the disrupted cells, a cell extract can be obtained.

Subsequently, the culture supernatant or the cell extract is concentrated by ultrafiltration and mixed with a phosphate buffer containing sodium chloride. Then fucoidan is added thereto and reacted therewith.

After the completion of the reaction, the reaction mixture is fractionated by using a column for molecular weight fractionation. Thus the sugar compounds of the first invention of the present invention can be obtained.

The sugar compounds of the first invention of the present invention are useful as a reagent for the sugar chain technology. By pyridyl-(2)-aminating (PA) these compounds in accordance with the method described in Japanese Patent Publication No. 65108/1993, it is possible to give PA compounds which are highly useful as a reagent for the sugar chain technology. Furthermore, it is expected that the physiological activities of the sugar compounds of the present invention make them applicable to anticancer, cancerous metastasis-inhibitory and antiviral drugs.

BEST MODE FOR CARRYING OUT THE INVENTION

The following Examples will be given in order to illustrate examples of the process for producing the sugar compounds of the first invention of the present invention, though it is to be understood that the present invention is not restricted thereto.

EXAMPLE 1

Flavobacterium sp. SA-0082 (FERM BP-5402) was inoculated into 600 ml of a medium comprising an artificial seawater (pH 7.5, mfd. by Jamarin Laboratory) containing 0.1% of glucose, 1.0% of peptone and 0.05% of yeast extract which had been pipetted into a 2-l Erlenmeyer flask and sterilized at 120° C. for 20 minutes. Then the strain was incubated therein at 24° C. for 20 hours to thereby give a seed culture. Into a 30-l jar fermenter was fed 20 l of a medium comprising an artificial seawater (pH 7.5, mfd. by Jamarin Laboratory) containing 0.3% of fucoidan originating in *Kjellmaniella crassifolia*, 0.5% of peptone, 0.01% of yeast extract and 0.01% of a defoaming agent (KM70 mfd. by Shin-Etsu Chemical Co., Ltd.) and sterilized at 120° C. for 20 minutes. After cooling, the medium was inoculated with 600 ml of the above-mentioned seed culture, which was then incubated therein at 24° C. for 20 hours under aerating at a rate of 10 l/min and agitating at 125 rpm. After the completion of the incubation, the culture medium was centrifuged to thereby obtain the cells and the culture supernatant.

The culture supernatant was concentrated by ultrafiltration (exclusion molecular weight of membrane: 10,000, mfd. by Amicon) and the endo-fucoidan-lyase of the present invention was assayed. Thus an activity of 6 mU/ml of the culture medium was detected.

Separately, the cells obtained by the main incubation were suspended in a 20 mM acetate-phosphate buffer (pH 7.5) containing 200 mM of sodium chloride, disrupted by ultra-sonication and centrifuged to thereby give a cell extract. When the endo-fucoidan-lyase of the present invention in this cell extract was assayed, an activity of 20 mU/ml of the culture medium was detected.

To the above-mentioned concentrate of the culture supernatant was added ammonium sulfate so as to establish 90% saturation finally. After dissolving by stirring, the mixture was centrifuged and the precipitate was suspended in the same buffer as the above-mentioned one in which the cells were suspended. Then the suspension was thoroughly dialyzed against a 20 mM acetate-phosphate buffer (pH 7.5) containing 50 mM of sodium chloride. After eliminating the precipitate formed by the dialysis by centrifugation, it was adsorbed on a DEAE-Sepharose FF column which had been equilibrated with a 20 mM acetate-phosphate buffer (pH 7.5) containing 50 mM of sodium chloride. Then the adsorbed matter was well washed with the same buffer and developed by linear gradient elution with sodium chloride of 50 mM to 600 mM. The active fractions were combined and sodium chloride was added thereto so as to give a final concentration of 4 M. Next, it was adsorbed on a Phenyl Sepharose CL-4B column which had been equilibrated with a 20 mM phosphate buffer (pH 8.0) containing 4 M of sodium chloride. Then the adsorbed matter was well washed with the same buffer and developed by linear gradient elution with sodium chloride of 4 M to 1 M. The active fractions were combined and concentrated with an ultrafilter (mfd. by Amicon). Next, it was subjected to gel filtration with the use of Sephacryl S-200 gel which had been equilibrated with a 10 mM phosphate buffer containing 50 mM of sodium chloride. The active fractions were combined and sodium chloride was added thereto so as to give a final concentration of 3.5 M. Next, it was adsorbed on a Phenyl Sepharose HP column which had been equilibrated with a 10 mM phosphate buffer (pH 8) containing 3.5 M of sodium chloride. Then the adsorbed matter was washed with the same buffer and developed by linear gradient elution with sodium chloride of 3.5 M to 1.5 M. The active fractions were combined to thereby give the purified enzyme. The molecular weight of the enzyme determined from the retention time in Sephacryl S-200 was about 70,000. Table 1 summarizes the above-mentioned purification steps.

TABLE 1

| Step | Total protein (mg) | Total activity (mU) | Specific activity (mU/mg) | Yield (%) |
| --- | --- | --- | --- | --- |
| cell extract | 980 | 114,000 | 116 | 100 |
| ammonium sulfate-salting out | 473 | 108,000 | 228 | 94.7 |
| DEAE-Sepharose FF | 216 | 86,400 | 400 | 75.8 |
| Phenyl Sepharose CL-4B | 21.9 | 57,300 | 2,620 | 50.3 |
| Sephacryl S-200 | 3.70 | 46,200 | 12,500 | 40.5 |
| Phenyl Sepharose HP | 1.53 | 41,200 | 27,000 | 36.1 |

EXAMPLE 2

Flavobacterium sp. SA-0082 (FERM BP-5402) was inoculated into 600 ml of a medium comprising an artificial seawater (pH 7.5, mfd. by Jamarin Laboratory) containing 0.25% of glucose, 1.0% of peptone and 0.05% of yeast extract which had been pipetted into a 2-l Erlenmeyer flask and sterilized at 120° C. for 20 minutes. Then the strain was incubated therein at 24° C. for 24 hours to thereby give a seed culture. Into a 30-l jar fermenter was fed 20 l of a medium comprising an artificial seawater (pH 7.5, mfd. by Jamarin Laboratory) containing 0.25% of glucose, 1.0% of peptone, 0.05% of yeast extract and 0.01% of a defoaming agent (KM70 mfd. by Shin-Etsu Chemical Co., Ltd.) and sterilized at 120° C. for 20 minutes. After cooling, the medium was inoculated with 600 ml of the above-mentioned seed culture, which was then incubated therein at 24° C. for 24 hours under aerating at a rate of 10 l/min and agitating at 125 rpm. After the completion of the incubation, the culture medium was centrifuged to thereby give the cells and the culture supernatant.

The culture supernatant was concentrated by ultrafiltration (exclusion molecular weight of membrane: 10,000, mfd. by Amicon) and the endo-fucoidan-lyase of the present invention was assayed. Thus an activity of 1 mU/ml of the culture medium was detected.

Separately, the cells obtained by the main incubation were suspended in a 20 mM acetate-phosphate buffer (pH 7.5) containing 200 mM of sodium chloride, disrupted by ultra-sonication and centrifuged to thereby give a cell extract. When the endo-fucoidan-lyase of the present invention in this cell extract was assayed, an activity of 5 mU/ml of the culture medium was detected.

To this extract was added ammonium sulfate so as to establish 90% saturation finally. After dissolving by stirring, the mixture was centrifuged and the precipitate was suspended in the same buffer as the above-mentioned one in which the cells were suspended. Then the suspension was thoroughly dialyzed against a 20 mM acetate-phosphate buffer (pH 7.5) containing 50 mM of sodium chloride. After eliminating the precipitate formed by the dialysis by centrifugation, it was adsorbed on a DEAE-Sepharose FF column which had been equilibrated with a 20 mM acetate-phosphate buffer (pH 7.5) containing 50 mM of sodium chloride. Then the adsorbed matter was well washed with the same buffer and developed by linear gradient elution with sodium chloride of 50 mM to 600 mM. The active fractions were combined and sodium chloride was added thereto so as to give a final concentration of 4 M. Next, it was adsorbed on a Phenyl Sepharose CL-4B column which had been equilibrated with a 20 mM phosphate buffer (pH 8.0) containing 4 M of sodium chloride. Then the adsorbed matter was well washed with the same buffer and developed by linear gradient elution with sodium chloride of 4 M to 1 M. The active fractions were combined and concentrated with an ultra filter. Next, it was subjected to gel filtration with the use of Sephacryl S-300 which had been equilibrated with a 10 mM phosphate buffer containing 50 mM of sodium chloride. The active fractions were combined. The molecular weight of the enzyme determined from the retention time in Sephacryl S-300 was about 460,000. Next, the active fraction was dialyzed against a 10 mM phosphate buffer (pH 7) containing 250 mM of sodium chloride. The enzyme solution was adsorbed on a Mono Q HR5/5 column which had been equilibrated with a 10 mM phosphate buffer (pH 7) containing 250 mM of sodium chloride. The adsorbed matter was well washed with the same buffer and developed by linear gradient elution with sodium chloride of 250 mM to 450 mM. The active fractions were combined to thereby give the purified enzyme. Table 2 summarizes the above-mentioned purification steps.

TABLE 2

| Step | Total protein (mg) | Total activity (mU) | Specific activity (mU/mg) | Yield (%) |
|---|---|---|---|---|
| cell extract | 61,900 | 101,000 | 1.63 | 100 |
| ammonium sulfate-salting out | 33,800 | 88,600 | 2.62 | 87.7 |
| DEAE-Sepharose FF | 2,190 | 40,400 | 18.4 | 40.0 |
| Phenyl Sepharose CL-4B | 48.2 | 29,000 | 601 | 28.7 |
| Sephacryl S-300 | 7.24 | 19,600 | 2,710 | 19.4 |
| Mono Q | 0.824 | 15,000 | 18,200 | 14.9 |

EXAMPLE 3

Purified fucoidan originating in *Kjellmaniella crassifolia* was treated with the endo-fucoidan-lyase of the present invention obtained in Example 1 (the intracellular enzyme) to thereby prepare the degradation products thereof.

Namely, 16 ml of a 2.5% fucoidan solution, 12 ml of a 50 mM phosphate buffer (pH 7.5), 4 ml of a 4 M solution of sodium chloride and 8 ml of a 32 mU/ml solution of the endo-fucoidan-lyase of the present invention were mixed together and reacted at 25° C. for 48 hours.

Then the reaction mixture was subjected to molecular weight fractionation by using a Cellulofine GCL-300 column (mfd. by Seikagaku Kogyo) and the fraction of molecular weight of not more than 2,000 was taken up. After desalting with a Micro Acilyzer G3 (mfd. by Asahi Chemical Industry Co., Ltd.), this fraction was separated into three fractions by DEAE-Sepharose FF to thereby give 41 mg, 69 mg and 9.6 mg of the above-mentioned compounds (a), (b) and (c), respectively.

EXAMPLE 4

Purified fucoidan originating in *Kjellmaniella crassifolia* was treated with the endo-fucoidan-lyase of the present invention obtained in Example 2 (the extracellular enzyme) to thereby prepare the degradation products thereof.

Namely, 16 ml of a 2.5% fucoidan solution, 12 ml of a 50 mM phosphate buffer (pH 7.5), 4 ml of a 4 M solution of sodium chloride and 8 ml of a 32 mU/ml solution of the endo-fucoidan-lyase of the present invention were mixed together and reacted at 25° C. for 48 hours.

Then the reaction mixture was subjected to molecular weight fractionation by using a Cellulofine GCL-300 column (mfd. by Seikagaku Kogyo) and the fraction of molecular weight of not more than 2,000 was taken up. After desalting with a Micro Acilyzer G3 (mfd. by Asahi Chemical Industry Co., Ltd.), this fraction was separated into three fractions by DEAE-Sepharose FF and freeze-dried to thereby give 40 mg, 65 mg and 9.2 mg of the above-mentioned compounds (a), (b) and (c), respectively.

EXAMPLE 5

*Fucoidanobacter marinus* SI-0098 strain (FERM BP-5403) was inoculated into 600 ml of a medium comprising an artificial seawater (pH 7.5, mfd. by Jamarin Laboratory) containing 0.3% of fucoidan originating in *Kjellmaniella crassifolia*, 0.5% of peptone, 0.05% of yeast extract and 0.01% of a defoaming agent (KM70 mfd. by Shin-Etsu Chemical Co., Ltd.) and sterilized (120° C., 20 minutes). Then the strain which had been pipetted into a 2-l Erlenmeyer flask and sterilized at 120° C. for 20 minutes. Then the strain was incubated therein at 25° C. for 48 hours under agitating at 120 rpm. After the completion of the incubation, the culture medium was centrifuged to thereby give the cells and the culture supernatant.

The culture supernatant was concentrated by ultrafiltration (exclusion molecular weight of membrane: 10,000, mfd. by Amicon) and the endo-fucoidan-lyase of the present invention was assayed. Thus an activity of 0.2 mU/ml of the culture medium was detected.

Separately, the cells obtained by the main incubation were suspended in a 20 mM acetate-phosphate buffer (pH 7.5) containing 200 mM of sodium chloride, disrupted by ultrasonication and centrifuged to thereby give a cell extract. When the endo-fucoidan-lyase of the present invention in this cell extract was assayed, an activity of 20 mU/ml of the culture medium was detected.

EXAMPLE 6

Purified fucoidan originating in *Kjellmaniella crassifolia* was treated with the intracellular enzyme of the *Fucoidanobacter marinus* SI-0098 strain of the present invention obtained in Example 5 to thereby prepare the degradation products thereof.

Namely, 16 ml of a 2.5% fucoidan solution, 20 ml of a 100 mM phosphate buffer (pH 8.0) containing 800 mM of sodium chloride and 4 ml of a 20 mU/ml solution of the intracellular enzyme of the *Fucoidanobacter marinus* SI-0098 strain of the present invention obtained in Example 5 were mixed together and reacted at 25° C. for 48 hours.

Then the reaction mixture was subjected to molecular weight fractionation by using a Cellulofine GCL-300 column and the fraction of molecular weight of not more than 2,000 was taken up. After desalting with a Micro Acilyzer G3, this fraction was separated into three fractions by DEAE-Sepharose FF and freeze-dried to thereby give 38 mg, 60 mg and 8.2 mg of the above-mentioned compounds (a), (b) and (c), respectively.

The present invention thus provides a novel endo-fucoidan-lyase which is useful in the analysis of the structure of fucoidan, the identification of the enzymatic degradation products of fucoidan and studies relating to fucoidan, for example, sugar compounds usable in the detection of biological activities of fucoidan, the partial degradation of fucoidan and the production of fucoidan oligosaccharides.

What is claimed is:

1. An isolated endo-fucoidan-lyase having the following physicochemical properties:

(I) function: acting on fucoidan to cause the liberation of at least the sugar compounds represented by the following structures (7) and (8):

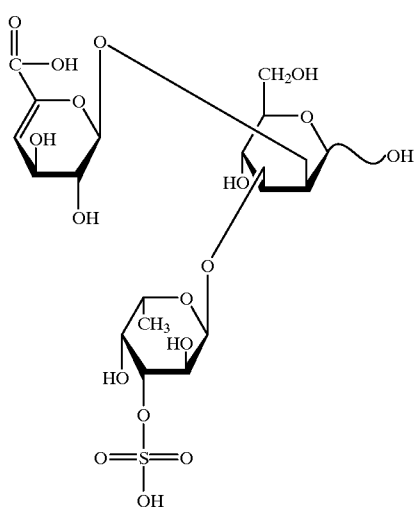

(7)

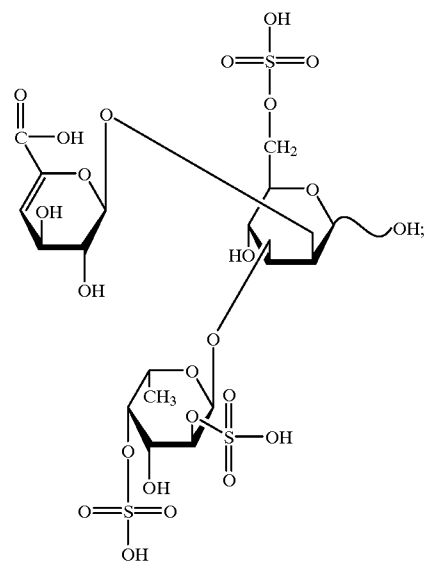

(8)

(II) optimum pH value: ranging from pH 6 to 10; and
(III) optimum temperature: ranging from 30 to 40° C.

2. The endo-fucoidan-lyase according to claim 1, which is derived from the bacterium belonging to the genus Flavobacterium.

3. The endo-fucoidan-lyase according to claim 2, which is derived from Flavobacterium sp. FERM BP-5402.

* * * * *